(12) United States Patent
Anderskewitz et al.

(10) Patent No.: US 8,871,783 B2
(45) Date of Patent: Oct. 28, 2014

(54) SUBSTITUTED 2-AZA-BICYCLO[2.2.1]HEPTANE-3-CARBOXYLIC ACID (CYANO-METHYL)-AMIDES INHIBITORS OF CATHEPSIN C

(71) Applicants: Ralf Anderskewitz, Laupheim (DE); Marc Grundl, Biberach an der Riss (DE); Gerd Morschhaeuser, Biberach an der Riss (DE); Thorsten Oost, Biberach an der Riss (DE); Alexander Pautsch, Biberach an der Riss (DE)

(72) Inventors: Ralf Anderskewitz, Laupheim (DE); Marc Grundl, Biberach an der Riss (DE); Gerd Morschhaeuser, Biberach an der Riss (DE); Thorsten Oost, Biberach an der Riss (DE); Alexander Pautsch, Biberach an der Riss (DE)

(73) Assignee: Boehringer Ingelheim International GmBh, Ingelheim am Rhein (DE)

( * ) Notice: Subject to any disclaimer, the term of this patent is extended or adjusted under 35 U.S.C. 154(b) by 0 days.

(21) Appl. No.: 14/205,881

(22) Filed: Mar. 12, 2014

(65) Prior Publication Data
US 2014/0275114 A1    Sep. 18, 2014

(30) Foreign Application Priority Data

Mar. 14, 2013 (EP) .................................... 13159245
May 31, 2013 (EP) .................................... 13170008

(51) Int. Cl.
*A61K 31/44*    (2006.01)
*C07D 221/02*    (2006.01)

(52) U.S. Cl.
USPC .......................................... 514/299; 546/112

(58) Field of Classification Search
USPC .......................................... 546/112; 514/299
See application file for complete search history.

(56) References Cited

U.S. PATENT DOCUMENTS 7,012,075 B2 *    3/2006    Prasit et al. .............. 514/252.13

FOREIGN PATENT DOCUMENTS

| WO | 2004110988 A1 | 12/2004 |
|----|---------------|---------|
| WO | 2009047829 A1 | 4/2009 |
| WO | 2009074829 A1 | 6/2009 |
| WO | 2010128324 A1 | 11/2010 |
| WO | 2010142985 A1 | 12/2010 |
| WO | 2012119941 A1 | 9/2012 |
| WO | 2013041497 A1 | 3/2013 |

OTHER PUBLICATIONS

Abstract in English for WO 2009/047829, publication date Apr. 16, 2009.
Bondebjerg, J. et al., "Dipeptidyl nitriles as human dipeptidyl peptidase I inhibitors." Bioorganic & Medicinal Chemistry Letters, 2006, vol. 16, No. 13, pp. 3614-3617.
Guay, D. et al., "Design and synthesis of dipeptidyl nitriles as potent, selective, and reversible inhibitors of cathespin C." Bioorganic & Medicinal Chemistry Letters, 2009, vol. 19, No. 18, pp. 5392-5396.
International Search Report for PCT/EP2014/054794 mailing date Apr. 2, 2014.
International Search Report for PCT/EP2014/054798 mailing date Apr. 4, 2014.
International Search Report for PCT/EP2014/054802 mailing date Apr. 10, 2014.
International Search Report for PCT/EP2014/054827 mailing date Apr. 28, 2014.

* cited by examiner

*Primary Examiner* — Niloofar Rahmani
(74) *Attorney, Agent, or Firm* — Michael P. Morris; Anthony P. Bottino

(57) ABSTRACT

This invention relates to 2-Aza-bicyclo[2.2.1]heptane-3-carboxylic acid (cyano-methyl)-amides of formula 1

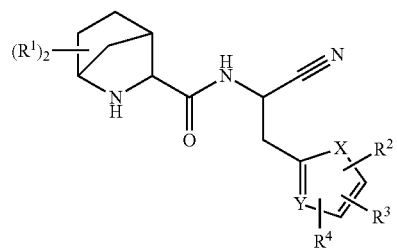

and their use as inhibitors of Cathepsin C, pharmaceutical compositions containing the same, and methods of using the same as agents for treatment and/or prevention of diseases connected with dipeptidyl peptidase I activity, e.g. respiratory diseases.

14 Claims, No Drawings

SUBSTITUTED 2-AZA-BICYCLO[2.2.1]HEPTANE-3-CARBOXYLIC ACID (CYANO-METHYL)-AMIDES INHIBITORS OF CATHEPSIN C

FIELD OF INVENTION

This invention relates to 2-Aza-bicyclo[2.2.1]heptane-3-carboxylic acid (cyano-methyl)-amides of formula 1

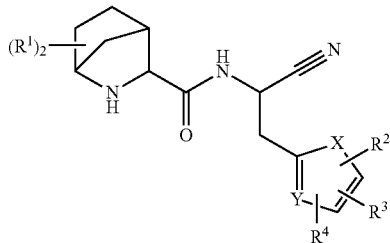

and their use as inhibitors of Cathepsin C, pharmaceutical compositions containing the same, and methods of using the same as agents for treatment and/or prevention of diseases connected with dipeptidyl peptidase I activity, e.g. respiratory diseases.

BACKGROUND INFORMATION

WO2004110988 discloses peptidyl nitrile inhibitors as dipeptidyl-peptidase I (DPPI) inhibitors for the treatment of a series of diseases.

WO2009074829 and WO2010142985 also disclose peptidyl nitrile inhibitors as dipeptidyl-peptidase I (DPPI) inhibitors for the treatment asthma, COPD or allergic rhinitis.

BRIEF SUMMARY OF THE INVENTION

Dipeptidyl-aminopeptidase I (DPPI or Cathepsin C; EC3.4.141), is a lysosomal cysteine protease capable of removing dipeptides from the amino terminus of protein substrates. DPPI was first discovered by Gutman and Fruton in 1948 (J. Biol. Chem. 174: 851-858, 1948). The cDNA of the human enzyme has been described in 1995 (Paris et al.; FEBS Lett 369: 326-330, 1995). The DPPI protein is processed into a mature proteolytically active enzyme consisting of a heavy chain, a light chain, and a propeptide that remains associated with the active enzyme (Wolters et al.; J. Biol. Chem. 273: 15514-15520, 1998). Whereas the other cysteine Cathepsins (e.g. B, H, K, L and S) are monomers, DPPI is a 200-kD tetramer with 4 identical subunits, each composed of the 3 different polypeptide chains. DPPI is constitutively expressed in many tissues with highest levels in lung, kidney, liver and spleen (Kominami et al.; Biol. Chem. Hoppe Seyler 373: 367-373, 1992). Consistent with its role in the activation of serine proteases from hematopoetic cells, DPPI is also relatively highly expressed in neutrophils, cytotoxic lymphocytes, natural killer cells, alveolar macrophages and mast cells. Recent data from DPPI deficient mice suggest that, besides being an important enzyme in lysosomal protein degradation, DPPI also functions as the key enzyme in the activation of granule serine proteases in cytotoxic T lymphocytes and natural killer cells (granzymes A and B; Pham et al.; Proc. Nat. Acad. Sci. 96: 8627-8632, 1999), mast cells (chymase and tryptase; Wolter et al.; J. Biol. Chem. 276: 18551-18556, 2001), and neutrophils (Cathepsin G, elastase and proteinase 3; Adkison et al.; J. Clin. Invest. 109: 363.371, 2002). Once activated, these proteases are capable of degrading various extracellular matrix components, which can lead to tissue damage and chronic inflammation.

Thus, inhibitors of Cathepsin C could potentially be useful therapeutics for the treatment of neutrophil-dominated inflammatory diseases such as chronic obstructive pulmonary disease (COPD), pulmonary emphysema, asthma, multiple sclerosis, and cystic fibrosis (Guay et al.; Curr. Topics Med. Chem. 10: 708-716, 2010; Laine and Busch-Petersen; Expert Opin. Ther. Patents 20: 497-506, 2010). Rheumatoid arthritis is also another chronic inflammatory disease where DPPI appears to play a role. Neutrophils are recruited to the site of joint inflammation and release Cathepsin G, elastase and proteinase 3, proteases which are believed to be responsible for cartilage destruction associated with rheumatoid arthritis. Indeed, DPPI deficient mice were protected against acute arthritis induced by passive transfer of monoclonal antibodies against type II collagen (Adkison et al.; J. Clin. Invest. 109: 363.371, 2002).

In light of the role DPPI plays in activating certain pro-inflammatory serine proteases, it seems desirable to prepare compounds that inhibit its activity, which thereby inhibit downstream serine protease activity. It has been surprisingly found that the bicyclic compounds of the present invention possess potent Cathepsin C activity, high selectivity against other Cathepsins, e.g. Cathepsin K, and in general desirable pharmacokinetic properties.

DETAILED DESCRIPTION OF THE INVENTION

A compound of formula 1

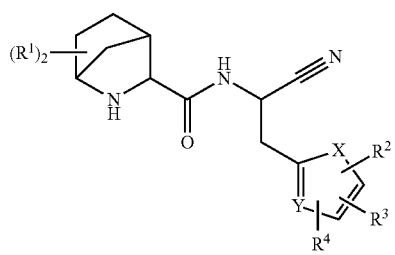

wherein
X is selected from among S and O; preferably S;
Y is selected from among N or CH, preferably CH;
$R^1$ is independently selected from among H, $C_{1-6}$-alkyl-, halogen, HO—, $C_{1-6}$-alkyl-O—, $H_2N$—, $C_{1-6}$-alkyl-HN—, $(C_{1-6}$-alkyl$)_2$N— and $C_{1-6}$-alkyl-C(O)HN—;
or two $R^1$ are together $C_{1-4}$-alkylene;
$R^2$ is selected from among
$R^{2.1}$;
aryl-; optionally substituted with one, two or three residues independently selected from $R^{2.1}$; optionally substituted with one $R^{2.3}$;
$C_{5-10}$-heteroaryl-; containing one, two, three or four heteroatoms independently selected from among S, S(O), $S(O)_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$;

$C_{5-10}$-heterocyclyl-; containing one, two, three or four heteroatoms independently selected from among S, S(O), S(O)$_2$, O and N, wherein the ring is fully or partially saturated, wherein carbon atoms of the ring are optionally and independently from each other substituted with one, two or three or four $R^{2.1}$; wherein nitrogen atoms of the ring are optionally and independently from each other substituted with one, two or three $R^{2.2}$; wherein a carbon atom of the ring is optionally substituted with one $R^{2.3}$ or one $R^{2.5}$; a nitrogen atom of the ring is optionally substituted with one $R^{2.4}$ or $R^2$ and $R^4$ are together with two adjacent carbon atoms of the heteroaryl ring a 5- or 6-membered aryl or heteroaryl, containing one, two or three heteroatoms independently selected from among S, S(O), S(O)$_2$, O or N, wherein carbon atoms of the ring are optionally and independently from each other substituted with one, two or three $R^{2.1}$; wherein nitrogen atoms of the ring are optionally and independently from each other substituted with one, two or three $R^{2.2}$;

$R^{2.1}$ is independently selected from among H, halogen, NC—, O═, HO—, H-A-, H-A-$C_{1-6}$-alkylene-, $R^{2.1.1}$-A-, $C_{1-6}$-alkyl-A-, $C_{3-8}$-cycloalkyl-A-, $C_{1-6}$-haloalkyl-A-, $R^{2.1.1}$—$C_{1-6}$-alkylene-A-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$—$C_{1-6}$-alkylene-A-$C_{1-6}$-alkylene-, $R^{2.1.1}$-A-$C_{1-6}$-alkylene-, HO—$C_{1-6}$-alkylene-A-, HO—$C_{1-6}$-alkylene-A-$C_{1-6}$-alkylene-, $C_{1-6}$-alkyl-O—$C_{1-6}$-alkylene-A- and $C_{1-6}$-alkyl-O—$C_{1-6}$-alkylene-A-$C_{1-6}$-alkylene- $R^{2.1.1}$ is independently selected from among
  aryl-; optionally substituted independently from each other with one, two or three $R^{2.1.1.1}$;
  $C_{5-10}$-heteroaryl-; containing one, two, three or four heteroatoms independently selected from among S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
  $C_{5-10}$-heterocyclyl-; containing one, two, three or four heteroatoms independently selected from among S, S(O), S(O)$_2$, O and N, wherein the ring is fully or partially saturated, wherein carbon atoms of the ring are optionally and independently from each other substituted with one, two or three or four $R^{2.1.1.1}$; wherein nitrogen atoms of the ring are optionally and independently from each other substituted with one, two or three $R^{2.1.1.2}$;
  $R^{2.1.1.1}$ is independently selected from among halogen, HO—, O═, $C_{1-6}$-alkyl-, $C_{1-6}$-alkyl-O—, $C_{1-6}$-haloalkyl-, $C_{1-6}$-haloalkyl-O— and $C_{3-8}$-cycloalkyl-;
  $R^{2.1.1.2}$ is independently selected from among O═, $C_{1-6}$-alkyl-, $C_{1-6}$-haloalkyl-; $C_{3-8}$-cycloalkyl-, $C_{1-6}$-alkyl-O—$C_{1-6}$-alkyl-, H(O)C—, $C_{1-6}$-alkyl-(O)C—, tetrahydrofuranylmethyl- and tetrahydropyranylmethyl-;

$R^{2.2}$ is independently selected from among H-A-$C_{1-6}$-alkylene-, $C_{3-8}$-cycloalkyl-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$-A-$C_{1-6}$-alkylene-, $C_{1-6}$-alkyl-S(O)$_2$— and $C_{1-6}$-alkyl-C(O)—, $R^{2.1.1}$-A-;

$R^{2.3}$ and $R^4$ are together selected from
among —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, $R^{2.3}$,
$R^{2.3}$, —C($R^{2.3.2}$)═C($R^{2.3.2}$)—, —C═N—, —N═C—, —C($R^{2.3.2}$)$_2$—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-;
  $R^{2.3.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;
  $R^{2.3.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4}$ and $R^4$ are together selected from
among —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)═C($R^{2.4.2}$)—, —C═N—, —N═C—, —C($R^{2.4.2}$)$_2$N($R^{2.4.1}$)—, —N($R^{2.4.1}$)C($R^{2.4.2}$)$_2$—, —$C_{1-4}$-alkylene-; and
  $R^{2.4.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;
  $R^{2.4.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.5}$ and $R^4$ are together selected from among —C($R^{2.5.1}$)═, ═C($R^{2.5.1}$)— and —N═; and
  $R^{2.5.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene-, ($C_{1-4}$-alkyl)$_2$N—$C_{1-4}$-alkylene-;

$R^3$ is H or F;

$R^4$ is independently selected from among H, F, Cl, Br, phenyl-$H_2C$—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, ($C_{1-6}$-alkyl)$_2$-HN—$C_{1-4}$-alkylene-; preferably F, Cl, Br, phenyl-$H_2C$—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, $C_{1-6}$-alkyl-HN—$C_{1-4}$-alkylene- and ($C_{1-6}$-alkyl)$_2$-HN—$C_{1-4}$-alkylene-;

A is a bond or independently selected from
among —O—, —S—, —N($R^5$)—, —C(O)N($R^5$)—, —N($R^5$)C(O)—, —S(O)$_2$N($R^5$)—, —N($R^5$)S(O)$_2$—, —S(O)(═N$R^5$)—N($R^5$)—, —N($R^5$)(N$R^5$═)S(O)—, —S(═N$R^5$)$_2$—N($R^5$)—, —N($R^5$)(N$R^5$═)$_2$S—, —C($R^5$)═C($R^5$)—, —C≡C—, —C(O)O—, —OC(O)—, —C(O)—, —S(O)—, —S(O)$_2$—, —S(═N$R^5$)—, —S(O)(═N$R^5$)—, —S(═N$R^5$)$_2$—, —($R^5$)(O)S═N—, —($R^5$N═)(O)S— and —N═(O)($R^5$)S—;

$R^5$ is independently selected from among H, $C_{1-6}$-alkyl- and NC—;

or a salt thereof.

PREFERRED EMBODIMENTS

Preferred are the above compounds of formula 1, wherein $R^1$ is $R^{1.a}$ and $R^{1.a}$ is independently selected from among H, $C_{1-4}$-alkyl-, F, and HO—.

Preferred are the above compounds of formula 1, wherein $R^1$ is $R^{1.b}$ and $R^{1.b}$ is H.

Preferred are the above compounds of formula 1, wherein $R^1$ is $R^{1.c}$ and two $R^{1.c}$ are together —$CH_2$—.

Preferred are the above compounds of formula 1, wherein $R^2$ is $R^{2.a}$ and $R^{2.a}$ is $R^{2.1}$.

Preferred are the above compounds of formula 1, wherein $R^2$ is $R^{2.b}$ and $R^{2.b}$ is $R^{2.1.a}$.

Preferred are the above compounds of formula 1, wherein $R^2$ is $R^{2.c}$ and $R^{2.c}$ is aryl-; optionally substituted with one, two or three residues independently selected from $R^{2.1}$; optionally substituted with one $R^{2.3}$.

Preferred are the above compounds of formula 1, wherein $R^2$ is $R^{2.d}$ and $R^{2.d}$ is phenyl; optionally substituted with one, two or three residues independently selected from $R^{2.1}$; optionally substituted with one $R^{2.3}$.

Preferred are the above compounds of formula 1, wherein $R^2$ is $R^{2.e}$ and $R^{2.e}$ is $C_{5\ or\ 6}$-heteroaryl-, containing one, two, three or four heteroatoms independently selected from among S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.f}$ and $R^{2.f}$ is bicyclic $C_{7-10}$-heteroaryl-, each containing one, two, three or four heteroatoms independently selected from S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.g}$ and $R^{2.g}$ is selected from

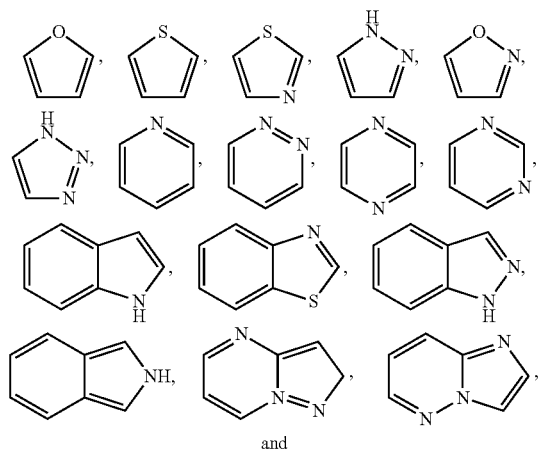

and wherein carbon atoms of the ring are optionally and independently from each other substituted with one, two or three $R^{2.1}$, wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.h}$ and $R^{2.h}$ is selected from pyrazole, thiophene and furane, wherein carbon atoms of the ring are optionally and independently from each other substituted with one, two or three $R^{2.1}$, wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.i}$ and $R^{2.i}$ is selected from $C_6$-heterocyclyl- and $C_{7-10}$-heterocyclyl-, each containing one, two, three or four heteroatoms independently selected from among S, O and N and the ring is fully or partially saturated, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.j}$ and $R^{2.j}$ is selected from among

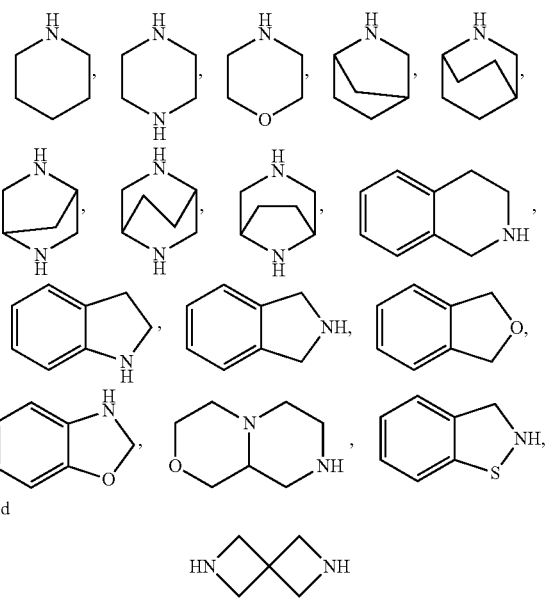

wherein carbon atoms of the ring are optionally and independently from each other substituted with one, two or three $R^{2.1}$, wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.k}$ and $R^{2.k}$ is selected from among

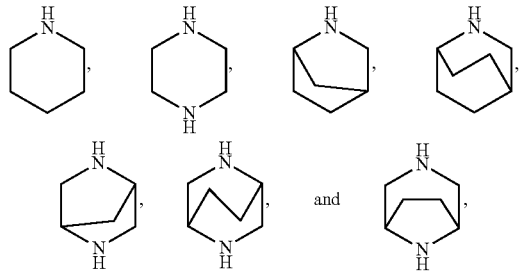

wherein carbon atoms of the ring are optionally and independently from each other substituted with one, two or three $R^{2.1}$, wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.l}$ and $R^{2.l}$ is selected from among

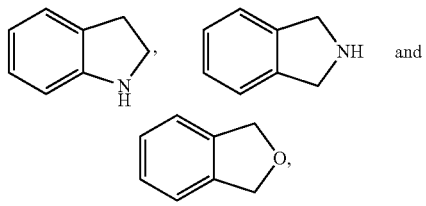

wherein carbon atoms of the ring are optionally and independently from each other substituted with one, two, three or four $R^{2.1}$, wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.m}$ and $R^{2.m}$ is together with $R^4$ and two adjacent carbon atoms of the heteroaryl ring a 5- or 6-membered aryl or heteroaryl, containing one, two or three heteroatoms independently selected from among S, S(O), S(O)$_2$, O and N, preferably pyrazole and naphtene, wherein carbon atoms of the ring are optionally and is independently from each other substituted with one, two or three $R^{2.1}$, wherein possibly available nitrogen atoms of the ring are optionally and independently from each other substituted with one, two or three $R^{2.2}$.

Preferred are the above compounds of formula 1, wherein $R^2$ is $R^{2.n}$ and $R^{2.n}$ is from aryl-, pyrazole, thiophene and furane; wherein carbon atoms of the ring are optionally and independently from each other substituted with one, two, three or four $R^{2.1}$, wherein possibly available nitrogen atoms of the ring are optionally and independently substituted with $R^{2.2}$; wherein a carbon atom of the ring is optionally substituted with one $R^{2.3}$; a nitrogen atom of the ring is optionally substituted with one $R^{2.4}$; or $R^{2.n}$ is selected from among

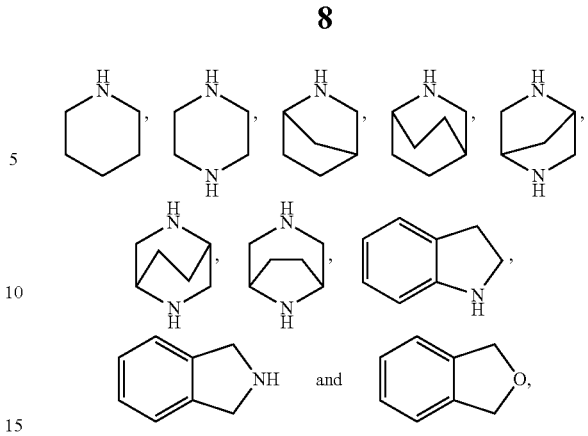

wherein carbon atoms of the ring are optionally and independently from each other substituted with one, two, three or four $R^{2.1}$, wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.o}$ and $R^{2.o}$ is selected from among aryl-, pyrazole, thiophene and furane; wherein carbon atoms of the ring are optionally and independently from each other substituted with one, two, three or four $R^{2.1}$, wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.p}$ and $R^{2.p}$ is selected from among

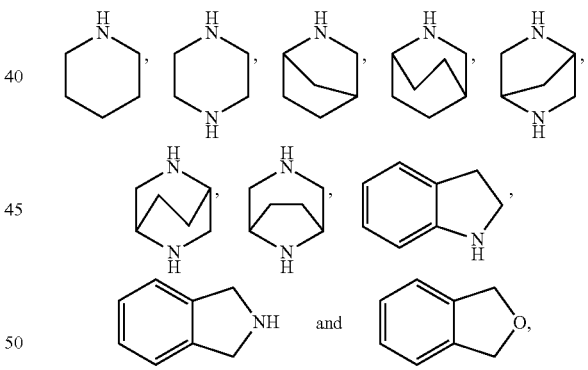

wherein carbon atoms of the ring are optionally and independently from each other substituted with one, two, three or four $R^{2.1}$, wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$ haloalkyl-A-, $R^{2.1.1}$-$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene- A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-.

Preferred are the above compounds of formula 1, wherein $R^{2.1.1}$ is $R^{2.1.1.a}$ and $R^{2.1.1.a}$ is selected from among aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;

$C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.12}$; and $R^{2.1.1.1}$ is independently selected from among halogen, HO—, O=, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl.

Preferred are the above compounds of formula 1, wherein $R^{2.1.1}$ is $R^{2.1.1.b}$ and $R^{2.1.1.b}$ is phenyl or selected from among

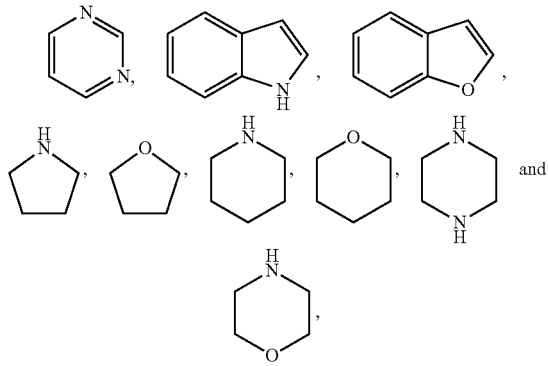

wherein carbon atoms of the ring are optionally and independently from each other substituted with one, two or three $R^{2.1.1.1}$, wherein possibly available nitrogen atoms of the ring are optionally and independently from each other substituted with $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl.

Preferred are the above compounds of formula 1, wherein $R^{2.1.1}$ is $R^{2.1.1.c}$ and $R^{2.1.1.c}$ is phenyl or selected from among

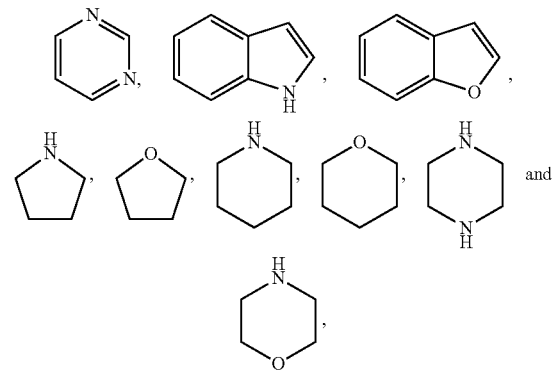

wherein carbon atoms of the ring are optionally and independently from each other substituted with one, two or three $R^{2.1.1.1}$, wherein possibly available nitrogen atoms of the ring are optionally and independently from each other substituted with $R^{2.1.1.2}$; and $R^{2.1.1.1}$ is independently selected from among F, Cl, Me, MeO— and cyclopropyl-; and $R^{2.1.1.2}$ is independently selected from among Me, tetrahydrofuranylmethyl- and tetrahydropyranylmethyl.

Preferred are the above compounds of formula 1, wherein $R^{2.1.2}$ is $R^{2.1.2.a}$ and $R^{2.1.2.a}$ is selected from among H, NC—, $C_{1-4}$-alkyl-, $C_{1-4}$-haloalkyl-, $C_{3-6}$-cycloalkyl-, HO—$C_{1-4}$-alkylene- and ($C_{1-4}$-alkyl)-O—$C_{1-4}$-alkylene-.

Preferred are the above compounds of formula 1, wherein $R^{2.1.2}$ is $R^{2.1.2.b}$ and $R^{2.1.2.b}$ is selected from among H, $C_{1-4}$-alkyl- and $C_{3-6}$-cycloalkyl-;

Preferred are the above compounds of formula 1, wherein $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$— and $C_{1-4}$-alkyl-C(O)—, $R^{2.1.1}$-A-;

Preferred are the above compounds of formula 1, wherein $R^{2.2}$ is $R^{2.2.b}$ and $R^{2.2.b}$ is together with $R^4$ selected from among —C(O)—, —S(O)—, —S(O)$_2$—, —C($R^{2.1.2}$)— and —$C_{1-4}$-alkylene-;

Preferred are the above compounds of formula 1, wherein $R^{2.3}$ is together with $R^4$ a group $R^{2.3.a}$ and $R^{2.3.a}$ is selected from among —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, —C($R^{2.3.2}$)=C($R^{2.3.2}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-; and $R^{2.3.1}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.3.2}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-.

Preferred are the above compounds of formula 1, wherein $R^{2.4}$ is together with $R^4$ a group $R^{2.4.a}$ and $R^{2.4.a}$ is selected from among —N(R$^{2.4.1}$)—, —C(O)N(R$^{2.4.1}$)—, —N(R$^{2.4.1}$)C(O)—, —S(O)$_2$N(R$^{2.4.1}$)—, —N(R$^{2.4.1}$)S(O)$_2$—, —C(O)—, —S(O)—, —S(O)$_2$—, —C(R$^{2.4.2}$)=C(R$^{2.4.2}$)—, —C≡N—, —N≡C—, —C(R$^{2.4.2}$)$_2$N(R$^{2.4.1}$)—, —N(R$^{2.4.1}$)C(R$^{2.4.2}$)$_2$— and —C$_{1-4}$-alkylene-; and R$^{2.4.1}$ is independently selected from among H, C$_{1-4}$-alkyl-, C$_{1-4}$-haloalkyl-, C$_{3-6}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)$_2$N—C$_{1-4}$-alkylene-;

R$^{2.4.2}$ is independently selected from among H, C$_{1-4}$-alkyl-, C$_{1-4}$-haloalkyl-, C$_{3-6}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)N—C$_{1-4}$-alkylene-.

Preferred are the above compounds of formula 1, wherein R$^{2.5}$ is together with R$^4$ a group R$^{2.5.a}$ and R$^{2.5.a}$ is selected from among —C(R$^{2.5.1}$)=, =C(R$^{2.5.1}$)— and —N=; and R$^{2.5.1}$ is independently selected from among H, C$_{1-4}$-alkyl-, C$_{1-4}$-haloalkyl-, C$_{3-6}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)N—C$_{1-4}$-alkylene-.

Preferred are the above compounds of formula 1, wherein R$^2$ is selected from the Table 1R$^2$—Embodiments of the invention for R$^2$, R$^{2.1}$, R$^{2.1.1}$, R$^{2.2}$, R$^{2.3}$, R$^{2.4}$ and (if present):

TABLE 1

| E # | R$^2$ | R$^{2.1}$ | R$^{2.1.1}$ | R$^{2.2}$ | R$^{2.3-5}$ |
|---|---|---|---|---|---|
| 1 | R$^{2.a}$ | R$^{2.1}$ | R$^{2.1.1.a}$ | — | — |
| 2 | R$^{2.a}$ | R$^{2.1}$ | R$^{2.1.1.b}$ | — | — |
| 3 | R$^{2.a}$ | R$^{2.1}$ | R$^{2.1.1.c}$ | — | — |
| 4 | R$^{2.b}$ | R$^{2.1.a}$ | R$^{2.1.1.a}$ | — | — |
| 5 | R$^{2.b}$ | R$^{2.1.a}$ | R$^{2.1.1.b}$ | — | — |
| 6 | R$^{2.b}$ | R$^{2.1.a}$ | R$^{2.1.1.c}$ | — | — |
| 7 | R$^{2.c}$ | R$^{2.1.a}$ | R$^{2.1.1.a}$ | — | — |
| 8 | R$^{2.c}$ | R$^{2.1.a}$ | R$^{2.1.1.b}$ | — | — |
| 9 | R$^{2.c}$ | R$^{2.1.a}$ | R$^{2.1.1.c}$ | — | — |
| 10 | R$^{2.c}$ | R$^{2.1.a}$ | R$^{2.1.1.c}$ | — | R$^{2.3.a}$ |
| 11 | R$^{2.c}$ | R$^{2.1.a}$ | R$^{2.1.1.c}$ | — | R$^{2.4.a}$ |
| 12 | R$^{2.c}$ | R$^{2.1.a}$ | R$^{2.1.1.c}$ | — | R$^{2.5.a}$ |
| 13 | R$^{2.d}$ | R$^{2.1.a}$ | R$^{2.1.1.a}$ | — | — |
| 14 | R$^{2.d}$ | R$^{2.1.a}$ | R$^{2.1.1.b}$ | — | — |
| 15 | R$^{2.d}$ | R$^{2.1.a}$ | R$^{2.1.1.c}$ | — | — |
| 16 | R$^{2.d}$ | R$^{2.1.a}$ | R$^{2.1.1.c}$ | — | R$^{2.3.a}$ |
| 17 | R$^{2.d}$ | R$^{2.1.a}$ | R$^{2.1.1.c}$ | — | R$^{2.4.a}$ |
| 18 | R$^{2.d}$ | R$^{2.1.a}$ | R$^{2.1.1.c}$ | — | R$^{2.5.a}$ |
| 19 | R$^{2.e}$ | R$^{2.1.a}$ | R$^{2.1.1.a}$ | R$^{2.2.a}$ | — |
| 20 | R$^{2.e}$ | R$^{2.1.a}$ | R$^{2.1.1.b}$ | R$^{2.2.a}$ | — |
| 21 | R$^{2.e}$ | R$^{2.1.a}$ | R$^{2.1.1.c}$ | R$^{2.2.a}$ | — |
| 22 | R$^{2.f}$ | R$^{2.1.a}$ | R$^{2.1.1.a}$ | R$^{2.2.a}$ | — |
| 23 | R$^{2.f}$ | R$^{2.1.a}$ | R$^{2.1.1.b}$ | R$^{2.2.a}$ | — |
| 24 | R$^{2.f}$ | R$^{2.1.a}$ | R$^{2.1.1.c}$ | R$^{2.2.a}$ | — |
| 25 | R$^{2.g}$ | R$^{2.1.a}$ | R$^{2.1.1.a}$ | R$^{2.2.a}$ | — |
| 26 | R$^{2.g}$ | R$^{2.1.a}$ | R$^{2.1.1.b}$ | R$^{2.2.a}$ | — |
| 27 | R$^{2.g}$ | R$^{2.1.a}$ | R$^{2.1.1.c}$ | R$^{2.2.a}$ | — |
| 28 | R$^{2.h}$ | R$^{2.1.a}$ | R$^{2.1.1.a}$ | R$^{2.2.a}$ | — |
| 29 | R$^{2.h}$ | R$^{2.1.a}$ | R$^{2.1.1.b}$ | R$^{2.2.a}$ | — |
| 30 | R$^{2.h}$ | R$^{2.1.a}$ | R$^{2.1.1.c}$ | R$^{2.2.a}$ | — |
| 31 | R$^{2.e}$ | R$^{2.1.a}$ | R$^{2.1.1.c}$ | — | R$^{2.3.a}$ |
| 32 | R$^{2.e}$ | R$^{2.1.a}$ | R$^{2.1.1.c}$ | — | R$^{2.4.a}$ |
| 33 | R$^{2.e}$ | R$^{2.1.a}$ | R$^{2.1.1.c}$ | — | R$^{2.5.a}$ |
| 34 | R$^{2.g}$ | R$^{2.1.a}$ | R$^{2.1.1.c}$ | — | R$^{2.3.a}$ |
| 35 | R$^{2.g}$ | R$^{2.1.a}$ | R$^{2.1.1.c}$ | — | R$^{2.4.a}$ |
| 36 | R$^{2.g}$ | R$^{2.1.a}$ | R$^{2.1.1.c}$ | — | R$^{2.5.a}$ |
| 37 | R$^{2.h}$ | R$^{2.1.a}$ | R$^{2.1.1.c}$ | — | R$^{2.3.a}$ |
| 38 | R$^{2.h}$ | R$^{2.1.a}$ | R$^{2.1.1.c}$ | — | R$^{2.4.a}$ |
| 39 | R$^{2.h}$ | R$^{2.1.a}$ | R$^{2.1.1.c}$ | — | R$^{2.5.a}$ |
| 40 | R$^{2.i}$ | R$^{2.1.a}$ | R$^{2.1.1.a}$ | R$^{2.2.a}$ | — |
| 41 | R$^{2.i}$ | R$^{2.1.a}$ | R$^{2.1.1.b}$ | R$^{2.2.a}$ | — |
| 42 | R$^{2.i}$ | R$^{2.1.a}$ | R$^{2.1.1.c}$ | R$^{2.2.a}$ | — |
| 43 | R$^{2.j}$ | R$^{2.1.a}$ | R$^{2.1.1.a}$ | R$^{2.2.a}$ | — |
| 44 | R$^{2.j}$ | R$^{2.1.a}$ | R$^{2.1.1.b}$ | R$^{2.2.a}$ | — |
| 45 | R$^{2.j}$ | R$^{2.1.a}$ | R$^{2.1.1.c}$ | R$^{2.2.a}$ | — |
| 46 | R$^{2.k}$ | R$^{2.1.a}$ | R$^{2.1.1.a}$ | R$^{2.2.a}$ | — |
| 47 | R$^{2.k}$ | R$^{2.1.a}$ | R$^{2.1.1.b}$ | R$^{2.2.a}$ | — |
| 48 | R$^{2.k}$ | R$^{2.1.a}$ | R$^{2.1.1.c}$ | R$^{2.2.a}$ | — |
| 49 | R$^{2.l}$ | R$^{2.1.a}$ | R$^{2.1.1.a}$ | R$^{2.2.a}$ | — |
| 50 | R$^{2.l}$ | R$^{2.1.a}$ | R$^{2.1.1.b}$ | R$^{2.2.a}$ | — |
| 51 | R$^{2.l}$ | R$^{2.1.a}$ | R$^{2.1.1.c}$ | R$^{2.2.a}$ | — |

For a better understanding of the Table 1R$^2$—Embodiments of the invention example (E#) 21, can also be read as a group R$^2$, wherein R$^2$ is R$^{2.e}$ and R$^{2.e}$ is C$_{5\ or\ 6}$-heteroaryl-, containing one, two, three or four heteroatoms independently selected from among S, S(O), S(O)$_2$, O and N, wherein carbon atoms of the ring are optionally and independently from each other substituted with one, two or three R$^{2.1}$; wherein nitrogen atoms of the ring are optionally and independently from each other substituted with one, two or three R$^{2.2}$; and R$^{2.1}$ is R$^{2.1.a}$ and R$^{2.1.a}$ is selected from among H, halogen, NC—, O=, HO—, H-A-, H-A-C$_{1-4}$-alkylene-, R$^{2.1.1}$-A-, C$_{1-4}$-alkyl-A-, C$_{3-6}$-cycloalkyl-A-, C$_{1-4}$-haloalkyl-A-, R$^{2.1.1}$—C$_{1-4}$-alkylene-A-, C$_{1-4}$-alkyl-A-C$_{1-4}$-alkylene-, —C$_{3-6}$-cycloalkyl-A-C$_{1-4}$-alkylene-, C$_{1-4}$-haloalkyl-A-C$_{1-4}$-alkylene-, R$^{2.1.1}$—C$_{1-4}$-alkylene-A-C$_{1-4}$-alkylene-, R$^{2.1.1}$-A-C$_{1-4}$-alkylene-, HO—C$_{1-4}$-alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-; and R$^{2.1.1}$ is R$^{2.1.1.c}$ and R$^{2.1.1.c}$ is phenyl or selected from among

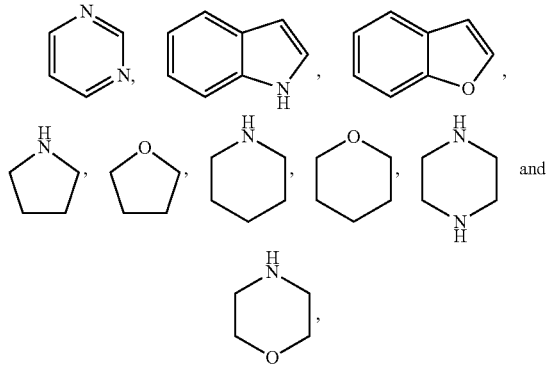

wherein carbon atoms of the ring are optionally and independently from each other substituted with one, two or three R$^{2.1.1.1}$, wherein possibly available nitrogen atoms of the ring are optionally and independently from each other substituted with R$^{2.1.1.2}$; and R$^{2.1.1.1}$ is independently selected from among F, Cl, Me, MeO— and cyclopropyl-; and R$^{2.1.1.2}$ is independently selected from among Me, tetrahydrofuranylmethyl- and tetrahydropyranylmethyl; and R$^{2.2}$ is R$^{2.2.a}$ and R$^{2.2.a}$ is independently selected from among H-A-C$_{1-4}$-alkylene-, C$_{3-6}$-cycloalkyl-, C$_{1-4}$-alkyl-A-C$_{1-4}$-alkylene-, C$_{3-6}$-cycloalkyl-A-C$_{1-4}$-alkylene-, C$_{1-4}$-haloalkyl-A-C$_{1-4}$-alkylene-, R$^{2.1.1}$-A-C$_{1-4}$-alkylene-, C$_{1-4}$-alkyl-S(O)$_2$—, C$_{1-4}$-alkyl-C(O)— and R$^{2.1.1}$-A-.

Preferred are the above compounds of formula 1, wherein $R^3$ is $R^{3.a}$ and $R^{3.a}$ is H.

Preferred are the above compounds of formula 1, wherein $R^3$ is $R^{3.b}$ and $R^{3.b}$ is F.

Preferred are the above compounds of formula 1, wherein $R^4$ is $R^{4.a}$ and $R^{4.a}$ is H, F, Cl, Br, phenyl-$H_2C$—O—, HO—, $C_{1-4}$-alkyl-, $C_{1-4}$-haloalkyl-, $C_{3-6}$-cycloalkyl-, $C_{1-4}$-alkyl-O— and $C_{1-4}$-haloalkyl-O—.

Preferred are the above compounds of formula 1, wherein $R^4$ is $R^{4.b}$ and $R^{4.b}$ is H or F.

Preferred are the above compounds of formula 1, wherein $R^4$ is $R^{4.c}$ and $R^{4.c}$ is F; preferably in is ortho position.

Preferred are the above compounds of formula 1, wherein A is $A^a$ and $A^a$ is a bond or independently selected from among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$—, —($R^5$)(O)S=N—, —($R^5$N=)(O)S— and —N=(O)($R^5$)S— and $R^5$ is $R^{5.a}$ and $R^{5.a}$ is in dependently selected from among H, $C_{1-4}$-alkyl-, NC—.

Preferred are the above compounds of formula 1, wherein A is $A^b$ and $A^b$ is a bond.

Preferred are the above compounds of formula 1, wherein X is $X^a$ and $X^a$ is S or O; preferably S; and Y is $Y^a$ and $Y^a$ is CH;

Preferred are the above compounds of formula 1, wherein X is $X^b$ and $X^b$ is S; and Y is $Y^b$ and $Y^b$ is N;

Preferred are the above compounds of formula 1, wherein $R^2$ is $R^{2q}$ and $R^{2q}$ is selected from among formulas (b1) to (g1),

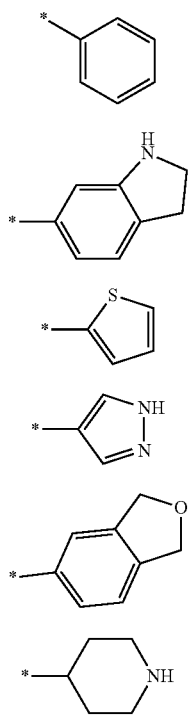

(b1)

(c1)

(d1)

(e1)

(f1)

(g1)

wherein carbon atoms of the ring are optionally and independently from each other substituted with one, two or three $R^{2.1}$; wherein nitrogen atoms of the ring are optionally and independently from each other substituted with one, two or three $R^{2.2}$, wherein
$R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ selected from among
aryl-, optionally substituted independently from each other with one, two or three is residues independently selected from $R^{2.1.1.1}$;
$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
$C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl- and $C_{1-4}$-haloalkyl-O—, $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

Particularly preferred are the above compounds of formula 1, wherein $R^2$ is selected $R^{2.r}$ and $R^{2.r}$ is selected from among formulas (b1) to (g1),
wherein carbon atoms of the ring are optionally and independently from each other substituted with one or two F, —CN, —SO$_2$Me, =O, —COMe and —SO2-pyrazinyl-Me, wherein nitrogen atoms of the is ring are optionally and independently from each other substituted with Me, Et and —CH$_2$-tetrahydropyranyl.

Preferred are the above compounds of formula 1, wherein $R^3$ is H.

Preferred are the above compounds of formula 1, wherein $R^3$ is F.

Preferred are the above compounds of formula 1, wherein $R^4$ is $R^{4.d}$, wherein $R^{4.d}$ is selected from among H, F, Cl and Br.

Particularly preferred are the above compounds of formula 1, wherein $R^4$ is $R^{4.e}$, wherein $R^{4.d}$ is H or Br, preferably H.

Particularly preferred are the above compounds of formula 1, wherein $R^4$ is $R^{4.e}$, wherein $R^{4.d}$ is H or F, Preferred are the above compounds of formula 1, wherein $R^2$ and $R^4$ are together with two adjacent carbon atoms of the heteroaryl ring a 5- or 6-membered aryl, preferably phenyl ring, wherein the 5- or 6-membered aryl is optionally substituted by one or two, preferably one, residue selected from among
halogen, —CN,
$C_{5-10}$-heteroaryl-, containing one, two, three or four heteroatoms selected independently from among S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and
$C_{5-10}$-heterocyclyl-, containing one, two, three or four heteroatoms selected independently from S, S(O), S(O)$_2$, O or N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and
$R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O—, $C_{3-6}$-cycloalkyl-; and
$R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, is tetrahydrofuranylmethyl- and tetrahydropyranylmethyl.

Particularly preferred are the above compounds of formula 1, wherein
$R^2$ and $R^4$ are together with two adjacent carbon atoms of the heteroaryl ring a 5- or 6-membered aryl, preferably phenyl ring, wherein the 5- or 6-membered aryl is optionally substituted by one or two, preferably one, residue selected from among
Br, F, —CN, phenyl and a group of formula (a1).

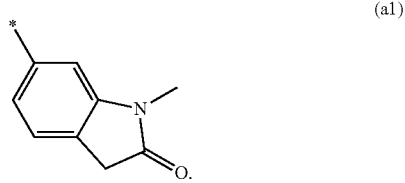 [SMILES: *c1ccc2c(c1)N(C)C(=O)C2]

(a1)

Preferred is a compound of formula 1, wherein
$R^1$ is H,
$R^2$ is $R^{2.q}$ or $R^{2.r}$, $R^3$ is H or F, and
$R^4$ is $R^{4.d}$ or $R^{4.e}$,
or salts thereof.
Preferred is a compound of formula 1, wherein
$R^1$ is H,
$R^3$ is H or F, and
$R^2$ and $R^4$ are together with two adjacent carbon atoms of the heteroaryl ring a 5- or 6-membered aryl, preferably phenyl ring, wherein
the 5- or 6-membered aryl is optionally substituted by one or two, preferably one, residue selected from among
halogen, —CN,
$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and
$R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and
$R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl,
or salts thereof.
Preferred is a compound of formula 1, wherein
$R^1$ is H,
$R^3$ is H or F, and
$R^2$ and $R^4$ are together with two adjacent carbon atoms of the heteroaryl ring a 5- or 6-membered aryl, preferably phenyl ring, wherein the 5- or 6-membered aryl is optionally substituted by one or two, preferably one, residue selected from among
Br, F, —CN, phenyl and a group of formula (a1).

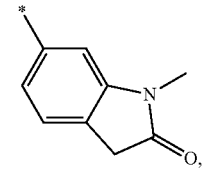

(a1)

or salts thereof.
Preferred is a compound of formula 1, wherein
X is selected from among S and O;
Y is selected from among N and CH;
$R^1$ is independently selected from among H, $C_{1-4}$-alkyl-, halogen, HO—, $C_{1-4}$-alkyl-O—, $H_2N$—, $C_{1-6}$-alkyl-HN—, $(C_{1-6}$-alkyl)$_2$N— and $C_{1-6}$-alkyl-C(O)HN—;
or two $R^1$ are together $C_{1-4}$-alkylene;
$R^2$ is selected of the examples of the Table 1$R^2$—Embodiments of the invention; preferably is examples (E#) 7-51, preferably one of the groups selected from among 7, 8, 9, 10, 11, 12, 13, 14, 15, 16, 17, 18 or 19, 20, 21, 22, 23, 24, 25, 26, 27, 28, 29, 30, 31, 32, 33, 34, 35, 36, 37, 38, 39 or 40, 41, 42, 43, 44, 45, 45, 46, 47, 48, 49, 50 and 51;
$R^3$ is H or F;
$R^4$ is independently selected from among H, F, Cl, Br, phenyl-$H_2C$—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, $(C_{1-6}$-alkyl)$_2$-HN—, $C_{1-6}$-alkyl-HN—$C_{1-4}$-alkylene- and $(C_{1-6}$-alkyl)$_2$-HN—$C_{1-4}$-alkylene-;
A is a bond or independently selected from
among —O—, —S—, —N(R$^5$)—, —C(O)N(R$^5$)—, —N(R$^5$)C(O)—, —S(O)$_2$N(R$^5$)—, —N(R$^5$)S(O)$_2$—, —S(O)(=NR$^5$)—N(R$^5$)—, —N(R$^5$)(NR$^5$=) S(O)—, —S(=NR$^5$)$_2$—N(R$^5$)—, —N(R$^5$)(NR$^5$=)$_2$S—, —C(R$^5$)=C(R$^5$)—, —C≡C—, —C(O)O—, —OC(O)—, —C(O)—, —S(O)—,
S(O)$_2$—, —S(=NR$^5$)—, —S(O)(=NR$^5$)—, —S(=NR$^5$)$_2$—, —(R$^5$)(O)S=N—, —(R$^5$N=)(O)S— and —N=(O)(R$^5$)S—;

$R^5$ is independently selected from among H, $C_{1-6}$-alkyl- and NC—;
or a salt thereof.

Preferred is a compound of formula 1, wherein

X is selected from among S and O;
Y is selected from among N and CH;
$R^1$ is $R^{1.a}$ and $R^{1.a}$ is independently selected from among H, $C_{1-4}$-alkyl-, F and HO—.
or two $R^1$ are together $C_{1-4}$-alkylene;
$R^2$ is selected of the examples of the Table 1$R^2$—Embodiments of the invention; preferably is examples (E#) 7-51, preferably one of the groups selected from among 7, 8, 9, 10, 11, 12, 13, 14, 15, 16, 17, 18 or 19, 20, 21, 22, 23, 24, 25, 26, 27, 28, 29, 30, 31, 32, 33, 34, 35, 36, 37, 38, 39 or 40, 41, 42, 43, 44, 45, 45, 46, 47, 48, 49, 50, 51;
$R^3$ is H or F;
$R^4$ is $R^{4.a}$ and $R^{4.a}$ is H, F, Cl, Br, phenyl-H$_2$C—O—, HO—, $C_{1-4}$-alkyl-, $C_{1-4}$-haloalkyl-, $C_{3-6}$-cycloalkyl-, $C_{1-4}$-alkyl-O— and $C_{1-4}$-haloalkyl-O—;
A is a bond or independently selected from
among —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=) S(O)—, —S(=N$R^5$)$_2$—N($R^5$)—, —N($R^5$)(N$R^5$=)$_2$S—, —C($R^5$)=C($R^5$)—, —C≡C—, —C(O)O—, —OC(O)—, —C(O)—, —S(O)—, S(O)$_2$—, —S(=N$R^5$)—, —S(O)(=N$R^5$)—, —S(=N$R^5$)$_2$—, —($R^5$)(O)S=N—, —($R^5$N=)(O)S— and —N=(O)($R^5$)S—;
$R^5$ is independently selected from among H, $C_{1-6}$-alkyl- and NC—;
or a salt thereof.

Preferred is a compound of formula 1, wherein

X is selected from among S and O;
Y is selected from among N and CH;
$R^1$ is $R^{1.a}$ and $R^{1.a}$ is independently selected from among H, $C_{1-4}$-alkyl-, F and HO—.
or two $R^1$ are together $C_{1-4}$-alkylene;
$R^2$ is selected of the examples of the Table 1$R^2$—Embodiments of the invention; preferably examples (E#) 7-51, preferably one of the groups selected from among 13, 14, 15, 16, 17, 18 or 25, 26, 27, 28, 29, 30, 34, 35, 36, 37, 38, 39 or 43, 44, 45, 46, 47, 48;
$R^3$ is H or F;
$R^4$ is $R^{4a}$ and $R^{4a}$ is H, F, Cl, Br, phenyl-H$_2$C—O—, HO—, $C_{1-4}$-alkyl-, $C_{1-4}$-haloalkyl-, $C_{3-6}$-cycloalkyl-, $C_{1-4}$-alkyl-O— and, $C_{1-4}$-haloalkyl-O—;
A is $A^a$ and $A^a$ is a bond or independently selected from
among —O—, —C(O)N($R^5$)—, —N($R^5$)C(O)—, —S(O)$_2$ N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and —N=(O)($R^5$)S—;
$R^5$ is $R^{5.a}$ and $R^{5.a}$ is independently selected from among H, $C_{1-4}$-alkyl- and NC—;
or a salt thereof.

Preferred is a compound of formula 1, wherein

X is selected from among S and O;
Y is selected from among N and CH;
$R^1$ is $R^{1.b}$ and $R^{1.b}$ is H; or two $R^1$ are together —CH$_2$—;
$R^2$ is selected of the examples of the Table 1$R^2$—Embodiments of the invention; preferably examples (E#) 7-51, preferably one of the groups selected from among 13, 14, 15, 16, 17, 18 or 25, 26, 27, 28, 29, 30, 34, 35, 36, 37, 38, 39 or 43, 44, 45, 46, 47, 48;

A is $A^a$ and $A^a$ is a bond or independently selected from
among —O—, —C(O)N($R^5$)—, —N($R^5$)C(O)—, —S(O)$_2$ N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and, —N=(O)($R^5$)S—;
$R^5$ is $R^{5.a}$ and $R^{5.a}$ is independently selected from among H, $C_{1-4}$-alkyl- and NC—;
or a salt thereof.

Preferred is a compound of formula 1, wherein

X is selected from among S and O;
Y is selected from among N and CH;
$R^1$ is $R^{1.b}$ and $R^{1.b}$ is H; or two $R^1$ are together —CH$_2$—;
$R^2$ is selected of the examples of the Table 1$R^2$—Embodiments of the invention; preferably examples (E#) 7-51, preferably one of the groups selected from among 13, 14, 15, 16, 17, 18 or 25, 26, 27, 28, 29, 30, 34, 35, 36, 37, 38, 39 or 43, 44, 45, 46, 47, 48;
$R^3$ is H or F;
$R^4$ is $R^{4.b}$ and $R^{4.b}$ is H or F;
A is $A^a$ and $A^a$ is a bond or independently selected from
among —O—, —C(O)N($R^5$)—, —N($R^5$)C(O)—, —S(O)$_2$ N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and —N=(O)($R^5$)S—;
$R^5$ is $R^{5.a}$ and $R^{5.a}$ is independently selected from among H, $C_{1-4}$-alkyl- and NC—;
or a salt thereof.

Preferred is a compound of formula 1, wherein

X is selected from among S and O;
Y is selected from among N and CH;
$R^1$ is $R^{1.b}$ and $R^{1.b}$ is H; or two $R^1$ are together —CH$_2$—;
$R^2$ is selected from among
  $R^{2.1}$;
  phenyl-; optionally substituted with one or two residues independently selected from $R^{2.1}$; optionally substituted with one $R^{2.3}$;
  $C_5$-heteroaryl-; containing two or three independently selected from among S, O and N, wherein carbon atoms of the ring are optionally and independently from each other substituted with one $R^{2.1}$; wherein nitrogen atoms of the ring are optionally and is independently from each other substituted with one $R^{2.2}$;
  monocyclic $C_6$-heterocyclyl containing one or two nitrogen atoms, wherein the ring is fully or partially saturated, wherein carbon atoms of the ring are optionally and independently from each other substituted with one $R^{2.1}$; wherein nitrogen atoms of the ring are optionally and independently from each other substituted with one $R^{2.2}$;
  bicyclic $C_{9\text{ or }10}$-heterocyclyl-; containing one, two, three or four heteroatoms independently selected from among S(O)$_2$, O and N, wherein the ring is fully or partially saturated, wherein carbon atoms of the ring are optionally and independently from each other substituted with one, two or three $R^{2.1}$; wherein nitrogen atoms of the ring are optionally and independently from each other substituted with one $R^{2.2}$;
$R^{2.1}$ is independently selected from among halogen, NC—, O=, H-A-, H-A-$C_{1-4}$-alkylene-, $C_{1-4}$-alkyl-A-, $C_{3-6}$-cycloalkyl-A-, $R^{2.1.1}$—$C_{1-4}$-alkylene-A-, $C_{1-4}$-alkyl-A-$C_{1-4}$-alkylene-, HO—$C_{1-4}$-alkylene-A-$C_{1-4}$-alkylene-; preferably F, NC—, O=, H-A-, H-A-CH$_2$—, $R^{2.1.1}$-A-, H$_3$C-A-, H$_3$C—CH$_2$-A-, Cyclopropyl-A-, $R^{2.1.1}$—CH$_2$—CH$_2$-A-, $R^{2.1.1}$—CH$_2$-A-, H$_3$C-A-CH$_2$—CH$_2$— and HO—$C_4$-alkylene-A-CH$_2$—;
$R^{2.1.1}$ is independently selected from among
  phenyl-;

$C_{5 \text{ or } 6}$-heterocyclyl-; containing one or two heteroatoms independently selected from among O and N, wherein the ring is fully or partially saturated, wherein nitrogen atoms of the ring are optionally and independently from each other substituted with one $C_{1-4}$-alkyl-; preferably $H_3C—$;

$R^{2.2}$ is independently selected from among H-A-$C_{1-4}$-alkylene-, $C_{3-6}$-cycloalkyl-, $C_{1-4}$-alkyl-A-$C_{1-4}$-alkylene-, $R^{2.1.1}$-A-$C_{1-4}$-alkylene-, $C_{1-4}$-alkyl-C(O)—; preferably H-A-$CH_2$—, H-A-$CH_2$—$CH_2$—, cyclopropyl-, $H_3C$-A-$CH_2$—$CH_2$—, $R^{2.1.1}$-A-$CH_2$— and $H_3C$—C(O)—;

$R^{2.3}$ and $R^4$ are together a group selected from among —N($R^{2.3.1}$)—, —C(O)N($R^{2.3.2}$)— and —N($R^{2.3.1}$)C(O)—;

$R^{2.3.1}$ is independently selected from among H and $H_3C—$;

$R^3$ is H or F;

$R^4$ is $R^{4.b}$ and $R^{4.b}$ is H or F;

A is a bond or independently selected from among —O—, —C(O)N($R^5$)—, —N($R^5$)C(O)—, —S(O)$_2$ N($R^5$)—, —N($R^5$)S(O)$_2$—, —C(O)O—, —OC(O)—, —C(O)—, —S(O)$_2$— and —N═(O)($R^5$)S—;

$R^5$ is independently selected from among H and $C_{1-4}$-alkyl-; or a salt thereof.

Preferred are the above compounds of formula 1, in its enantiomerically pure form of formula 1'

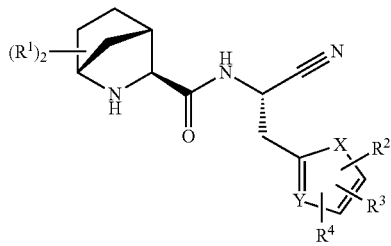

1' wherein X, Y, $R^1$, $R^2$, $R^3$ and $R^4$ have the above mentioned meaning.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, S(O), S(O)$_2$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-4}$-alkyl-" means an aryl group which is bound to a $C_{1-4}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, is particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2, 2', 2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethane-sulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term halogen generally denotes fluorine, chlorine, bromine and iodine.

The term "$C_{1-n}$-alkyl", wherein n is an integer selected from among 2, 3, 4, 5 or 6, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer selected from 2, 3, 4, 5 or 6, preferably 4 or 6, either alone or in combination with another radical, denotes an acyclic, straight or branched chain divalent alkyl radical containing from 1 to n carbon atoms. For example the term $C_{1-4}$-alkylene includes —CH$_2$—, —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

The term "$C_{3-n}$-cycloalkyl", wherein n is an integer selected from 4, 5, 6, 7 or 8, preferably 4, 5 or 6, either alone or in combination with another radical denotes a cyclic, saturated, unbranched hydrocarbon radical with 3 to 8 C atoms.

For example the term $C_{3-8}$-cycloalkyl includes cyclopropyl, cyclobutyl, cyclopentyl, cyclohexyl, cycloheptyl, cyclooctyl.

By the term "halo" added to a "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: $H_2FC-$, $HF_2C-$, $F_3C-$.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "$C_{5-10}$-heterocyclyl" means a saturated or unsaturated mono- or polycyclic-ring systems including aromatic ring system containing one or more heteroatoms independently selected from N, O or $S(O)_r$, wherein r=0, 1 or 2, consisting of 5 to 10 ring atoms wherein none of the heteroatoms is part of the aromatic ring. The term "heterocyclyl" is intended to include all the possible isomeric forms. Thus, the term "heterocyclyl" includes the following exemplary structures which are not depicted as radicals as each form may be attached through a covalent (single or double) bond to any atom so long as appropriate valences are maintained:

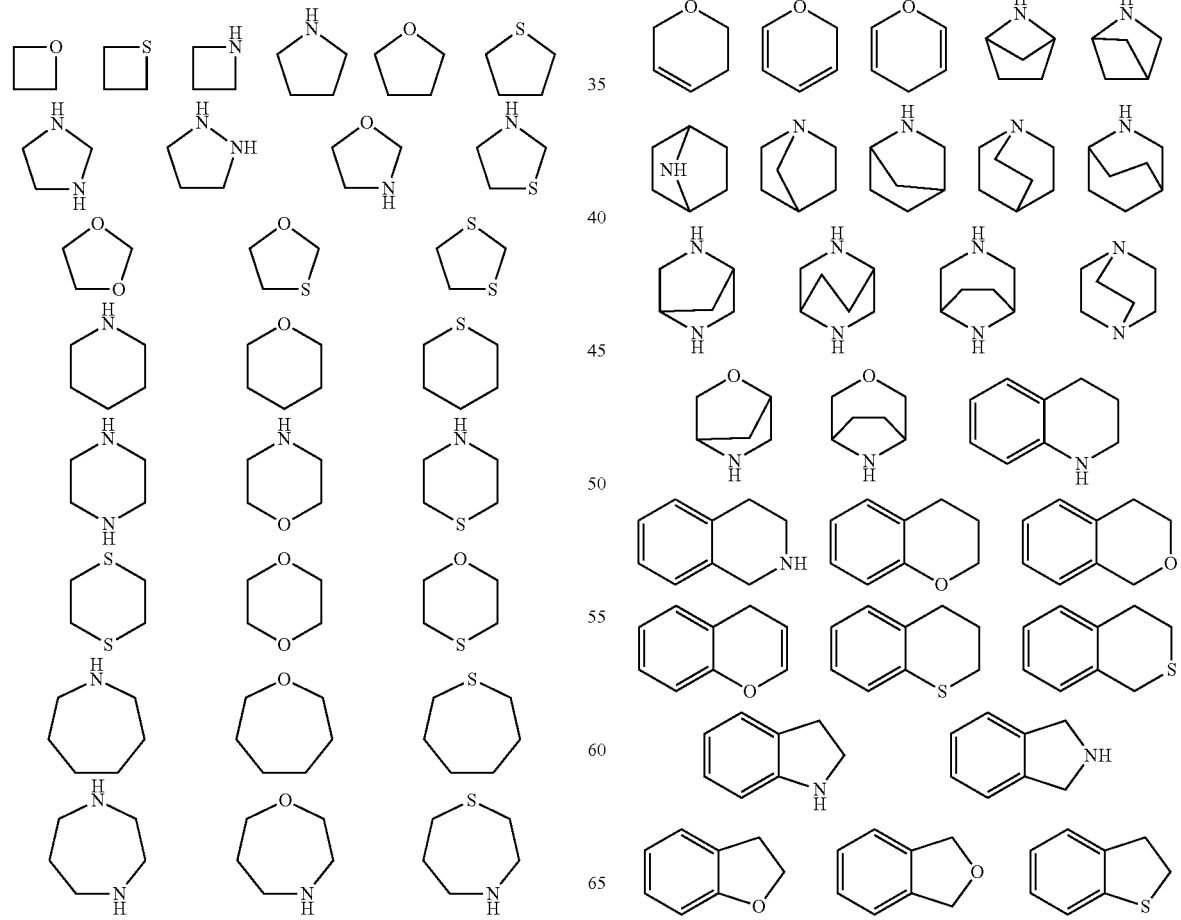

-continued

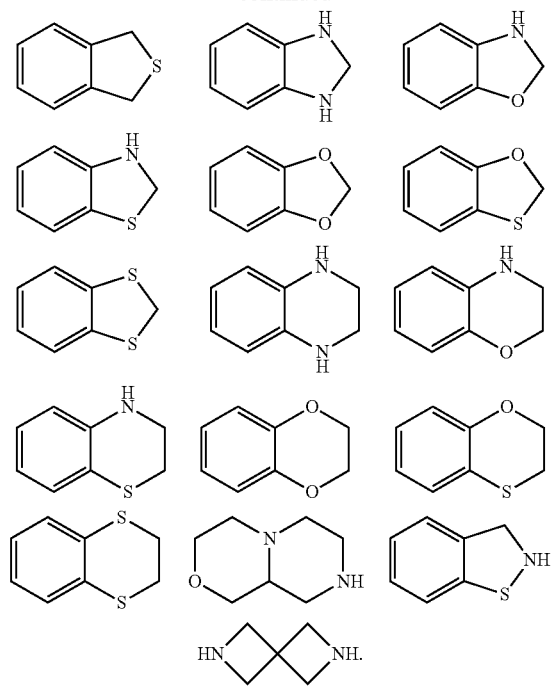

The term "$C_{5-10}$-heteroaryl" means a mono- or polycyclic-ring systems containing one or more heteroatoms independently selected from N, O and $S(O)_r$, wherein r=0, 1 or 2, consisting of 5 to 10 ring atoms wherein at least one of the heteroatoms is part of aromatic ring. The term "heteroaryl" is intended to include all the possible isomeric forms. Thus, the term "heteroaryl" includes the following exemplary structures which are not depicted as radicals as each form may be attached through a covalent bond to any atom so long as appropriate valences are maintained:

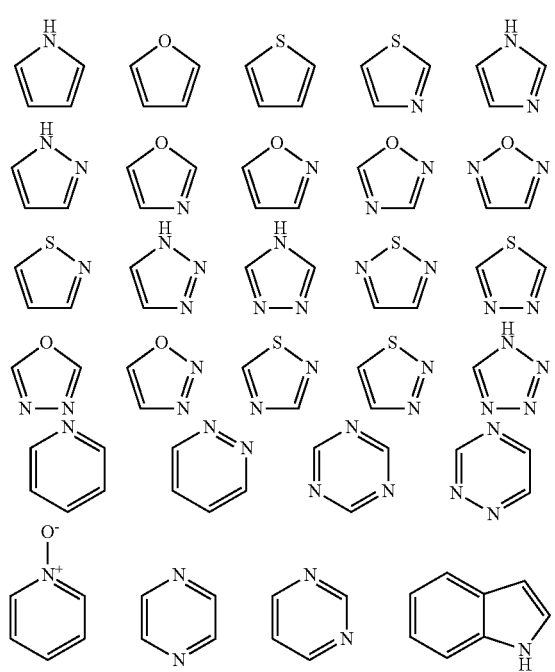

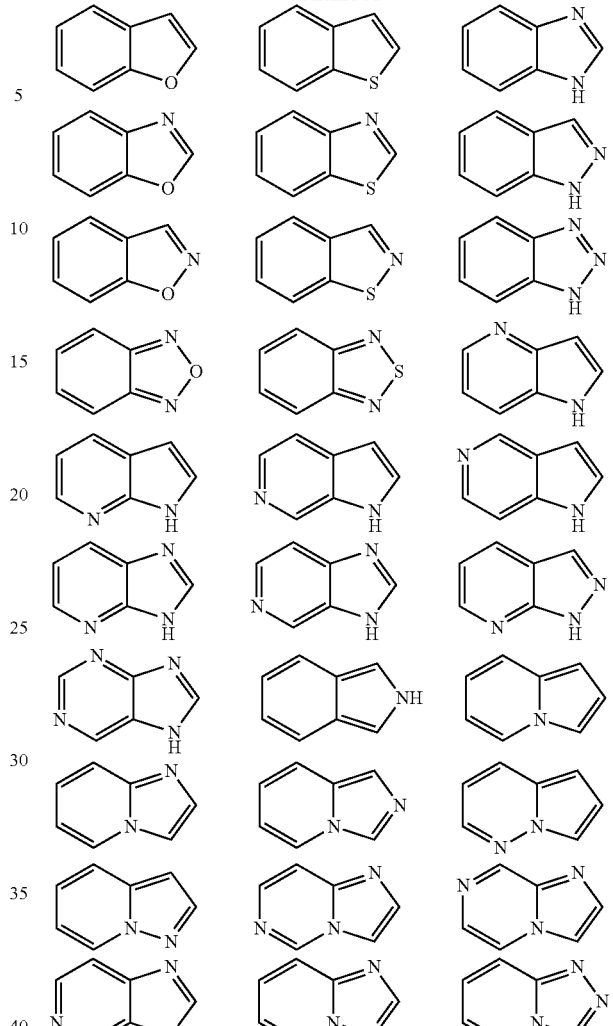

Preparation

General Synthetic Methods

The invention also provides processes for making a compound of Formula I. In all methods, unless specified otherwise, $R^1$, $R^2$ and n in the formulas below shall have the meaning of $R^1$, $R^2$ and n in Formula I of the invention described herein above.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

A compound of Formula V, VII and IX may be made by the method outlined in Scheme 1:

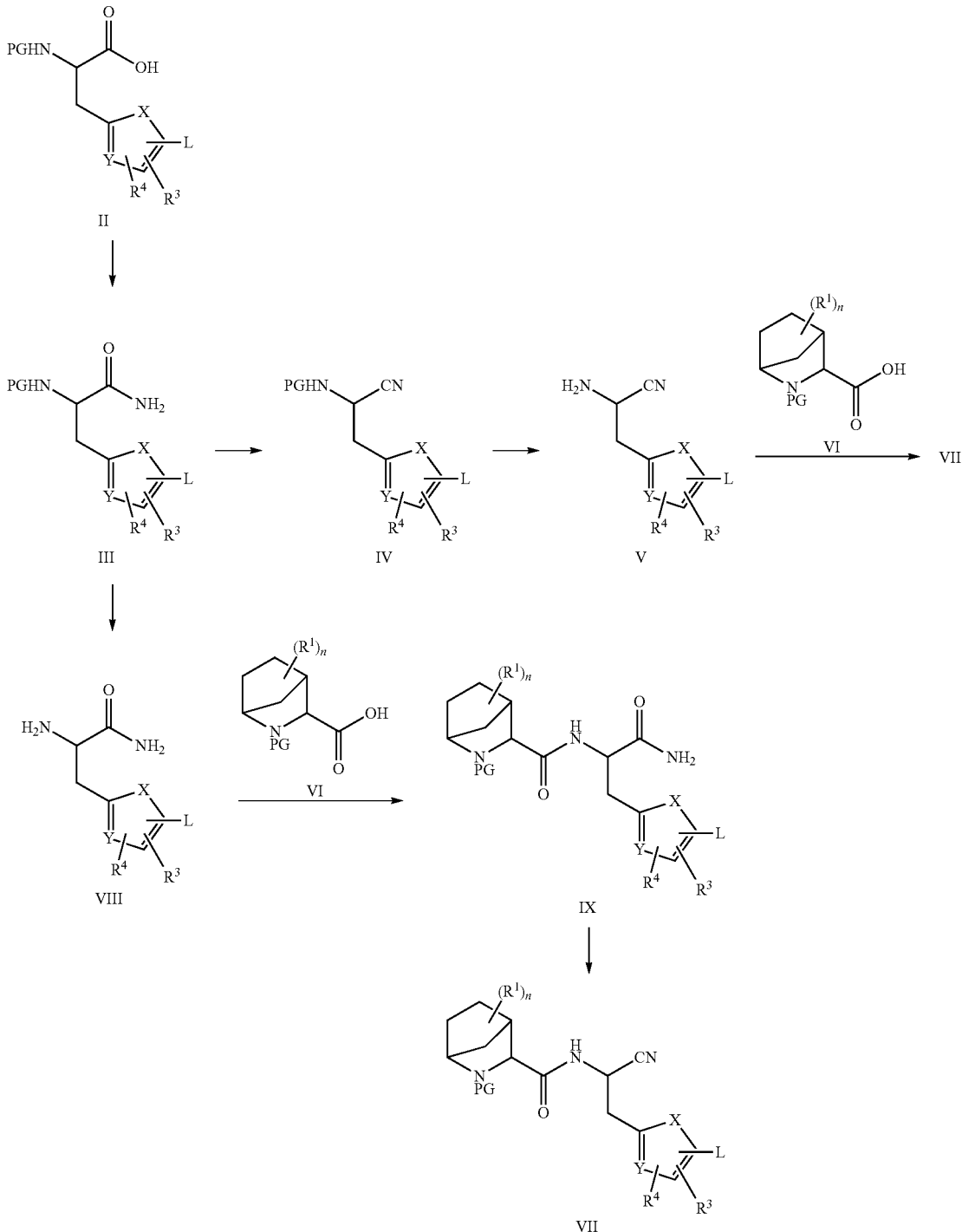

As illustrated in Scheme 1, a compound of Formula II, wherein PG represents a protecting group (e.g. tert-butoxycarbonyl), may be reacted with an aqueous ammonia solution, using standard literature procedures for the formation of an amide. For example, in the presence of a base such as N-methyl-morpholine or N-ethyl-morpholine and an activating agent such as O-(7-Azabenzotriazol-1-yl)-N,N,N',N'-tetramethyluronium hexafluorophosphate (HATU) or O-(Benzotriazol-1-yl)-N,N,N',N'-tetramethyluroniumtetrafluoroborate (TBTU). The reaction is conveniently carried out in a suitable solvent such as N,N-dimethylformamide. Standard peptide coupling reactions known in the art (see for example M. Bodanszky, 1984, The Practice of Peptide Synthesis, Springer-Verlag) may be employed in these syntheses.

Dehydration of an amide such as in a compound of Formula III or Formula IX to the corresponding nitrile of Formula IV or VII may be carried out by use of a dehydration agent such as (methoxycarbonylsulfamoyl)triethyl ammonium hydroxide, in a suitable solvent such as dichloromethane (DCM).

Reacting an acid of Formula VI using standard literature procedures for the formation of an amide, for example in the presence of a base such as N,N-diisopropylethylamine (DIPEA) and an activating agent such as HATU or TBTU, with an amine of Formula V or VIII in a suitable solvent, is provides a compound of Formula VII or IX. Standard peptide coupling reactions known in the art (see for example M. Bodanszky, 1984, The Practice of Peptide Synthesis, Springer-Verlag) may be employed in these syntheses.

The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as formic acid, trifluoroacetic acid, p-toluenesulfonic acid or HCl may be used in a suitable solvent such as water, DCM or dioxane. Another method to deprotect tert-butoxycarbonyl is the reaction with trimethyliodosilane or trimethylchlorosilane in combination with sodium iodide in an appropriate solvent like acetonitrile, DMF or DCM.

Scheme 2

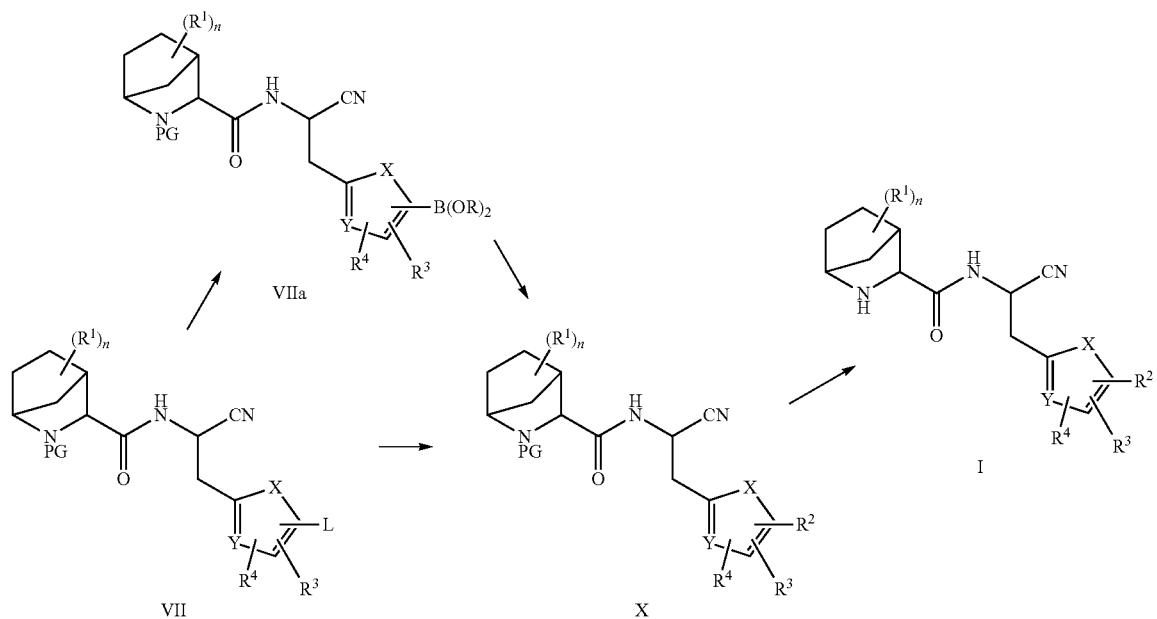

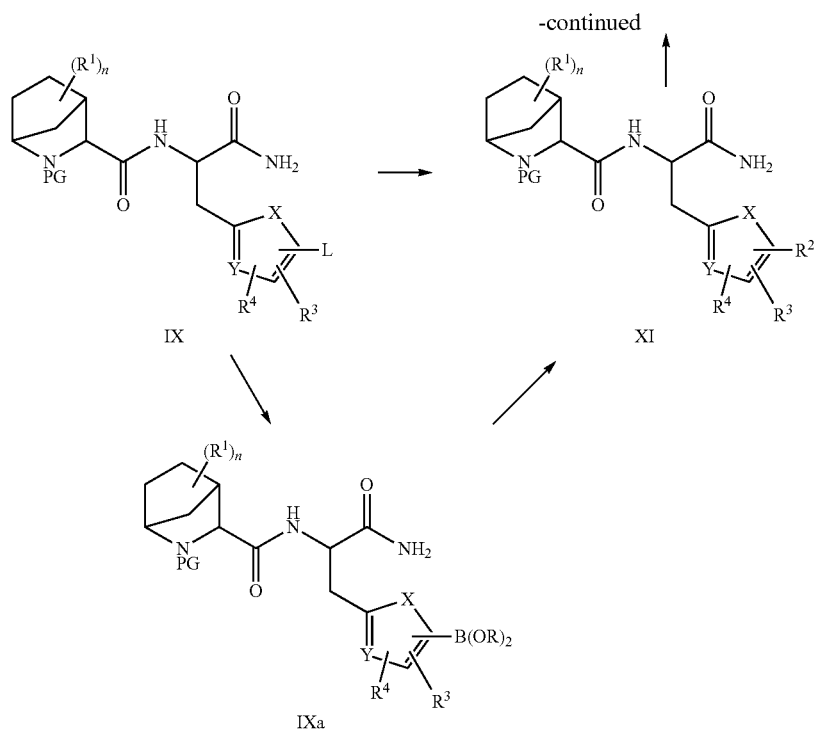

L = I, Br, Cl
X = CH, S, O
Y = CH, N

As illustrated in Scheme 2, (transition) metal catalyzed reaction of a compound of Formula VII or IX wherein L is I, Br or Cl, provides a compound of Formula X or XI. For example, reaction with a boronic acid or the corresponding boronic acid ester, in a suitable solvent such as acetonitrile, in the presence of a suitable catalyst such as 1,1-bis(di-tert-butylphosphino)ferrocene palladium dichloride and a suitable base such as $K_2CO_3$ provides a compound of Formula X or XI. Alternatively, reaction of a compound of Formula VII or IX, wherein L is I, Br or Cl with a tributyl(vinyl)tin reagent in the presence of a suitable catalyst such as bis-(triphenylphosphin)-palladiumchloride, in a suitable solvent such as dimethylformamide (DMF) and if desirable in the presence of an additive such as tetraethylammonium chloride provides compounds of Formula X or XI. Further, reaction of a compound of Formula VII or IX, wherein L is I or Br, may be reacted with an amine in the presence of a suitable catalyst such as Cu(I)I and a suitable base such as caesium carbonate and a suitable promotor such as L-proline provides a compound of Formula X or XI.

In an inversed fashion compounds of formula VII or IX (L: I, Br, Cl) can be converted into the corresponding boronic acid derivatives VIIa or IXa, wherein R can be H or lower alkyl independently and the residues R can form a ring. For example, VII or IX can be reacted with bis-pinacolato-diboron in the presence of a suitable catalyst such as 1,1-bis(di-tert-butylphosphino)ferrocene palladium dichloride and a suitable base such as potassium acetate or sodium, potassium or cesium carbonate or phosphate, in a suitable solvent such as dioxan, dimethylformamide (DMF), or dichloromethane (DCM) to yield the boronic esters VIIa or IXa, respectively. These can be reacted with appropriate aromatic halides in analogy as above to yield the desired coupling products of formula X or XI.

Further modifications of compounds of Formula X, XI and I by methods known in the art and illustrated in the Examples below, may be used to prepare additional compounds of the invention.

Dehydration of an amide of Formula XI to the corresponding nitrile of Formula X may be carried out by use of a dehydration agent such as (methoxycarbonylsulfamoyl)triethyl ammonium hydroxide, in a suitable solvent such as DCM.

Scheme 3

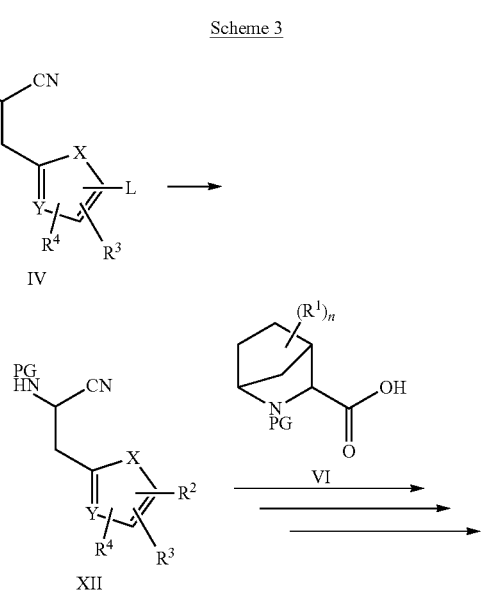

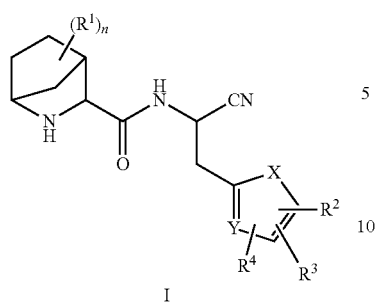

I

L = I, Br, Cl, OTf or N₃
X = CH, S, O
Y = CH, N

As illustrated in Scheme 3, (transition) metal catalyzed reaction of a compound of Formula IV wherein X is I, Br or Cl, provides a compound of Formula XII. For example, reaction with a boronic acid or the corresponding boronic acid ester, in a suitable solvent such as acetonitrile, in the presence of a suitable catalyst such as 1,1-bis(di-tert-butylphosphino) ferrocene palladium dichloride and a suitable base such as $K_2CO_3$ provides a compound of Formula XII.

An acid of Formula VI using standard literature procedures for the formation of an amide, for example in the presence of a base such as DIPEA and an activating agent such as HATU or TBTU, can be reacted with an amine of Formula XII in a suitable solvent. Standard peptide coupling reactions known in the art (see for example M. Bodanszky, 1984, The Practice of Peptide Synthesis, Springer-Verlag) may be employed in these syntheses. Deprotection of functional groups is described in 'Protective Groups in Organic Synthesis', T. W. Greene and P. G. M. Wuts, is Wiley-Interscience. For example, for the deprotection of tert-butoxycarbonyl, an acid such as formic acid, p-toluenesulfonic acid, trifluoroacetic acid or HCl may be used in a suitable solvent such as water, DCM or dioxane and can be performed on the crude amide coupling product to provide a compound of Formula I. Another method to deprotect tert-butoxycarbonyl is the reaction with trimethyliodosilane or trimethylchlorosilane in combination with sodium iodide in an appropriate solvent like acetonitrile, DMF or DCM.

Scheme 4

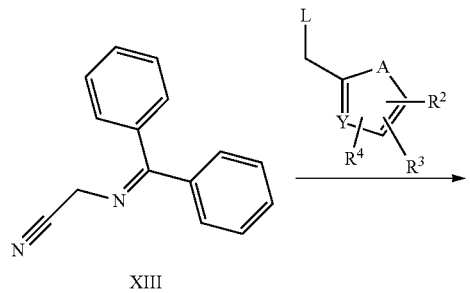

XIII

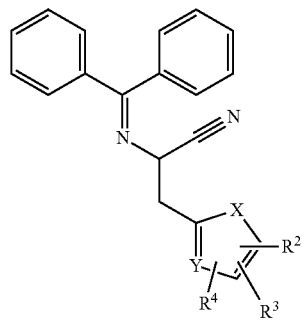

XIV

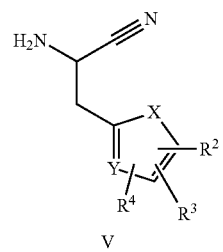

V

L = Cl, Br, OSO₂R

As illustrated in Scheme 4, amino nitrile derivatives of Formula XIII can be converted to substituted amino nitriles of Formula V via alkylation to compounds of Formula XIV, followed by deprotection of the amino group. During the alkylation step a suitable base is used in an appropriate solvent, using a benzylation agent XV with an appropriate leaving group like Cl, Br, or sulfonates. Especially useful is the use of sodium hydroxide as base in water and DCM under phase transfer conditions using benzyltrimethylammonium chloride as described for example by Naidu et al, WO2011/46873. The protective group is removed under acidic conditions, e.g. aq. HCl in dioxan. The amino nitrile V is further processed as depicted in Scheme 1.

Scheme 5

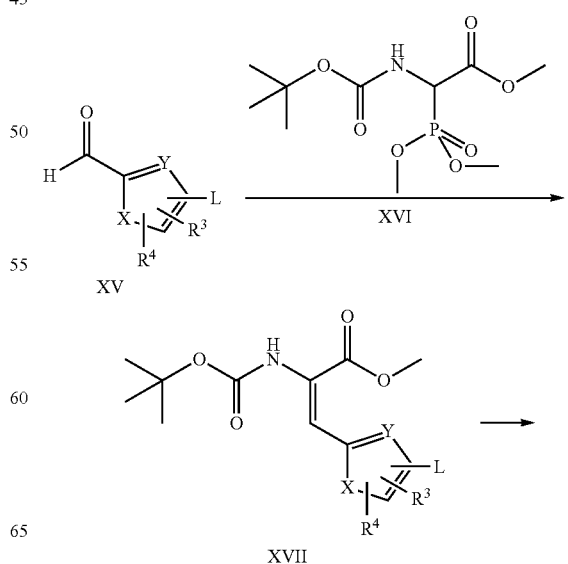

XV

XVI

XVII

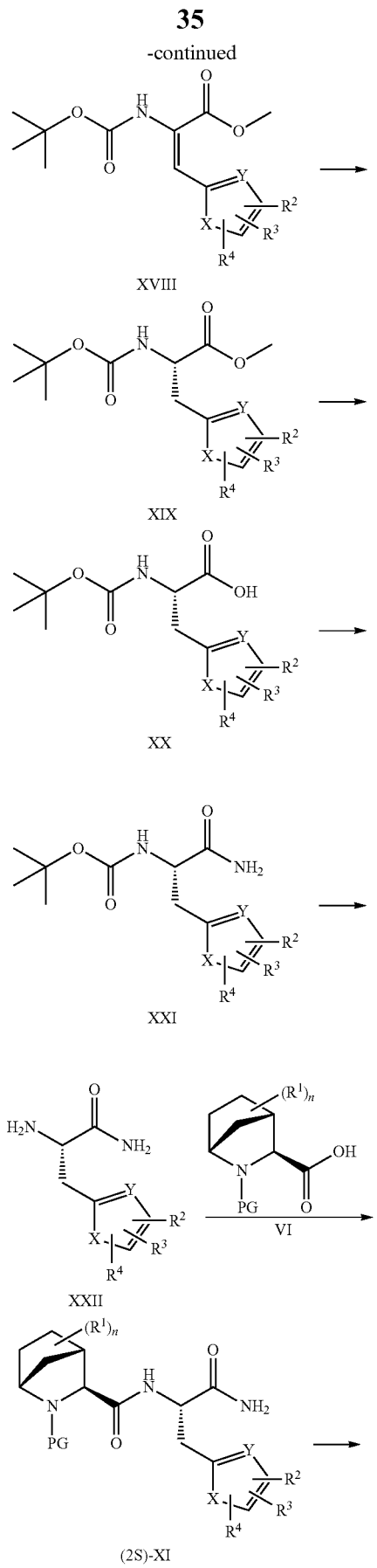
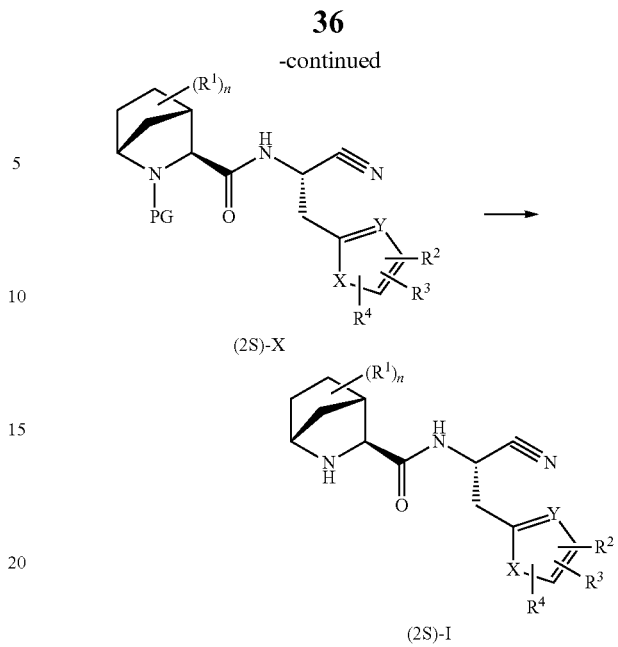

As illustrated in Scheme 5, heteroaromatic aldehydes of type XV can be converted to dehydroamino acid derivatives of formula XVII by use of phosphono glycine derivatives of type XVI. This is performed in the presence of a base e.g., not restricted to tetramethylguanidine, in aprotic solvents like THF. This procedure is published for analogous examples in Cartier et al, J. Org. Chem., 2002, 67, 6256-6259.

The coupling of derivatives of formula XVII with L=I, Br or Cl with boronic acid derivatives to compounds of general formula XVIII is performed in the same way as depicted in Scheme 2 during the conversion of compounds VII to compounds X, or of compounds Ix to compounds XI, respectively.

As described e.g. in Cartier et al, J. Org. Chem., 2002, 67, 6256-6259 with an anaologous system, conversion of dehydroamino acid derivatives of formula XVIII to chiral amino acid derivatives XIX can be performed by homogenous catalytic hydrogenation using a chiral catalyst. Especially useful is (+)-1,2-bis-((2S,5S)-2,5-diethylphospholano)-benzene-(cyclooctadiene)-rhodium (I) trifluoromethanesulfonate, which delivers the desired (2S)-amino acid derivative XIX in a solvent like methanol or ethanol for example at room temperature and 50 psi. A useful amount of the catalyst is 0.1 equivalents, but might be less than that.

The hydrolysis of ester derivatives like XIX to acids of general formula XX can be performed in alkaline media, however, under careful conditions not to epimerize the stereo center adjacent to the ester function. Appropriate conditions are lithium hydroxide in methanol/water (about 10 mmol in 50 mL solvent and 90 min at room temperature. The amino acid is set free carefully with weak acids (e.g. 2 N acetic acid) not to cleave the acid labile Boc protective group.

The conversion of acid derivatives XX to primary amides XXI and following Boc deprotection to primary amides of formula XXI proceeds in an analogous fashion to the conversion of compound II to compounds VIII via compound III as depicted in Scheme I. Amide coupling of amines of the formula XXI with protected amino acids VI leads to amides of the general formula (2S)-XI in analogy to the formation of amides IX as depicted in Scheme 1. Compounds of the formula (2S)-XI are converted to the target compounds (2S)-I in the same way as described in Scheme 2.

Synthetic Examples

The following are representative compounds of the invention which can be made by the general synthetic schemes, the examples, and known methods in the art. Starting materials and intermediates were either commercially available and purchased from catalogues of ABCR, ACROS, ACTIVATE, ALDRICH, ALFA, ANISYN, APOLLO, CHEM IMPEX, COMBI-BLOCKS, E-MERCK, FLUKA, GOLDEN-BRIDGE, MILESTONES, PEPTECH, PHARMABRIDGE, SPECBIOCHEM or were synthesized according to literature or as described below in "Synthesis of starting materials/ educts" Liquid chromatography-mass spectroscopy (LCMS) retention time and observed m/z data for the compounds below are obtained by one of the following methods:

| LC-MS Method V001_003 | |
|---|---|
| Device-Description | Waters Alliance with DAD and MSD |
| Column | Waters XBridge C18 |
| Column Dimension | 4.6 × 30 mm |
| Particle Size | 3.5 μm |

| Gradient/Solvent Time [min] | % Sol [H2O, 0.1% TFA] | % Sol [Methanol] | Flow [ml/min] | Temp [°0 C.] |
|---|---|---|---|---|
| 0.0 | 95 | 5 | 4 | 60 |
| 0.20 | 95 | 5 | 4 | 60 |
| 1.5 | 0 | 100 | 4 | 60 |
| 1.75 | 0 | 100 | 4 | 60 |

| LC-MS Method V001_004 | |
|---|---|
| Device-Description | Waters Alliance with DAD and MSD |
| Column | Waters XBridge C18 |
| Column Dimension | 4.6 × 30 mm |
| Particle Size | 3.5 μm |

| Gradient/Solvent Time [min] | % Sol [H2O, 0.1% TFA] | % Sol [Methanol] | Flow [ml/min] | Temp [°0 C.] |
|---|---|---|---|---|
| 0.0 | 95 | 5 | 4 | 60 |
| 0.20 | 95 | 5 | 4 | 60 |
| 1.5 | 0 | 100 | 4 | 60 |
| 1.9 | 0 | 100 | 4 | 60 |
| 2.0 | 95 | 5 | 4 | 60 |

| LC-MS Method V001_007 | |
|---|---|
| Device-Description | Waters Alliance with DAD and MSD |
| Column | Waters XBridge C18 |
| Column Dimension | 4.6 × 30 mm |
| Particle Size | 3.5 μm |

| Gradient/Solvent Time [min] | % Sol [H2O, 0.1% TFA] | % Sol [Methanol] | Flow [ml/min] | Temp [°0 C.] |
|---|---|---|---|---|
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

| LC-MS Method V003_003 | |
|---|---|
| Device-Description | Waters Alliance with DAD and MSD |
| Column | Waters XBridge C18 |
| Column Dimension | 4.6 × 30 mm |
| Particle Size | 3.5 μm |

| Gradient/Solvent Time [min] | % Sol [H2O, 0.1% NH3] | % Sol [Methanol] | Flow [ml/min] | Temp [° C.] |
|---|---|---|---|---|
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

| LC-MS Method V011_S01 | |
|---|---|
| Device-Description | Waters Alliance with DAD and MSD |
| Column | Waters XBridge C18 |
| Column Dimension | 4.6 × 30 mm |
| Particle Size | 3.5 μm |

| Solvent Gradient time [min] | % Sol [H2O, 0.1% NH3] | % Sol [Acetonitril] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| LC-MS Method V012_S01 | |
|---|---|
| Device-Description | Waters Alliance with DAD and MSD |
| Column | Waters XBridge C18 |
| Column Dimension | 4.6 × 30 mm |
| Particle Size | 3.5 μm |

| Solvent Gradient time [min] | % Sol [H2O, 0.1% TFA] | % Sol [Acetonitril] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| LC-MS Method X001_004 | |
|---|---|
| Device-Description | Waters Acquity with DAD and MSD |
| Column | Waters XBridge C18 |
| Column Dimension | 2.1 × 20 mm |
| Particle Size | 2.5 μm |

| Gradient/Solvent Time [min] | % Sol [H2O, 0.10% TFA] | % Sol [Methanol] | Flow [ml/min] | Temp [° C.] |
|---|---|---|---|---|
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

| LC-MS Method X012_S01 | |
|---|---|
| Device-Description | Waters Acquity with DAD and MSD |
| Column | Waters XBridge BEH C18 |
| Column Dimension | 2.1 × 30 mm |
| Particle Size | 1.7 μm |

LC-MS Method X012_S01

| Solvent Gradient time [min] | % Sol [H₂O, 0.1% TFA] | % Sol [Acetonitril] | Flow [ml/min] | Temp [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

LC-MS Method X018_S01

| Device-Description | Waters Acquity with DAD and MSD |
|---|---|
| Column | Waters Sunfire C18 |
| Column Dimension | 2.1 × 30 mm |
| Particle Size | 2.5 µm |

| Gradient/Solvent Time [min] | % Sol [H₂O, 0.1% TFA] | % Sol [Acetonitril] | Flow [ml/min] | Temp [° C.] |
|---|---|---|---|---|
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

LC-MS Method Z001_002

| Device-Description | Agilent 1200 with DAD and MSD |
|---|---|
| Column | Waters XBridge C18 |
| Column Dimension | 3 × 30 mm |
| Particle Size | 2.5 µm |

| Gradient/Solvent Time [min] | % Sol [H₂O, 0.1% TFA] | % Sol [Methanol] | Flow [ml/min] | Temp [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method A

Synthesis of Example 1:

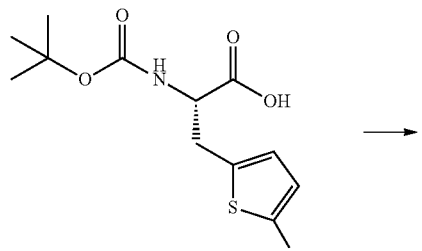

R1

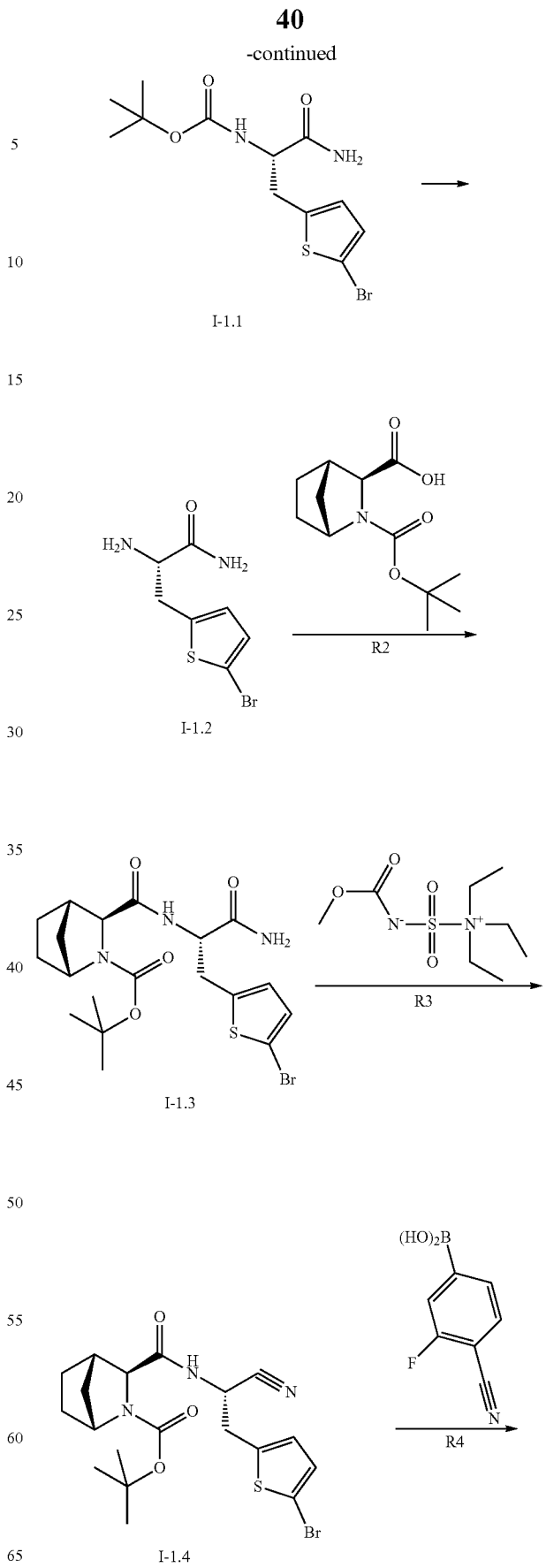

-continued

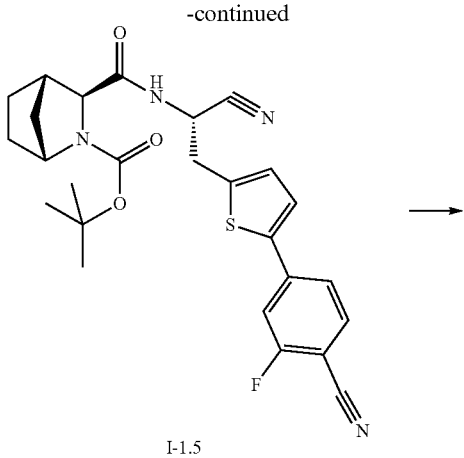

I-1.5

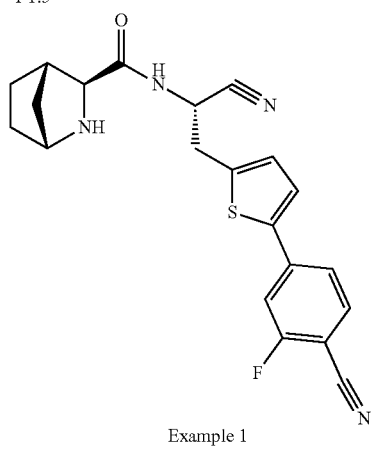

Example 1

Step 1: Synthesis of Intermediate I-1.1

R1 (10.0 g, 28.55 mmol, purchased from Chem-Impex) is dissolved in DMF and 1 eq N-methylmorpholine is added. After addition of TBTU (9.26 g, 28.55 mmol) the mixture is stirred for 30 min, before NH$_4$Cl (1.53 g, 28.55 mmol) and further 3 eq N-methylmorpholine are added. After 1 h at r.t. the mixture is diluted with ethyl acetate, washed 2× with 1 N HCl, 1× with water, 2× with aquous NaHCO$_3$ solution (10%), and 2× with water. The organic layer is dried over MgSO$_4$ and after filtration the solvent in evaporated in vacuo. The product is crystallized with cold methanol. Yield 60% m/z 350/352 [M+H]+. rt 1.29 min, LC-MS Method V003_003.

Step 2: Synthesis of Intermediate I-1.2

I-1.1 (10.7 g, 30.6 mmol) and 8.5 eq TFA in DCM are stirred for 1.5 h at r.t. The solvent is evaporated in vacuo, the residue is triturated with 80 mL diethylether, and the residue is washed with diethylether. Yield 94% m/z 249/251 [M+H]+, rt 0.92 min, LC-MS Method V003_003

Step 3: Synthesis of Intermediate I-1.3

R2 (7.9 g, 31.8 mmol) mmol) (purchased from Aldrich or synthesized in analogy to Tararov et al, Tetrahedron Asymmetry 13 (2002), 25-28) is dissolved in DCM, and 1 eq DIPEA and HATU (12 g, 31.6 mmol) are added. After stirring for 15 min at r.t. I-1.2 (10.5 g, 28.9 mmol) as trifluoroactetate and further 1.5 eq DIPEA are added, and the mixture is stirred for 2 h at r.t. The mixture is washed 3× with 1N HCl, 2× with aquous NaHCO$_3$ solution (10%) and 1× with water. The organic layer is dried over MgSO$_4$, filtered, and the filtrate is evaporated in vacuo. The residue is purified by MPLC.

Yield 78%, m/z=470/472 [M+H]+, rt 1.37 min, LC-MS Method V003_003, TLC Rf=0.30 (silica gel Merck 60 F 254, DCM/MeOH 95:5).

Step 4: Synthesis of Intermediate I-1.4

I-1.3 (10.4 g, 22 mmol) and R3 (11.54 g, 48.4 mmol) are dissolved in DCM and stirred for 12 h at r.t. The mixture is washed 2× with 1N acetic acid, 2× with aquous NaHCO$_3$ solution (10%) and 2× with water. The organic layer is dried over MgSO$_4$, filtrated, and the filtrate is evaporated in vacuo. The residue is triurated with diethylether. The precipitate is purified by MPLC (DCM/MeOH 98:2). Yield 82%. m/z 454/456 [M+H]+, rt 1.38 min, LC-MS Method V003_003, TLC Rf=0.28 (silica gel Merck 60 F 254, DCM/MeOH 98:2).

Synthesis of Intermediate I-1.4.1

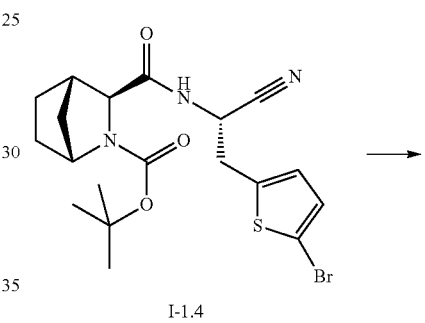

I-1.4

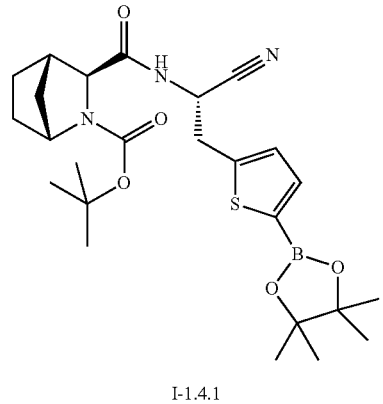

I-1.4.1

During the synthesis of Intermediate I-1.5.6 the bromothiophene I-1.4 is converted to boronic ester I-1.4.1, which then is coupled with 5-bromo-3H-isobenzofuran-1-one (5-bromophthalide).

For that purpose I-4.1 (1.5 g, 3.3 mmol) and bis-pinacolatodiboron (1.257 g, 4.952 mmol) are dissolved in 10 mL dioxane under argon. [1,1'-bis-(diphenylphosphino)-ferrocene]-palladium(II)-dichloride DCM complex (1:1) (269.6 mg, 0.33 mmol) and potassium acetate (972 mg, 9.9 mmol) are added and the reaction vessel is again put under argon. The mixture is stirred for 6 h at 100° C. After cooling to r.t. water and ethyl acetate are added and the organic layer is washed with water. The organic layer is dried, and the product is purified by MPLC (cyclohexane/ethyl acetate 6:4, 247 nm UV detection). The fractions containing the product are combined and the solvent is removed by lyophilization. Yield 16%. m/z 502 [M+H]+.

Step 5: Synthesis of Intermediate I-1.5

I-1.4 (250 mg, 0.55 mmol) and boronic acid R4 (99.8 mg, 0.005 mmol) are dissolved in 3 mL dioxan and 1 mL methanol in a microwave vial under argon. [1,1'-bis-(diphenylphosphino)-ferrocene]-palladium(II)-dichloride DCM complex (1:1) (13.5 mg, 0.017 mmol) and 2M aqueous $Na_2CO_3$ solution (0.619 mL, 1.238 mmol) are added. The mixture is refluxed for 12 h, and after cooling to r.t. the mixture is treated with water and ethyl acetate, and the organic layer is washed 2× with water and dried over $MgSO_4$. After filtration the solution is evaporated in vacuo. Yield: 300 mg crude product.

The following intermediates as shown in Table 2 are synthesized in a similar fashion from the appropriate intermediates:

TABLE 2

| Intermediate | Educt | Structure of Intermediate | m/z [M + H]+ | rt (min) | LC-MS method |
| --- | --- | --- | --- | --- | --- |
| I-1.5.1 | I-1.4 | | 521 | 0.74 | X001_004 |
| I-1.5.2 | I-1.4 | | 500 | n.d. | n.d. |
| I-1.5.3 | I-1.4 | | 470 | 1.14 | V012_S01 |

TABLE 2-continued

| Intermediate | Educt | Structure of Intermediate | m/z [M + H]+ | rt (min) | LC-MS method |
|---|---|---|---|---|---|
| I-1.5.4 | I-1.4 | | 507 | n.d. | n.d. |
| I-1.5.5 | I-1.4 | | 540 | n.d. | n.d. |
| I-1.5.6 | I-1.4.1 | | 508 | n.d. | n.d. |
| I-1.5.7 | I-1.4 | | 471 | 0.91 | V012_S01 |

TABLE 2-continued
| Intermediate | Educt | Structure of Intermediate | m/z [M + H]+ | rt (min) | LC-MS method |
|---|---|---|---|---|---|
| I-1.5.8 | I-1.5.7 (by hydrogenation on at r.t. and 50 psi with Pd/C in methanol) | 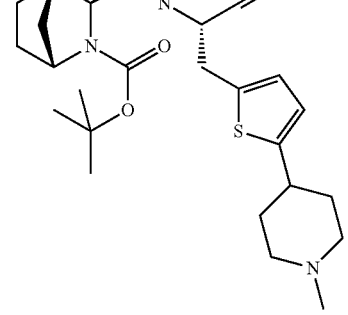 | 473 | n.d. | n.d. |
| I-1.5.9 | I-1.4 | 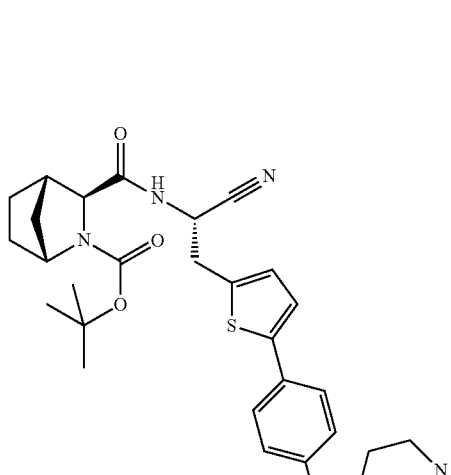 | 614 | n.d. | n.d. |
| I-1.5.10 | I-1.4 | 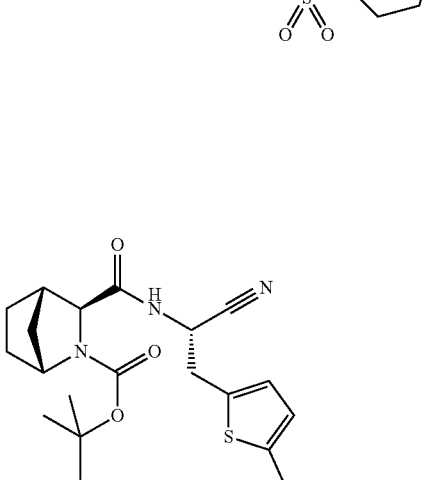 | 536 | n.d. | n.d. |

TABLE 2-continued
| Intermediate | Educt | Structure of Intermediate | m/z [M + H]+ | rt (min) | LC-MS method |
|---|---|---|---|---|---|
| I-1.5.11 | I-1.4 | 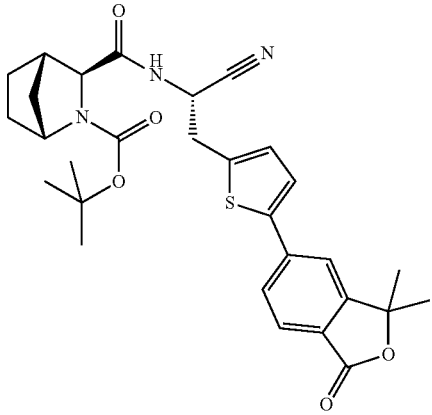 [SMILES: CC(C)(C)OC(=O)N1[C@@H]2CC[C@@H](C2)[C@H]1C(=O)N[C@H](C#N)Cc1ccc(-c2ccc3c(c2)C(C)(C)OC3=O)s1] | 536 | n.d. | n.d. |
| I-1.5.12 | I-1.4 | 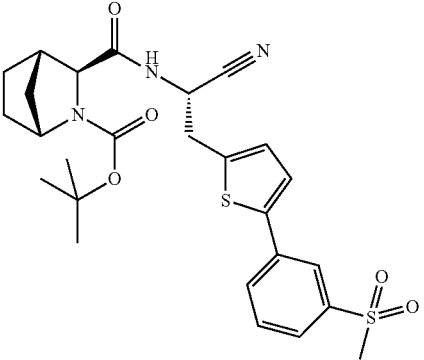 [SMILES: CC(C)(C)OC(=O)N1[C@@H]2CC[C@@H](C2)[C@H]1C(=O)N[C@H](C#N)Cc1ccc(-c2cccc(S(C)(=O)=O)c2)s1] | 530 | 1.18 | X012_S01 |
| I-1.5.13 | I-1.4 | 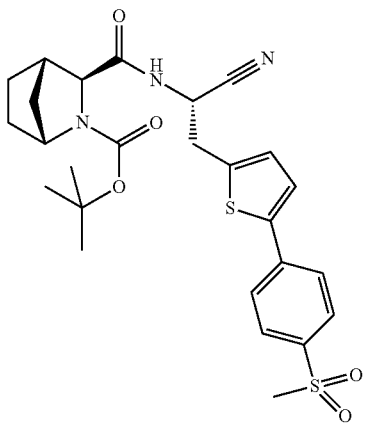 [SMILES: CC(C)(C)OC(=O)N1[C@@H]2CC[C@@H](C2)[C@H]1C(=O)N[C@H](C#N)Cc1ccc(-c2ccc(S(C)(=O)=O)cc2)s1] | 530 | 0.62 | X012_S01 |

TABLE 2-continued

| Intermediate | Educt | Structure of Intermediate | m/z [M + H]+ | rt (min) | LC-MS method |
|---|---|---|---|---|---|
| I-1.5.14 | I-1.4 | | 535 | 1.20 | V012_S01 |

Step 6: Synthesis of Example 1

I-1.5 (300 mg, 0.221 mmol) is dissolved in 8 mL acetonitrile, and sodium iodide (247.4 mg, 1.65 mmol) and trimethylchlorosilane (209.5 µL, 1.65 mmol) are added. After stirring for 1 h at r.t. 20 mL methanol are added. The solvent is evaporated in vacuo and the residue is purified by reversed phase HPLC. The fractions which contain the product are evaporated, treated with acetonitrile and freeze-dried.

Yield 40%, m/z 395 [M+H]+, rt 0.55 min, LC-MS Method V001_004.

Method B

Synthesis of Example 22

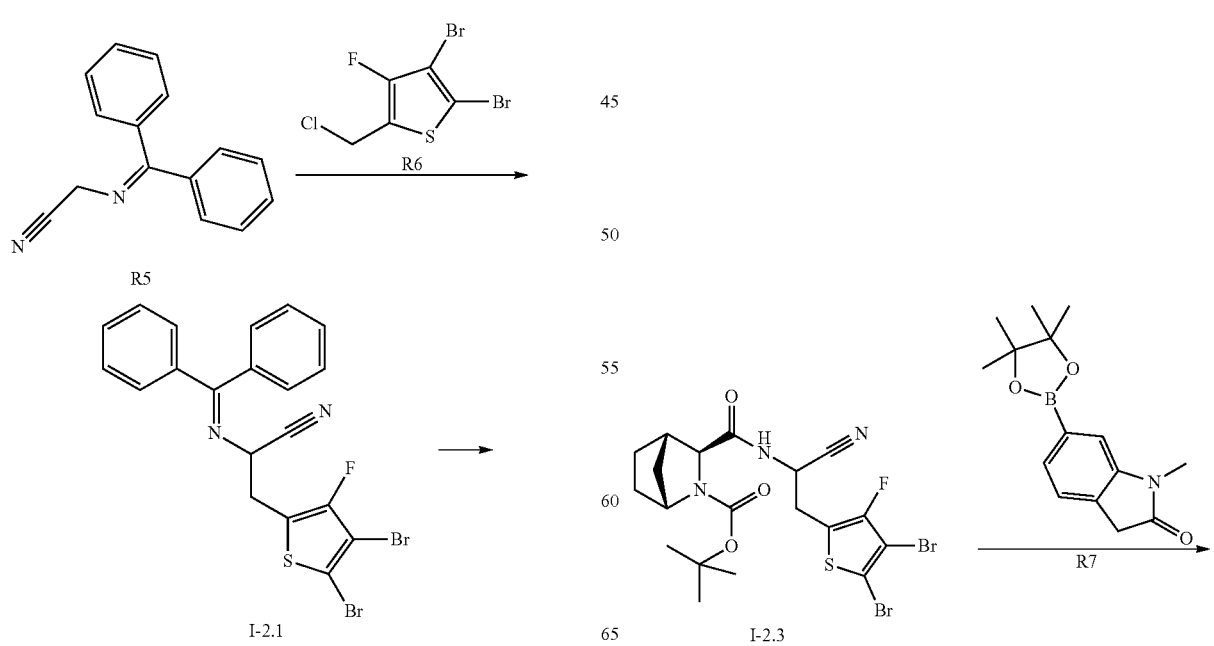

-continued

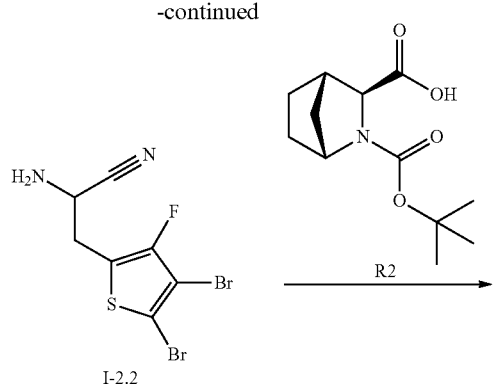

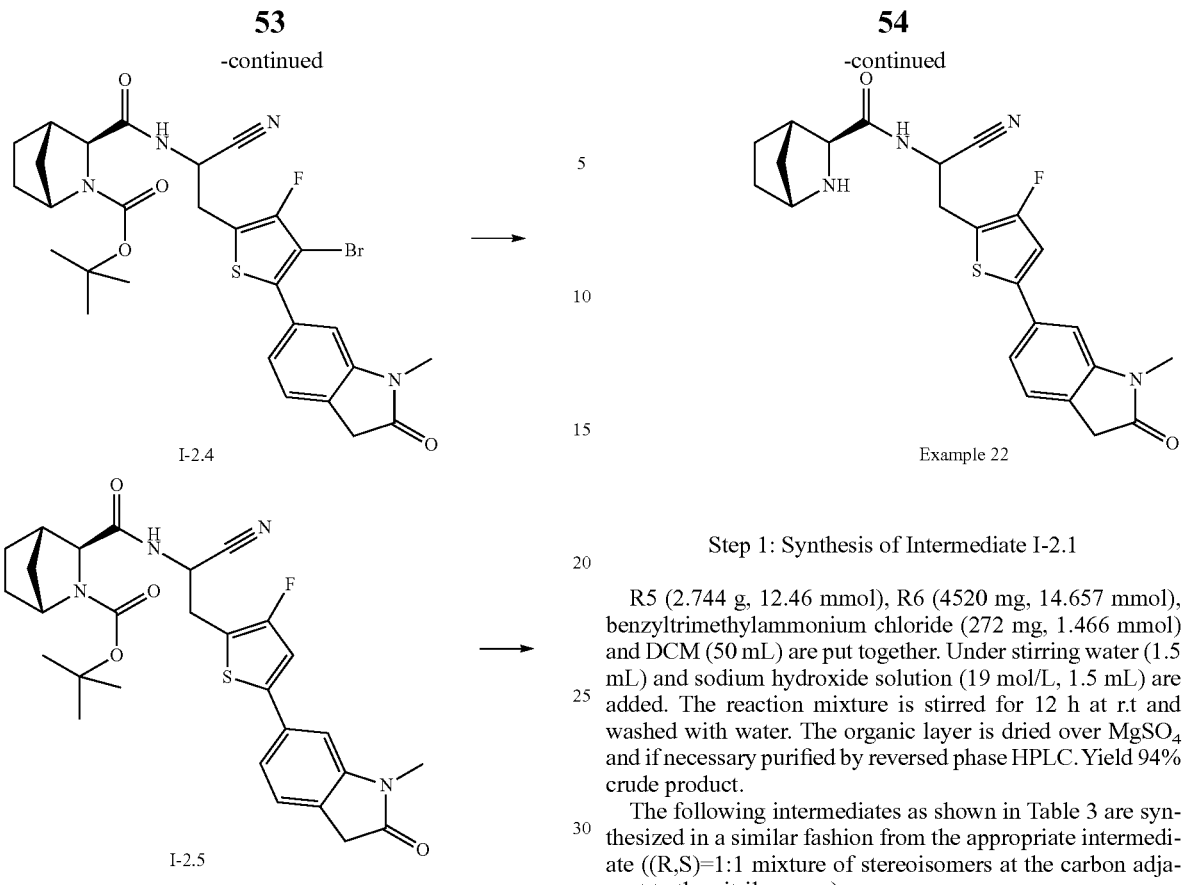

Step 1: Synthesis of Intermediate I-2.1

R5 (2.744 g, 12.46 mmol), R6 (4520 mg, 14.657 mmol), benzyltrimethylammonium chloride (272 mg, 1.466 mmol) and DCM (50 mL) are put together. Under stirring water (1.5 mL) and sodium hydroxide solution (19 mol/L, 1.5 mL) are added. The reaction mixture is stirred for 12 h at r.t and washed with water. The organic layer is dried over $MgSO_4$ and if necessary purified by reversed phase HPLC. Yield 94% crude product.

The following intermediates as shown in Table 3 are synthesized in a similar fashion from the appropriate intermediate ((R,S)=1:1 mixture of stereoisomers at the carbon adjacent to the nitrile group):

TABLE 3-continued

| Intermediate | Structure | m/z [M + H]+ | rt (min) | LC-MS method |
|---|---|---|---|---|
| I-2.1.5 | 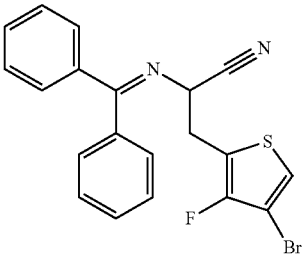 [SMILES: N#CC(Cc1scc(Br)c1F)N=C(c1ccccc1)c1ccccc1] | 413/415 | 1.46 | V011_S01 |
| I-2.1.6 | 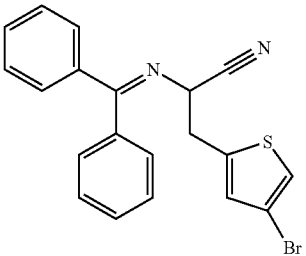 [SMILES: N#CC(Cc1cc(Br)cs1)N=C(c1ccccc1)c1ccccc1] | 395/397 | 1.49 | V011_S01 |
| I-2.1.7 | 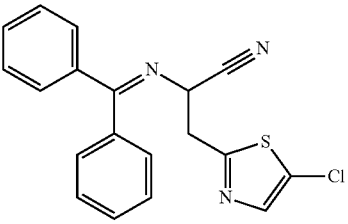 [SMILES: N#CC(Cc1ncc(Cl)s1)N=C(c1ccccc1)c1ccccc1] | n.d. | n.d. | n.d. |

Step 2: Synthesis of Intermediate I-2.2

I-2.1 (6800 mg, 13.815 mmol) in dioxane (100 mL) aq. HCl (1 mol/L, 42 mL) is added. The reaction mixture is stirred for 1.5 h. The solvent is evaporated in vacuo, crystallized in acetonitrile and washed with acetonitrile and diethylether. If necessary the product is purified by reversed phase HPLC. Yield 36.5% crude product.

The following intermediates as shown in Table 4 are synthesized in a similar fashion from the appropriate intermediate ((R,S)=1:1 mixture of stereoisomers at the carbon adjacent to the nitrile group):

TABLE 4

| Intermediate | Educt | Structure of Intermediate | m/z [M + H]+ | rt (min) | LC-MS method |
|---|---|---|---|---|---|
| I-2.2.2 | I-2.1.2 | 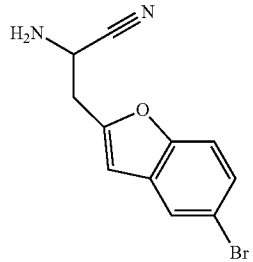 [SMILES: N#CC(N)Cc1cc2cc(Br)ccc2o1] | 265/267 | 0.41 | X012_S01 |

TABLE 4-continued

| Intermediate | Educt | Structure of Intermediate | m/z [M + H]+ | rt (min) | LC-MS method |
|---|---|---|---|---|---|
| I-2.2.3 | I-2.1.3 | (structure) | 281/283 | n.d. | n.d. |
| I-2.2.5 | I-2.1.5 | (structure) | 249/251 | n.d. | n.d. |
| I-2.2.6 | I-2.1.6 | (structure) | 231/233 | 0.30 | X012_S01 |
| I-2.2.7 | I-2.1.7 | (structure) | 188 | n.d. | n.d. |

Step 3: Synthesis of Intermediate I-2.3

To R2 (1380 mg, 5.554 mmol) in DMF (20 mL) diisopropylethylamine (0.87 mL, 5.05 mmol) is added, and after cooling to 5° C., TBTU (1.7 g, 5.3 mmol) and stirred for 15 min. Then intermediate I-2.2 as HCl salt (1840 mg, 5.05 mmol) together with another 1.5 eq DIPEA is added and the mixture stirred for 2 h at r.t. The mixture is treated with water and ethyl acetate, and the organic layer is washed 2× with 1 N HCl, 1× with water, 1× with aq. $NaHCO_3$ solution (5%) and 2× with water. The organic layer is dried over $MgSO_4$ and after filtration the solvent is evaporated in vacuo. Yield 92%, m/z 551/552/553/554 [M+H]+, rt 0.74 min, LC-MS Method X012_S01, TLC Rf=0.28 silica gel Merck 60 F 254 (cyclohexane/ethylacetate 7:3).

The following intermediates as shown in Table 5 are synthesized in a similar fashion from the appropriate intermediate ((R,S)=1:1 mixture of stereoisomers at the carbon adjacent to the nitrile group):

TABLE 5

| Intermediate | Educt | Structure of Intermediate | m/z [M + H]+ | rt (min) | LC-MS method |
|---|---|---|---|---|---|
| I-2.3.2 | I-2.2.2 | 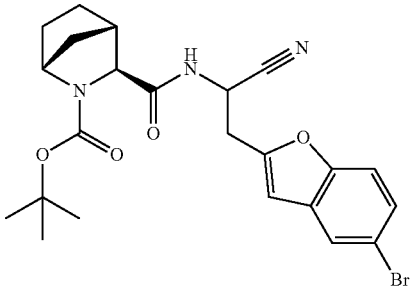 [SMILES: CC(C)(C)OC(=O)N1[C@@H]2CC[C@@H](C2)[C@H]1C(=O)NC(C#N)Cc1cc2cc(Br)ccc2s1] | 488/490 | 0.74 | X012_S01 |
| I-2.3.3 | I-2.2.3 | 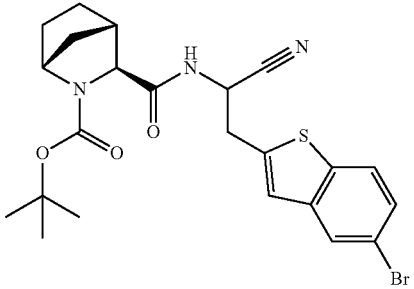 | 504/506 | 1.33 | V011_S01 |
| I-2.3.5 | I-2.2.5 | 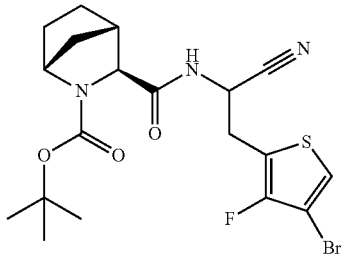 [SMILES: CC(C)(C)OC(=O)N1[C@@H]2CC[C@@H](C2)[C@H]1C(=O)NC(C#N)Cc1scc(Br)c1F] | 474/476 | 1.24 | V011_S01 |
| I-2.3.6 | I-2.2.6 | 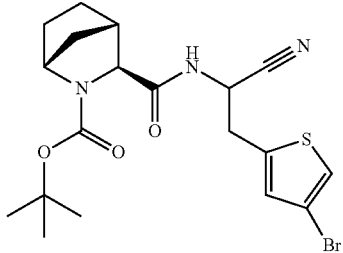 [SMILES: CC(C)(C)OC(=O)N1[C@@H]2CC[C@@H](C2)[C@H]1C(=O)NC(C#N)Cc1cc(Br)cs1] | 454/456 | 1.26 | V011_S01 |
| I-2.3.7 | I-2.2.7 | 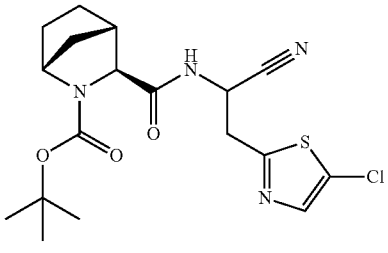 [SMILES: CC(C)(C)OC(=O)N1[C@@H]2CC[C@@H](C2)[C@H]1C(=O)NC(C#N)Cc1ncc(Cl)s1] | 411 | n.d. | n.d. |

Step 4: Synthesis of Intermediate I-2.4

I-2.3 (1460 mg, 2.648 mmol) and R7 (759.55 mg, 2.78 mmol) are dissolved in 15 mL acetonitrile divided in 13 microwave vials under argon. 1,1-Bis(di-tert-butylphosphino)ferrocene palladium dichloride (172.6 mg, 0.265 mmol) and a 2M aq. solution of Na$_2$CO$_3$ (2.65 mL, 5.3 mmol) are added and the reaction mixture again put under argon. After stirring for 4 h at 80° C., the combined mixtures are diluted to a volume of 150 mL with ethyl acetate and washed 3× with water. The organic layer is dried over MgSO$_4$ and filtrated. The filtrate is evaporated in vacuo, and the residue is purified by MPLC (DCM/MeOH 98:2). Yield: 45%, m/z 618/620 [M+H]+, rt 0.69 min, LC-MS Method X012_S01.

The following intermediates as shown in Table 6 are synthesized in a similar fashion from the appropriate intermediate ((R,S)=1:1 mixture of stereoisomers at the carbon adjacent to the nitrile group):
TABLE 6
| Intermediate | Educt | Structure of Intermediate | m/z [M + H]+ | rt (min) | LC-MS method |
|---|---|---|---|---|---|
| I-2.4.2 | I-2.3.2 | 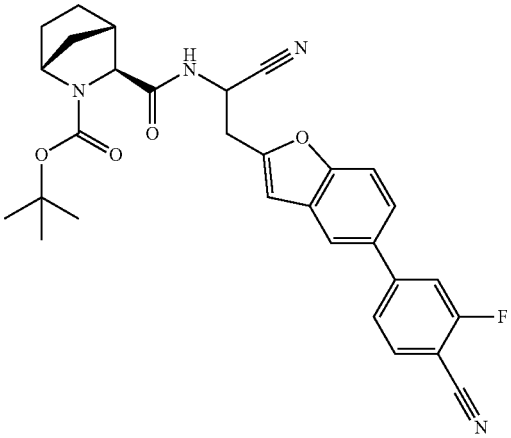 [SMILES: CC(C)(C)OC(=O)N1[C@@H]2CC[C@@H](C2)[C@H]1C(=O)NC(C#N)Cc1cc2cc(-c3ccc(C#N)c(F)c3)ccc2o1] | 529 | 1.34 | V012_S01 |
| I-2.4.3 | I-2.3.2 | 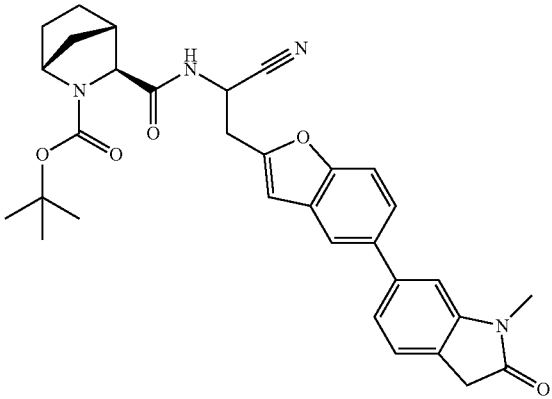 [SMILES: CN1C(=O)Cc2ccc(-c3ccc4oc(CC(C#N)NC(=O)[C@@H]5[C@H]6CC[C@H](C6)N5C(=O)OC(C)(C)C)cc4c3)cc21] | 555 | 0.68 | X012_S01 |
| I-2.4.4 | I-2.3.2 | 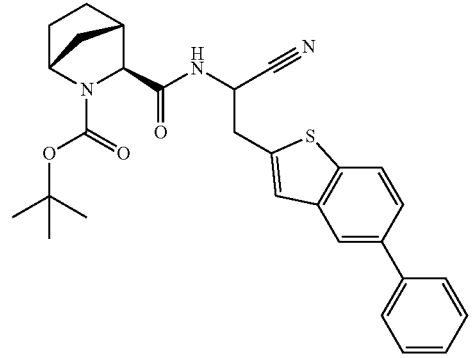 [SMILES: CC(C)(C)OC(=O)N1[C@@H]2CC[C@@H](C2)[C@H]1C(=O)NC(C#N)Cc1cc2cc(-c3ccccc3)ccc2s1] | 486 | 0.78 | X012_S01 |

TABLE 6-continued
| Intermediate | Educt | Structure of Intermediate | m/z [M + H]+ | rt (min) | LC-MS method |
|---|---|---|---|---|---|
| I-2.4.5 | I-2.3.3 | 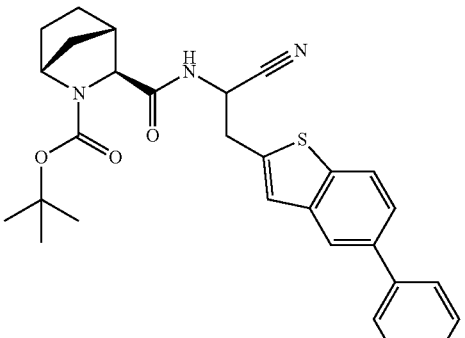 | 502 | 1.40 | V011_S01 |
| I-2.4.7 | I-2.3.5 | 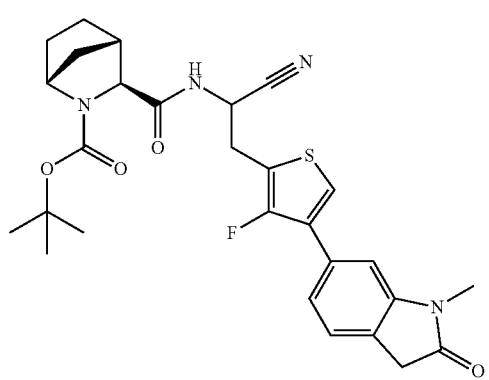 [SMILES: CN1C(=O)Cc2ccc(-c3csc(CC(C#N)NC(=O)[C@@H]4[C@H]5CC[C@H](C5)N4C(=O)OC(C)(C)C)c3F)cc21] | 539 | 0.69 | Z001_002 |
| I-2.4.8 | I-2.3.6 | 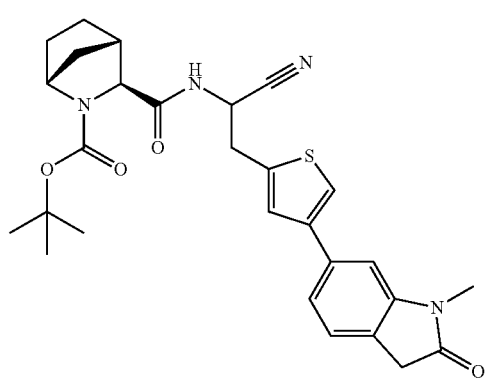 [SMILES: CN1C(=O)Cc2ccc(-c3csc(CC(C#N)NC(=O)[C@@H]4[C@H]5CC[C@H](C5)N4C(=O)OC(C)(C)C)c3)cc21] | 521 | 1.17 | V011_S01 |
| I-2.4.9 | I-2.3.7 | 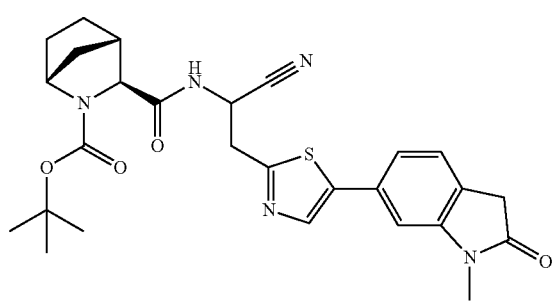 [SMILES: CN1C(=O)Cc2ccc(-c3cnc(CC(C#N)NC(=O)[C@@H]4[C@H]5CC[C@H](C5)N4C(=O)OC(C)(C)C)s3)cc21] | 522 | n.d. | n.d. |

Step 5: Synthesis of Intermediate I-2.5

I-2.4 (330 mg, 0.534 mmol) is dissolved in 20 mL methanol and hydrogenated with 100 mg Pd/C for 24 h at 50 psi and r.t. After filtering off the catalyst the solution is evaporated in vacuo. Yield: 79%, m/z 539 [M+H]+, rt 1.20 min, LC-MS Method V012_S01.

Step 6: Synthesis of Example 22

To I-2.5 (225 mg, 0.418 mmol) in acetonitrile (15 mL) sodium iodide (187.8 mg, 1.253 mmol) and chlorotrimethylsilane (158.3 μL, 1.253 mmol) are added. The mixture is stirred for 1 h at r.t. 20 mL methanol are added, stirred for 10 min and the solvent is evaporated in vacuo. After filtering the filtrate is treated with 32.2 μL TFA and the product is purified by semipreparative HPLC-MS. The fraction which contain the product are combined and freeze-dried. Yield 17%, m/z 439 [M+H]+, rt 0.41 min, LC-MS Method X012_S01.

Method C

Synthesis of Example 5

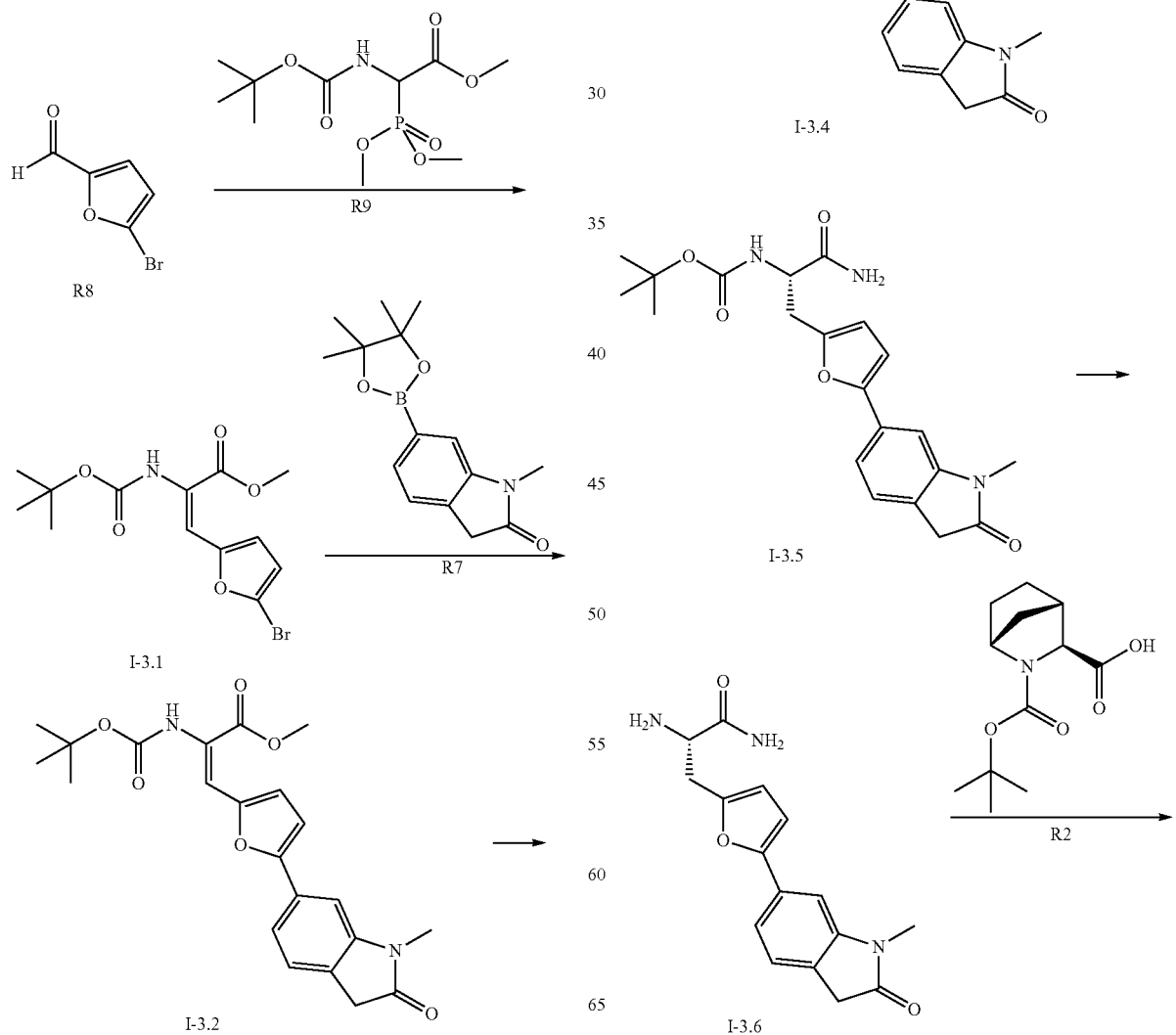

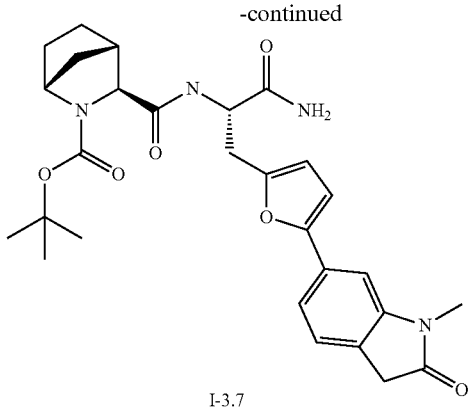

I-3.7

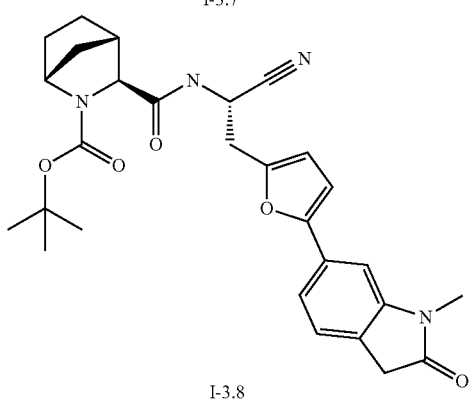

I-3.8

Example 5

Step 1: Synthesis of Intermediate I-3.1

R9 (9.343 g, 31.432) is dissolved in 20 mL THF and cooled down to −65° C. Tetramethylguanidine (3.952 g, 31.432 mmol) is added and stirred for 15 min at this temperature. R8 (5 g, 28.575 mmol) dissolved in 10 mL THF is added, and the mixture is stirred for 12 h at r.t. After addition of water and ethyl acetate the organic layer is washed 3× with water and dried over MgSO$_4$. After filtering the filtrate is solvent is evaporated in vacuo. The residue is crystallized with petrol ether, isolated by filtration and washed with petrol ether. Yield 83%, m/z 346/348 [M+H]+, rt 0.63 min, LC-MS Method X012_S01, TLC Rf=0.33 (silica gel Merck 60 F 254, DCM/methanol 98:2).

Step 2: Synthesis of Intermediate I-3.2

I-3.1 (1.5 g, 4.333 mmol) and R7 (1.243 g, 4.55 mmol) are dissolved in 15 mL acetonitrile under argon. 1,1-Bis(di-tert-butylphosphino)ferrocene palladium dichloride (282.4 mg, 0.433 mmol) and 2M aq. Na$_2$CO$_3$ solution (4.333 mL, 8.666 mmol) are added and again put under argon. The mixture is stirred 3 h at 85° C. After cooling to r.t. the mixture is filtered, and the filtrate is diluted with ethyl acetate to a volume of 200 mL. The organic layer is washed 2× with aq. NaHCO$_3$ solution (5%) and 2× with water, dried over MgSO$_4$, filtrated, and the filtrate is evaporated in vacuo. The residue is purified by MPLC (DCM/methanol 99:1, 240 nm UV detection). The fractions containing the product are combined, and the solvent is evaporated in vacuo. Yield 64% m/z 413 [M+H]+, rt 1.14 min, LC-MS Method V011_S01, TLC Rf=0.60 (silica gel Merck 60 F 254, DCM/methanol 99:1).

Step 3: Synthesis of Intermediate I-3.3

I-3.2 (1.11 g, 2.691 mmol) and (+)-1,2-bis-((2S,5S)-2,5-diethylphospholano)-benzene-(cyclooctadiene)-rhodium (I) trifluoromethanesulfonate (194.5 mg, 0.269 mmol) are suspended in 60 mL methanol and hydrogenated for 18 h at r.t. and 50 psi. The catalyst is removed by filtration, and the solvent is evaporated in vacuo. The residue is purified by MPLC (DCM/methanol 98:2 254 nm mass detection), the fractions containing the product are combined and the solvent is evaporated in vacuo.

Yield >98% m/z 415 [M+H]+, rt 1.16 min, LC-MS Method V011_S01, TLC Rf=0.33 (silica gel Merck 60 F 254, DCM/methanol 98:2).

Step 4: Synthesis of Intermediate I-3.4

I-3.3 (1150 mg, 2.775 mmol) is dissolved in 40 mL methanol and LiOH (199.35 mg, 8.324 mmol) in 10 mL water are added. After stirring for 90 min at r.t. the mixture is diluted with water to a volume of 150 mL, acidified with 2 N acetic acid to pH 4, extracted with ethyl acetate, and the organic layer is washed 3× with water. The combined organic phases are dried over MgSO$_4$, filtrated, and the solvent is evaporated in vacuo. Yield 82% m/z 401 [M+H]+, rt 0.70 min, LC-MS Method V011_S01.

Step 5: Synthesis of Intermediate I-3.5

I-3.4 (910 mg, 2.273 mmol) and 1 eq DIPEA (0.391 mL) are dissolved in 20 mL DMF, and TBTU (730 mg, 2.273 mmol) is added. After 20 min at r.t. NH$_4$Cl (607.8 mg, 11.363 mmol) and 5 eq DIPEA (1.955 mL) are added, and the mixture is stirred for 3 h at r.t. Afterwards the mixture is dilute with water to 100 mL, extracted 2× with ethyl acetate, and the combined organic layers are is washed 2× with aq. Na$_2$CO$_3$ solution (10%), 1× with water, 2× with 1 N HCl and again 4× with water. The organic phase is dried over MgSO$_4$, filtrated, and the solvent is evaporated in vacuo. The residue is purified by MPLC (DCM/methanol 96:4, 254 nm UV detection). The fractions containing the product are combined and the solvent is evaporated in vacuo. Yield 51% m/z 400 [M+H]+, rt 0.98 min, LC-MS Method V011_S01, TLC Rf=0.10 (silicagel Merck 60 F 254, DCM/methanol 95:5).

Step 6: Synthesis of Intermediate I-3.6

I-3.5 (450 mg, 1.127 mmol) and trifluoroacetic acid (6 mL) are dissolved in 12 mL DCM and stirred for 90 min at r.t. Afterwards the solvent is evaporated in vacuo. Yield >98% m/z 300 [M+H]+, rt 0.69 min, LC-MS Method V011_S01.

Step 7: Synthesis of Intermediate I-3.7

R2 (265.4 mg, 1.1 mmol) is dissolved in 5 mL DMF and treated with 1 eq DIPEA (143.6 mg). After addition of TBTU (388.5 mg, 1.21 mmol) the mixture is stirred for 20 min at r.t. I-3.6 (465 mg, 1.125 mmol) and 1.5 eq DIPEA (215.5 mg) are added and stirred for 12 h at r.t. The mixture is diluted with ethyl acetate to a volume of 60 mL, washed 2× with 1 N HCl, 2× with water, 2× with aq. Na$_2$CO$_3$ solution (10%) and 3× with water, and the organic layer is dried over MgSO$_4$. After filtration the solvent is evaporated in vacuo. Yield 82% m/z 523 [M+H]+, rt 1.05 min, LC-MS Method V011_S01.

Step 8: Synthesis of Intermediate I-3.8

To I-3.7 (470 mg, 0.899 mmol) is added 10 mL DCM and Burgess reagent R3 (535 mg, 2.248 mmol). The mixture is stirred for 12 h at r.t. and the solvent is evaporated in vacuo. The residue is dissolved in ethyl acetate, extracted 1× with 1 N HCl and 3× with water, and the organic layer is dried over MgSO$_4$. After filtration the solvent is evaporated in vacuo. Yield 99%.

Step 9: Synthesis of Example 5

I-3.8 (285 mg, 0.565 mmol) is dissolved in acetonitrile. Sodium iodide (254 mg, 1.694 mmol) and trimethylsilyl chloride (0.215 mL, 1.694 mmol) are added and the mixture is stirred for 1.5 h at r.t. After addition of 10 mL methanol and stirring for additional 20 min at r.t. the solvent is evaporated in vacuo and the residue is dissolved in acetonitrile. After filtration the product is purified by preparative HPLC (254 nm UV detection). The fractions containing the product are combined and lyohilized Yield 40% m/z 405 [M+H]+, rt 0.81 min, LC-MS Method X018_S01.

Synthesis of Starting Materials/Educts

Synthesis of
1-(4-bromo-benzenesulfonyl)-4-methyl-piperazine
(R11)

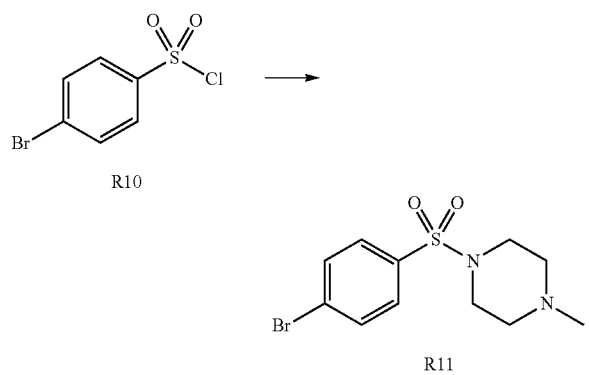

R10 (800 mg, 3.1 mmol) is dissolved in DCM, N-methyl-piperazine (313 mg, 3.1 mmol) is added and stirred for 12 h. After addition of 2 mL 1N HCl under stirring the phases are separated. The organic phase is dried over MgSO$_4$ and after filtration evaporated in vacuo. Yield: 84% m/z 319 (M+H)+.

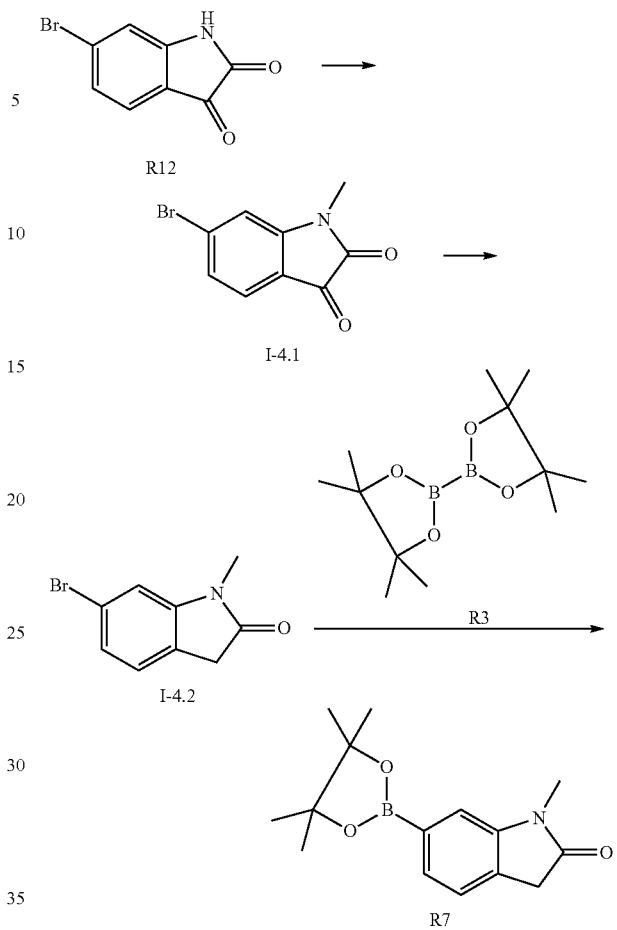

Step 1: Synthesis of Intermediate I-4.1

To R12 (25.0 g, 111 mmol) in acetonitrile (750 mL) is added MeI (15 mL, 241 mmol) and K$_2$CO$_3$ (60.0 g, 434 mmol) and the reaction mixture is stirred at 60° C. for 2 h. The reaction mixture is filtered and concentrated. Water and ethyl acetate are added to the residue. The organic layer is extracted twice with water, dried over MgSO$_4$ and concentrated. Yield 56%, m/z 240/242 [M+H]+, rt 0.48 min, LC-MS Method X001_004.

Step 2: Synthesis of Intermediate I-4.2

I-4.1 (15.0 g, 63 mmol) and hydrazine hydrate (30 mL, 618 mmol) are heated to 125° C. for 72 h. To the cool reaction mixture DCM is added and extracted with water and 1 M HCl. The organic layer is dried over MgSO$_4$ and concentrated. The crystallized residue is dissolved in DCM, methanol is added and the DCM is removed in vacuo. The crystallized product is filtered by sunction and washed with cold methanol. Yield 63%, m/z 226/228 [M+H]+, rt 1.16 min, LC-MS Method V001_003.

Step 3: Synthesis of Intermediate R7

To I-4.2 (32.0 g, 142 mmol) in anhydrous dioxane (400 mL) is added R3 (54.4 g, 241 mmol) and potassium acetate (41.6 g, 424 mmol). The mixture is purged with Argon, [1,1'-Bis(diphenylphosphino)ferrocene]dichloropalladium(II) as a complex with dichloromethane (11.2 g, 14 mmol) is added and the mixture is heated to 90° C. for 2 h. The reaction mixture is diluted with ethyl acetate and water, the organic layer is washed with water, dried over MgSO$_4$ and concentrated. The residue is purified via flash chromatography (cyclohexane/EA=70:30). Yield 72%, m/z 274 [M+H]+, rt 0.67 min, LC-MS Method VO11_S01.

The following intermediates as shown in Table 7 are synthesized in a similar fashion from the appropriate intermediates:

TABLE 7

| Intermediate | Structure of Intermediate | m/z [M + H]+ | rt (min) | LC-MS method |
| --- | --- | --- | --- | --- |
| R7.1 | | 325 [M + NH$_4$]+ | 0.30 | X018_S01 |
| R7.2 | | 285 | n.d. | n.d. |
| R7.3 | | 289 | n.d. | n.d. |
| R7.4 | | 289 | n.d. | n.d. |
| R7.5 | | 288 | 0.62 | V011_S01 |
| R7.6 | | 260 | 0.97 | V012_S01 |

TABLE 7-continued

| Intermediate | Structure of Intermediate | m/z [M + H]+ | rt (min) | LC-MS method |
|---|---|---|---|---|
| R7.7 | | 274 | 1.04 | V012_S01 |

All other boronic acid derivatives R4 and R7 are purchased or prepared by literature known procedures.

Synthesis of 5-chloromethyl-2,3-dibromo-4-fluoro-thiophene (R6)

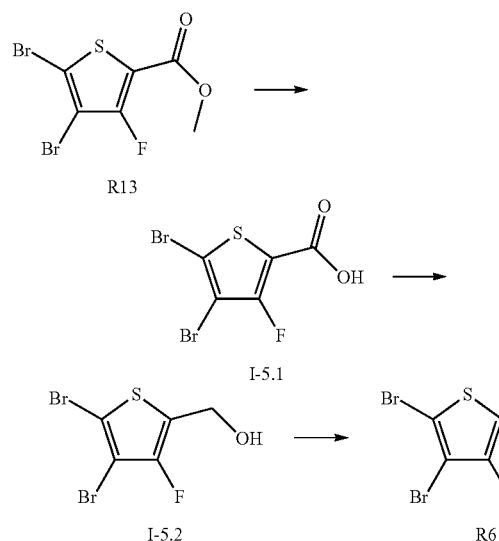

Step 1: Synthesis of Intermediate I-5.1

R13 (6400 mg, 20.128 mmol), purchased from Goldenbridge, and lithium hydroxide (2410.3 mg, 100.642 mmol) are suspended in 130 mL THF and stirred 3 h at room temperature. The mixture is diluted with water to 500 mL, acidified with 1 N HCl, extracted with diethyl ether, and the organic layer is washed 3× with water and dried over MgSO$_4$. After filtration the solvent is evaporated in vacuo. Yield: 97%.

Step 2: Synthesis of Intermediate I-5.2

I-5.1 (5950 mg mg, 19.577 mmol) is dissolved in 200 mL THF and 1,1'-Carbonyldiimidazole (3491.8 mg, 21.534 mmol) is added. After 1 h at 50° C. and 30 min at room temperature NaBH$_4$ (2221.758 mg, 58.73 mmol) is added and afterwards dropwise 50 mL water. After stirring for 2 h at room temperature the mixture is diluted with water to 800 mL and acidified with acetic acid. The solution is extracted 2× with diethyl ether, the combined organic layers are washed 2× with 1 N acetic acid, 3× with water, 2× with aq. Na$_2$CO$_3$ solution (10%) and 2× with water. The organic phase is dried over MgSO$_4$, filtrated, and the solvent is evaporated in vacuo. Yield: 92%.

The following intermediates as shown in Table 8 are synthesized in a similar fashion from the appropriate intermediates:

TABLE 8

| Intermediate | Structure | m/z [M + H] + | rt (min) | LC-MS method |
|---|---|---|---|---|
| I-5.2.1 (directly from the ester without CDI with MeOH) | | n.d. | Rf = 0.50 | Merck silica gel 60F 254 Cyclohexane/ethyl acetate 8:2 |
| I-5.2.2 (directly from the ester without CDI with MeOH) | | 265 (M + Na)+ | n.d. | n.d. |
| I-5.2.3 (directly from the ester with LiAlH$_4$ without water) | | 210 (M*+) | Rf = 0.33 | Merck silica gel 60F 254 Cyclohexane/ethyl acetate 7:3 |

TABLE 8-continued

| Intermediate | Structure | m/z [M + H] + | rt (min) | LC-MS method |
|---|---|---|---|---|
| I-5.2.4 (directly from the aldehyde without water in ethanol) | Br—⟨thiophene⟩—CH₂OH | 175/177 | 0.40 | X012_S01 |

Step 3: Synthesis or R6

I-5.2 (5200 mg, 17.934 mmol) and triethylamine (3.022 mL, 21.521 mmol) are dissolved in 50 mL DCM and treated with methanesulfonylchloride (1.458 mL, 18.831 mmol) below 5° C. After stirring for 12 h at room temperature the solvent is evaporated in vacuo and the residue is dissolved in diethyl ether and washed 2× with 1 N HCl and 3× with water. After drying over MgSO₄ and filtrating the solvent is evaporated in vacuo. Yield: 82%.

The following intermediates as shown in Table 9 are synthesized in a similar fashion from the appropriate intermediates:

TABLE 9

| Intermediate | Structure | m/z [M + H]+ | rt (min) | LC-MS method |
|---|---|---|---|---|
| R6.1 (thionyl chloride is used instead) | Br—⟨benzofuran⟩—CH₂Cl | n.d. | Rf = 0.65 | Merck silica gel 60F 254 Cyclohexane/ethyl acetate 8:2 |
| R6.2 (thionyl chloride is used instead) | Br—⟨benzothiophene⟩—CH₂Cl | 260 (M*+) | n.d. | n.d. |
| R6.3 | Br—⟨F-thiophene⟩—CH₂Cl | n.d. | Rf = 0.42 | Merck silica gel 60F 254 Cyclohexane/ethyl acetate 7:3 |
| R6.4 | Br—⟨thiophene⟩—CH₂Cl | 210 (M*+) | n.d. | n.d. |

Synthesis of (1S,2S,4R)-3-[(tert.-butoxy)carbonyl]-3-azabicyclo[2.2.1]heptane-2-carboxylate (R2)

The compound is commercially available or can be synthesized in analogy to Tararov et al, Tetrahedron Asymmetry 13 (2002), 25-28.

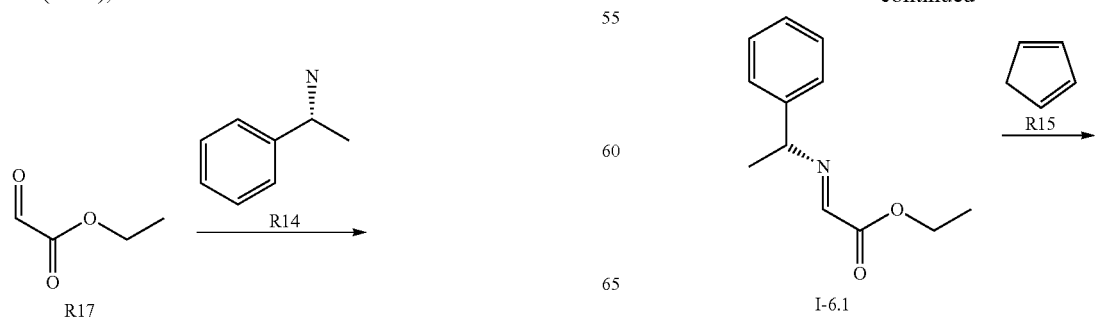

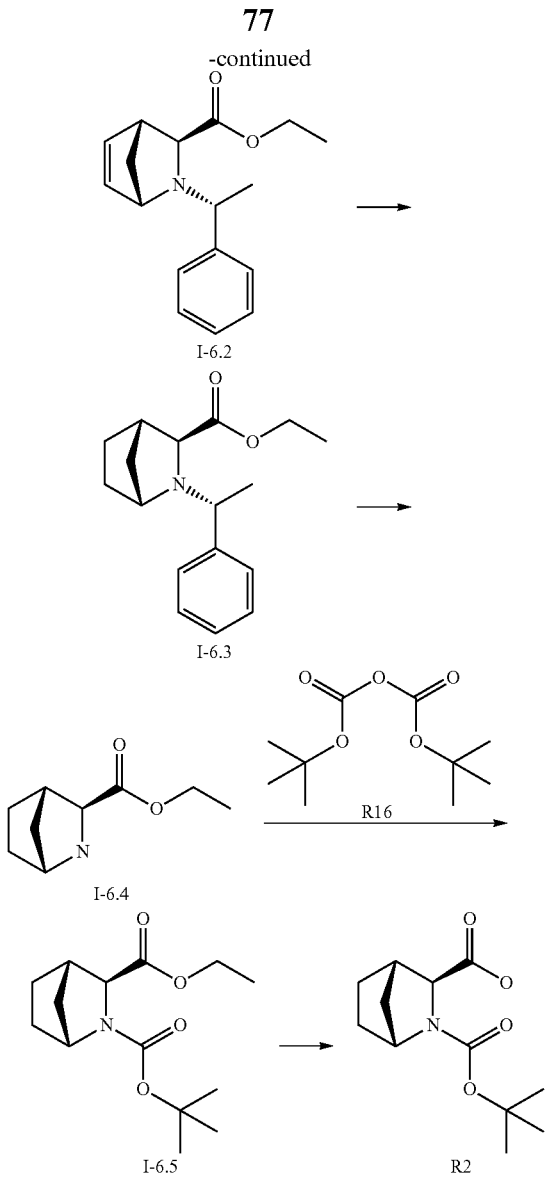

Step 1: Synthesis of Intermediate I-6.1

A solution of R17 (44.9 g, 0.44 mol), freshly distilled from a commercially available solution in toluene (at 50 mbar, 55° C.) in diethylether (300 ml) is cooled at −10° C., followed by dropwise addition of R14 (53 g, 440 mmol), keeping the temperature below 0° C. After complete addition, MgSO4*H2O (91 g, 660 mmol) is added, and the resulting mixture stirred at room temperature overnight. The mixture is filtrated, the solution phase concentrated in vacuo and the residue distilled under reduced pressure to yield I-6.1 (47 g, m/z 206 [M+H]+, rt 1.29 min, LC-MS Method V003_003). The product is used without further purification.

Step 2: Synthesis of Intermediate I-6.2

A solution of I-6.1 (47 g; 229 mmol) and R15 (30 g; 458 mmol) (freshly distilled from dicyclopentadien) in DMF (150 ml) and 120 μl water is cooled to 0° C., before TFA (18 ml; 234 mmol) is added dropwise. The mixture is stirred overnight at room temperature, then added to a solution of 40 g NaHCO3 in 1200 ml water and extracted with diethylether. The organic layer is separated, washed subsequently with aqueous NaHCO3 and water, dried over MgSO4, and concentrated in vacuo. The residue is worked up by column chromatography on silica (cyclohexane/ethyl acetate=9:1) to yield I-6.2 (Yield 52% m/z 272 [M+H]+, rt 0.42 min, LC-MS Method X001_004)

Step 3: Synthesis of Intermediate I-6.3

To a solution of I-6.2 (24.8 g, 91 mmol) in ethanol (250 ml), Raney-nickel is added (2.5 g) and reacted at 50 psi under a hydrogen atmosphere at room temperature. The catalyst is filtered of, the is solution concentrated in vacuo and the residue worked up by chromatography on silica (cyclohexane/ethyl acetate 9:1). After evaporation of the organic solvent, the obtained product is redissolved in diethylether and triturated with solution of HCl in dioxane, concentrated in vacuo, redissolved in 200 ml ethanol and concentrated in vacuo to yield I-6.3: (Yield 78% m/z 274 [M+H]+, rt 0.42 min, LC-MS Method X001_004).

Step 4: Synthesis of Intermediate I-6.4

To a solution of I-6.3 (22 g, 71 mmol) in ethanol (250 ml), 10% Pd/C is added (2.5 g) and reacted at 15 bar under a hydrogen atmosphere at room temperature. The catalyst is filtered of, the solution concentrated in vacuo. The residue is washed with diisopropylether to yield I-6.4. (Yield 98% m/z 170 [M+H]+, rt 0.48 min, LC-MS Method V001_007).

Step 5: Synthesis of Intermediate I-6.5

To I-6.4 in a solution of triethylamin (24.6 ml), THF (150 ml) and water (2 ml), R16 (15.9 g; 73 mmol) is added and the resulting mixture stirred for 40 hours at room temperature, then concentrated in vacuo. Ethyl acetate is added to the residue, subsequently extracted with water, 1 N acidic acid and water, before the organic layer is dried over MgSO4 and concentrated in vacuo to yield I-6.5. (Yield 95% m/z 270 [M+H]+, rt 1.33 min, LC-MS Method V003_003).

Step 6: Synthesis of R2

A mixture of I-6.5 (16.9 g; 63 mmol) in acetone (152 ml), water (50 ml) and lithium hydroxide (3 g, 126 mmol) is stirred overnight at room temperature. Water (100 ml) was added, the volume reduced in vacuo before cooling to 0° C. followed by the addition of 1N aqueous HCl to acidify to a pH of 2-3, immediately followed by extraction with ethyl acetate. The organic layer was washed with water, dried (MgSO4) and concentrated. To the residue, dichloromethane (100 ml) and cyclohexane (100 ml) was added, the volume reduced in vacuo by half and the mixture temperated at 15° C. The precipitate was filtered of, washed with cyclohexane to yield R2 (Yield 66%, m/z 242 [M+H]+).

EXAMPLES (rt=retention time) Stereochemistry at the carbon atom adjacent to the nitrile group is assigned: Stereo bond means S-isomer, non-stereo bond means 1:1 mixture of stereoisomers.

TABLE 10
| Example | Structure | Educt | Syn. Method | Yield [%] |
|---|---|---|---|---|
| 1 | 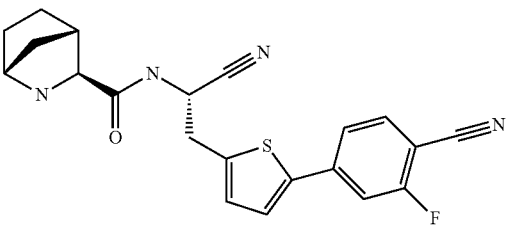 [SMILES: N#Cc1ccc(-c2ccc(C[C@@H](C#N)NC(=O)[C@H]3N[C@@H]4CC[C@H]3C4)s2)cc1F] | I-1.5 | A | 40 |
| 2 | 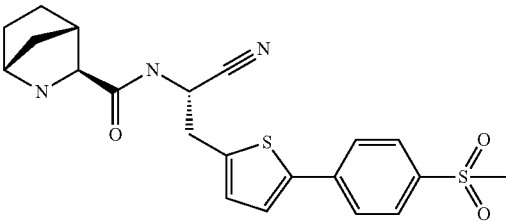 [SMILES: CS(=O)(=O)c1ccc(-c2ccc(C[C@@H](C#N)NC(=O)[C@H]3N[C@@H]4CC[C@H]3C4)s2)cc1] | I-1.5.13 | A | 26 |
| 3 | 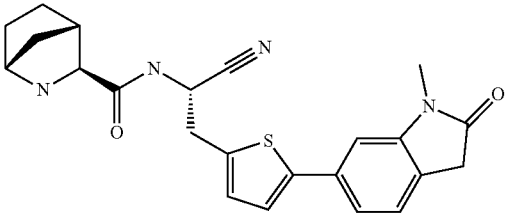 [SMILES: CN1C(=O)Cc2ccc(-c3ccc(C[C@@H](C#N)NC(=O)[C@H]4N[C@@H]5CC[C@H]4C5)s3)cc21] | I-1.5.1 | A | 47 |
| 4 | 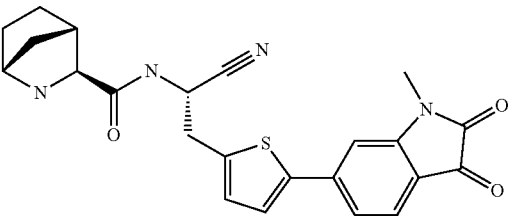 [SMILES: CN1C(=O)C(=O)c2ccc(-c3ccc(C[C@@H](C#N)NC(=O)[C@H]4N[C@@H]5CC[C@H]4C5)s3)cc21] | I-1.5.14 | A | 40 |
| 5 | 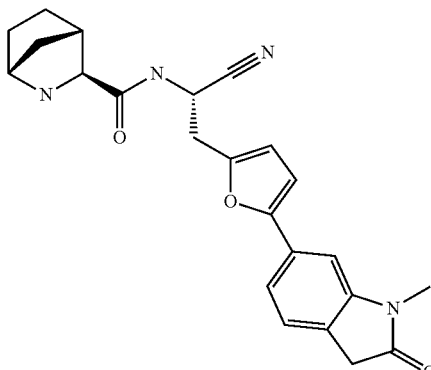 | 1-3.8 | C | 40 |

TABLE 10-continued

| Example | Structure | Educt | Syn. Method | Yield [%] |
|---------|-----------|-------|-------------|-----------|
| 6 | 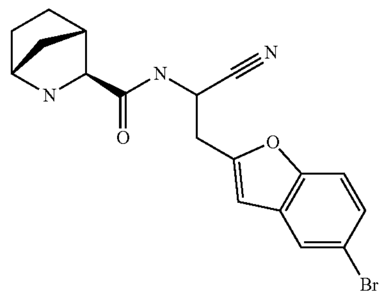 [SMILES: N#CC(Cc1cc2cc(Br)ccc2o1)NC(=O)[C@H]1N[C@@H]2CC[C@H]1C2] | I-2.3.2 | B | 63 |
| 7 | 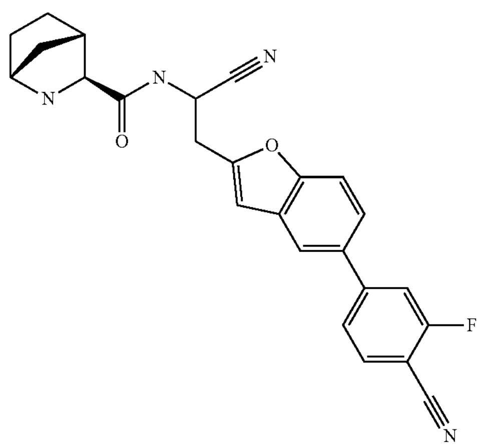 [SMILES: N#Cc1ccc(-c2ccc3oc(CC(C#N)NC(=O)[C@H]4N[C@@H]5CC[C@H]4C5)cc3c2)cc1F] | I-2.4.2 | B | 86 |
| 8 | 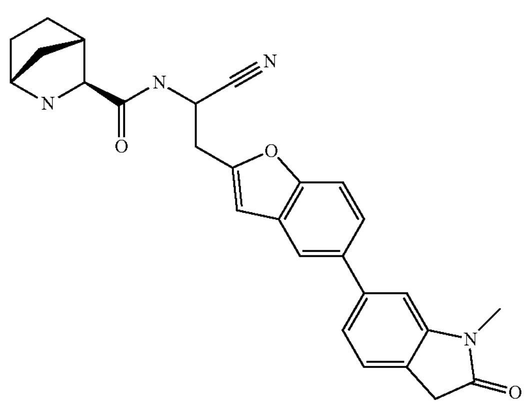 [SMILES: CN1C(=O)Cc2ccc(-c3ccc4oc(CC(C#N)NC(=O)[C@H]5N[C@@H]6CC[C@H]5C6)cc4c3)cc21] | I-2.4.3 | B | 29 |
| 9 | 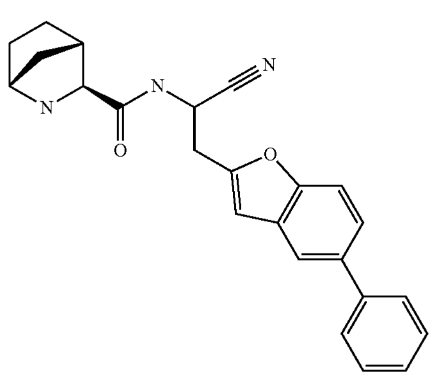 [SMILES: N#CC(Cc1cc2cc(-c3ccccc3)ccc2o1)NC(=O)[C@H]1N[C@@H]2CC[C@H]1C2] | I-2.4.4 | B | 25 |

TABLE 10-continued

| Example | Structure | Educt | Syn. Method | Yield [%] |
|---------|-----------|-------|-------------|-----------|
| 10 | 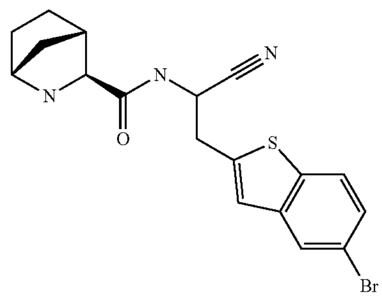 [SMILES: N#CC(Cc1cc2cc(Br)ccc2s1)NC(=O)[C@H]1N[C@@H]2CC[C@H]1C2] | I-2.3.3 | B | 59 |
| 11 | 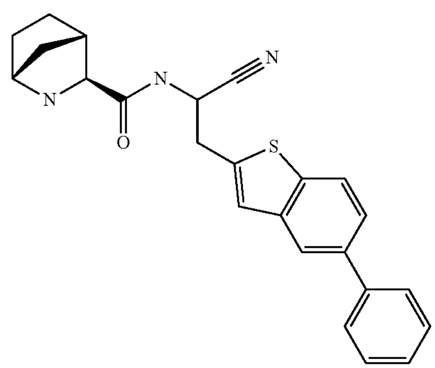 [SMILES: N#CC(Cc1cc2cc(-c3ccccc3)ccc2s1)NC(=O)[C@H]1N[C@@H]2CC[C@H]1C2] | I-2.4.5 | B | 49 |
| 12 | 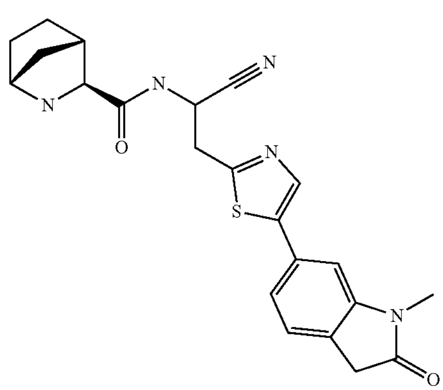 [SMILES: CN1C(=O)Cc2ccc(-c3cnc(CC(C#N)NC(=O)[C@H]4N[C@@H]5CC[C@H]4C5)s3)cc21] | I-2.4.9 | B | 38 |
| 13 | 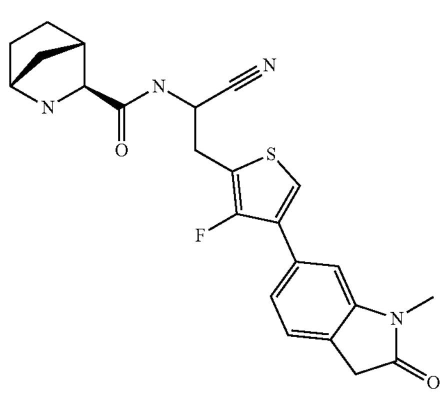 [SMILES: CN1C(=O)Cc2ccc(-c3csc(CC(C#N)NC(=O)[C@H]4N[C@@H]5CC[C@H]4C5)c3F)cc21] | I-2.4.7 | B | 12 |

TABLE 10-continued
| Example | Structure | Educt | Syn. Method | Yield [%] |
|---|---|---|---|---|
| 14 | 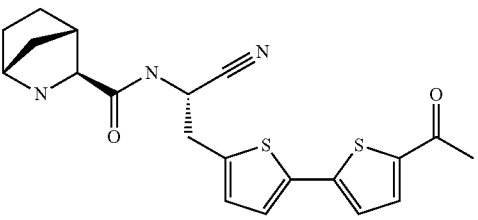 [SMILES: CC(=O)c1ccc(-c2ccc(C[C@@H](C#N)NC(=O)[C@H]3N[C@@H]4CC[C@H]3C4)s2)s1] | I-1.5.2 | A | 34 |
| 15 | 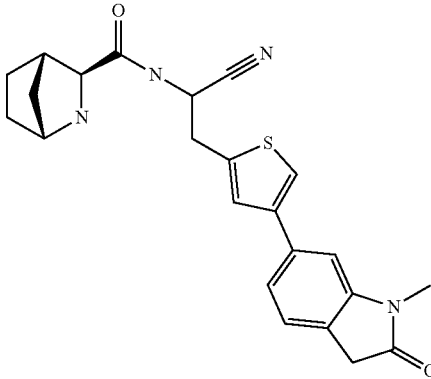 [SMILES: CN1C(=O)Cc2ccc(-c3csc(CC(C#N)NC(=O)[C@H]4N[C@@H]5CC[C@H]4C5)c3)cc21] | I-2.4.8 | B | 37 |
| 16 | 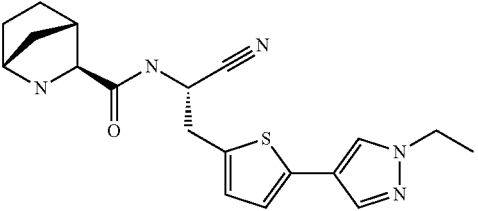 [SMILES: CCn1cc(-c2ccc(C[C@@H](C#N)NC(=O)[C@H]3N[C@@H]4CC[C@H]3C4)s2)cn1] | I-1.5.3 | A | 40 |
| 17 | 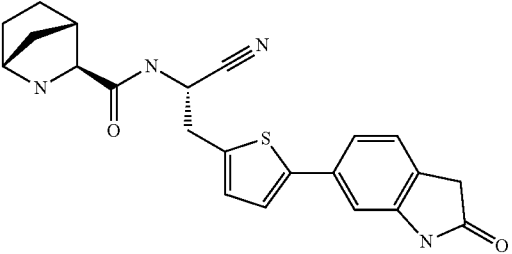 [SMILES: N#C[C@H](Cc1ccc(-c2ccc3c(c2)NC(=O)C3)s1)NC(=O)[C@H]1N[C@@H]2CC[C@H]1C2] | I-1.5.4 | A | 59 |
| 18 | 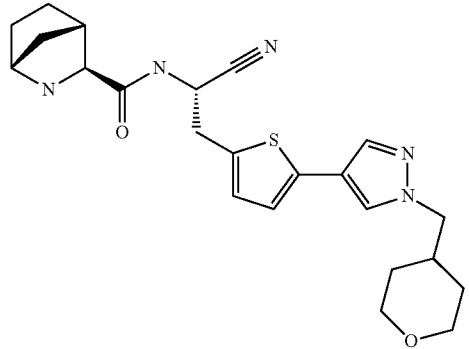 [SMILES: N#C[C@H](Cc1ccc(-c2cnn(CC3CCOCC3)c2)s1)NC(=O)[C@H]1N[C@@H]2CC[C@H]1C2] | I-1.5.5 | A | 25 |

TABLE 10-continued
| Example | Structure | Educt | Syn. Method | Yield [%] |
|---|---|---|---|---|
| 19 | 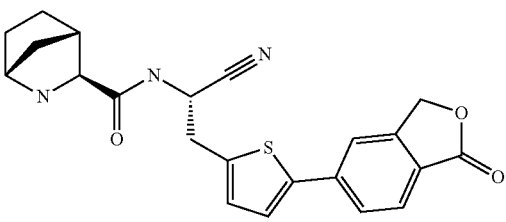 [SMILES: N#C[C@H](Cc1ccc(-c2ccc3c(c2)COC3=O)s1)NC(=O)[C@H]1N[C@@H]2CC[C@H]1C2] | I-1.5.6 | A | 51 |
| 20 | 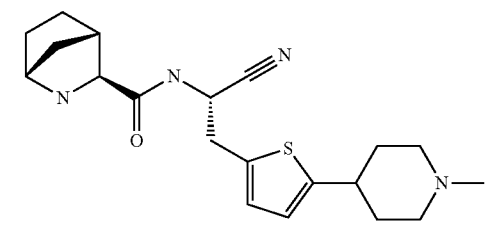 [SMILES: CN1CCC(c2ccc(C[C@@H](C#N)NC(=O)[C@H]3N[C@@H]4CC[C@H]3C4)s2)CC1] | I-1.5.8 | A | 31 |
| 21 | 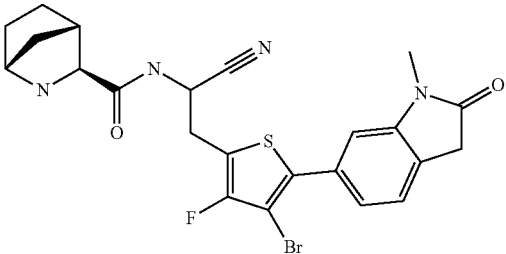 [SMILES: CN1C(=O)Cc2ccc(-c3sc(CC(C#N)NC(=O)[C@H]4N[C@@H]5CC[C@H]4C5)c(F)c3Br)cc21] | I-2.4 | B | 67 |
| 22 | 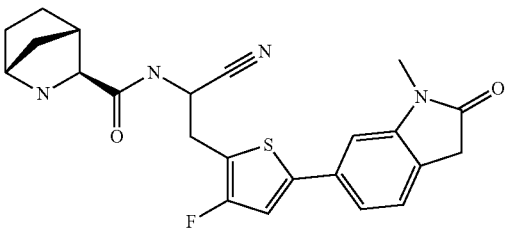 [SMILES: CN1C(=O)Cc2ccc(-c3cc(F)c(CC(C#N)NC(=O)[C@H]4N[C@@H]5CC[C@H]4C5)s3)cc21] | I-2.5 | B | 17 |
| 23 | 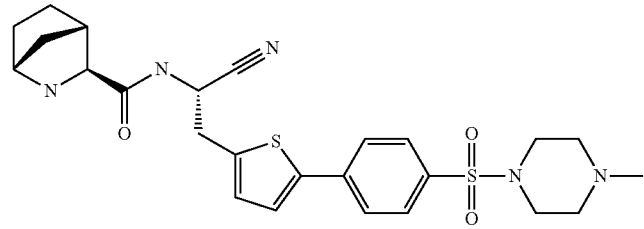 [SMILES: CN1CCN(S(=O)(=O)c2ccc(-c3ccc(C[C@@H](C#N)NC(=O)[C@H]4N[C@@H]5CC[C@H]4C5)s3)cc2)CC1] | I-1.5.9 | A | 76 |
| 24 | 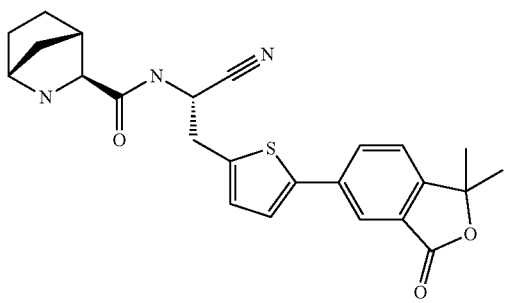 [SMILES: CC1(C)OC(=O)c2cc(-c3ccc(C[C@@H](C#N)NC(=O)[C@H]4N[C@@H]5CC[C@H]4C5)s3)ccc21] | I-1.5.10 | A | 57 |

TABLE 10-continued

| Example | Structure | Educt | Syn. Method | Yield [%] |
|---|---|---|---|---|
| 25 | 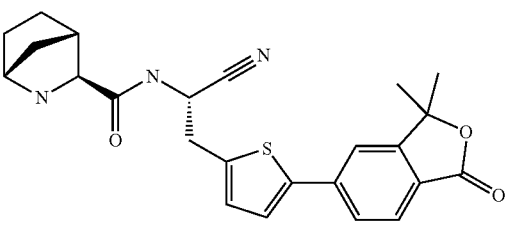 [SMILES: CC1(C)OC(=O)c2ccc(-c3ccc(C[C@@H](C#N)NC(=O)[C@H]4N[C@@H]5CC[C@H]4C5)s3)cc21] | I-1.5.11 | A | 90 |
| 26 | 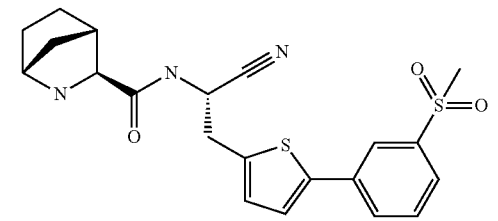 [SMILES: CS(=O)(=O)c1cccc(-c2ccc(C[C@@H](C#N)NC(=O)[C@H]3N[C@@H]4CC[C@H]3C4)s2)c1] | I-1.5.12 | A | 66 |

Analytical Data of Examples

| # | m/z [M + H]+ | rt [min] | LC-MS-Method |
|---|---|---|---|
| 1 | 395 | 0.55 | X001_004 |
| 2 | 430 | 0.38 | X012_S01 |
| 3 | 421 | 0.51 | X001_004 |
| 4 | 435 | 0.85 | V012_S01 |
| 5 | 405 | 0.81 | X018_S01 |
| 6 | 388/390 | 0.48 | X012_A15 |
| 7 | 429 | 0.52 | X012_A15 |
| 8 | 455 | 0.46 | X012_A15 |
| 9 | 386 | 0.55 | X012_S01 |
| 10 | 404/406 | 0.51 | X012_S01 |
| 11 | 402 | 1.29 | V011_S01 |
| 12 | 422 | 0.76 | V012_S01 |
| 13 | 439 | 0.82 | V018_S01 |
| 14 | 400 | 0.84 | V012_S01 |
| 15 | 421 | 0.39 | X012_S01 |
| 16 | 370 | 0.78 | V012_S01 |
| 17 | 407 | 0.78 | V012_S01 |
| 18 | 440 | 0.81 | V012_S01 |
| 19 | 407 | 0.84 | V012_S01 |
| 20 | 373 | 0.61 | V012_S01 |
| 21 | 518/520 | 0.45 | X012_S01 |
| 22 | 439 | 0.41 | X012_S01 |
| 23 | 514 | 0.79 | V012_S01 |
| 24 | 436 | 0.95 | V012_S01 |
| 25 | 436 | 0.93 | V012_S01 |
| 26 | 430 | 0.39 | X012_S01 |

Abbreviations

| | |
|---|---|
| ACN | acetonitrile |
| aq. | aqueous |
| BOC | tert. butyloxycyrbonyle- |
| d | day |
| DCM | dichloromethane |
| DIPEA | n,n-diisopropylethylamine |
| DIPE | diisopropyl ether |
| DMAP | 4-dimethylaminopyridine |
| DMF | n,n-dimethylformamide |
| DMSO | dimethyl sulfoxide |
| EA | ethyl acetate |
| FA | formic acid |
| h | hour |
| HATU | o-(7-azabenzotriazol-1-yl)-N,N,N',N'-tetramethyluronium hexafluoro-phosphate |
| LiOH | lithium hydroxide |
| MeOH | methanol |
| Rf | Ratio of fronts |
| RT, r.t. | room temperature e.g. 15-25° C. |
| rt | retention time |
| sat. | saturated |
| SI | trimethylsilyl iodide |
| TBME | tert-butyl methyl ether |
| TBTU | o-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | toluene sulfonic acid |

Pharmacological Data

Other features and advantages of the present invention will become apparent from the following more detailed examples which illustrate, by way of example, the principles of the invention.

Inhibition of Human DPPI (Cathepsin C)

Materials: Microtiterplates (Optiplate-384 F) were purchased from PerkinElmer (Prod. No. 6007270). The substrate Gly-Arg-AMC was from Biotrend (Prod.-No. 808756 Custom peptide). Bovine serum albumin (BSA; Prod. No. A3059) and Dithiothreitol (DTT; Prod. No D0632) were from Sigma. TagZyme buffer was from Riedel-de-Haen (Prod.-No. 04269), NaCl was from Merck (Prod.-No. 1.06404.1000) and morpholinoethane sulfonic acid (MES), was from Serva (Prod.-No. 29834). The DPP1 inhibitor Gly-Phe-DMK was purchased from MP Biomedicals (Prod.-No. 03DK00625). The recombinant human DPPI was purchased from Prozymex. All other materials were of highest grade commercially available.

The following buffers were used: MES buffer: 25 mM MES, 50 mM NaCl, 5 mM DTT, adjusted to pH 6.0, containing 0.1% BSA; TAGZyme Buffer: 20 mM NaH$_2$PO$_4$, 150 mM NaCl adjusted to pH 6.0 with HCl Assay conditions: The recombinant human DPPI was diluted in TAGZyme buffer to 1 U/ml (38.1 µg/ml, respectively), and then activated by mixing in a 1:2 ratio with a Cysteamine aqueous solution (2 mM) and incubating for 5 min at room temperature.

Five uL test compound (final concentration 0.1 nM to 100 µM) in aqua bidest (containing 4% DMSO, final DMSO concentration 1%) were mixed with 10 µL of DPPI in MES buffer (final concentration 0.0125 ng/µL) and incubated for 10 min. Then, 5 µL of substrate in MES buffer (final concentration 50 µM) were added. The microtiter plates were then incubated at room temperature for 30 min. Then, the reaction was stopped by adding 10 µL of Gly-Phe-DMK in MES-buffer (final concentration 1 µM). The fluorescence in the wells was determined using a Molecular Devices SpectraMax M5 Fluorescence Reader (Ex 360 nm, Em 460 nm) or an Envision Fluorescence Reader (Ex 355 nm, Em 460 nm).

Each assay microtiter plate contained wells with vehicle controls (1% DMSO in bidest+0.075% BSA) as reference for non-inhibited enzyme activity (100% Ctl; high values) and wells with inhibitor (Gly-Phe-DMK, in bidest+1% DMSO+ 0.075% BSA, final concentration 1 µM) as controls for background fluorescence (0% Ctl; low values).

The analysis of the data was performed by calculating the percentage of fluorescence in the presence of test compound in comparison to the fluorescence of the vehicle control after subtracting the background fluorescence using the following formula:

(RFU(sample)−RFU(background))*100/(RFU(control)−RFU(background))

Data from these calculations were used to generate $IC_{50}$ values for inhibition of DPPI, respectively.

| # | Inhibition of DPPI Ki [µM] |
|---|---|
| 1 | 0.0137 |
| 2 | 0.0173 |
| 3 | 0.0032 |
| 4 | 0.0021 |
| 5 | 0.1765 |
| 6 | 0.0641 |
| 7 | 0.0393 |
| 8 | 0.1036 |
| 9 | 0.062 |
| 10 | 0.0358 |
| 11 | 0.0728 |
| 12 | 0.0149 |
| 13 | 0.0617 |
| 14 | 0.0134 |
| 15 | 0.0419 |
| 16 | 0.0171 |
| 17 | 0.0042 |
| 18 | 0.027 |
| 19 | 0.0009 |
| 20 | 0.0379 |
| 21 | 0.0036 |
| 22 | 0.0022 |
| 23 | 0.0029 |
| 24 | 0.0219 |
| 25 | 0.004 |
| 26 | 0.0167 |

Inhibition of Human Cathepsin K

Materials: Microtiterplates (Optiplate-384 F were purchased from PerkinElmer (Prod. No. 6007270). The substrate Z-Gly-Pro-Arg-AMC was from Biomol (Prod.-No. P-142). L-Cysteine (Prod. No. 168149) was from Sigma. Sodium actetate was from Merck (Prod.-No. 6268.0250), EDTA was from Fluka (Prod.-No. 03680). The inhibitor E-64 was purchased from Sigma (Prod.-No. E3132). The recombinant human Cathepsin K proenzyme was purchased from Biomol (Prod. No. SE-367). All other materials were of highest grade commercially available.

The following buffers were used: Activation buffer: 32.5 mM sodium acetate, adjusted to pH 3.5 with HCl; Assay buffer: 150 mM sodium acetate, 4 mM EDTA, 20 mM L-Cysteine, adjusted to pH 5.5 with HCl, Assay conditions: To activate the proenzyme, 5 µl procathepsin K were mixed with 1 ul activation buffer, and incubated at room temperature for 30 min.

5 µL test compound (final concentration 0.1 nM to 100 µM) in aqua bidest (containing 4% DMSO, final DMSO concentration 1%) were mixed with 10 uL of Cathepsin K in assay buffer (final concentration 2 ng/µL) and incubated for 10 min. Then 5 µL of substrate in assay buffer (final concentration 12.5 µM) were added. The plates were then incubated at room temperature for 60 min. Then, the reaction was stopped by adding 10 µL of E64 in assay buffer (final concentration 1 µM). The fluorescence in the wells was determined using a Molecular Devices SpectraMax M5 Fluorescence Reader (Ex 360 nm, Em 460 nm).

Each assay microtiter plate contains wells with vehicle controls (1% DMSO in bidest) as reference for non-inhibited enzyme activity (100% Ctl; high values) and wells with inhibitor (E64 in bidest+1% DMSO, final concentration 1 µM) as controls for background fluorescence (0% Ctl; low values). The analysis of the data was performed by calculating the percentage of fluorescence in the presence of test compound in comparison to the fluorescence of the vehicle control after subtracting the background fluorescence:

(RFU(sample)−RFU(background))*100/(RFU(control)−RFU(background))

Data from these calculations were used to generate $IC_{50}$ values for inhibition of Cathepsin K, respectively.

Combinations

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Non-steroidal anti-inflammatory agents (NSAIDs), CRTH2 antagonists, DP1-receptor modulators, Thromboxane receptor antagonists, CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, $CXCR^3$ antagonists, $CXCR^4$ antagonists, $CXCR^2$ antagonists, CXCR$^1$ antagonists, CXCR5 antagonists, CXCR6 antagonists, CX3CR$^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Matriptase-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, NE-inhibitors, MMP9 inhibitors, MMP12 inhibitors, but also combinations of two or three active substances.

Preferred are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, NE-inhibitors, MMP9 inhibitors, MMP12 inhibitors, but also combinations of two or three active substances, i.e.:

Betamimetics with corticosteroids, PDE4-inhibitors, CRTH2-inhibitors or LTD4-antagonists,
Anticholinergics with betamimetics, corticosteroids, PDE4-inhibitors, CRTH2-inhibitors or LTD4-antagonists,
Corticosteroids with PDE4-inhibitors, CRTH2-inhibitors or LTD4-antagonists
PDE4-inhibitors with CRTH2-inhibitors or LTD4-antagonists
CRTH2-inhibitors with LTD4-antagonists.

Indications

The compounds of the invention and their pharmaceutically acceptable salts have activity as pharmaceuticals, in particular as inhibitors of dipeptidyl peptidase I activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency, bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, polyangiitis (Wegener Granulomatosis) and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis;cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and *mycobacterium avium*, leprosy; other infectious diseases, such as fungal diseases, chlamydia, *Candida, aspergillus*, cryptococcal meningitis, *Pneumocystis carnii*, cryptosporidiosis, histoplasmosis, toxoplasmosis, trypanosome infection and leishmaniasis.

9. pain: Recent literature data from Cathepsin C-deficient mice point to a modulatory role of Cathepsin C in pain sensation. Accordingly, inhibitors of Cathepsin C may also be useful in the clinical setting of various form of chronic pain, e.g. inflammatory or neuropathic pain.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:
1. A compound of formula 1

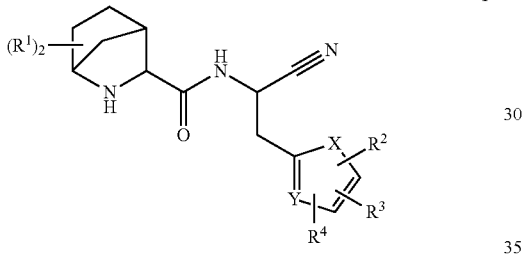

wherein
X is selected from among S and O;
Y is selected from among N and CH;
$R^1$ is independently selected from among H, $C_{1-6}$-alkyl-, halogen, HO—, $C_{1-6}$-alkyl-O—, $H_2N$—, $C_{1-6}$-alkyl-HN—, $(C_{1-6}$-alkyl$)_2N$— and $C_{1-6}$-alkyl-C(O)HN—;
or two $R^1$ are together $C_{1-4}$-alkylene;
$R^2$ is selected from among
  $R^{2.1}$;
  aryl-; optionally substituted with one, two or three residues independently selected from $R^{2.1}$; optionally substituted with one $R^{2.3}$;
  $C_{5-10}$-heteroaryl-; containing one, two, three or four heteroatoms independently selected from among S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$;
  $C_{5-10}$-heterocyclyl-; containing one, two, three or four heteroatoms independently selected from among S, S(O), S(O)$_2$, O and N, wherein the ring is fully or partially saturated, wherein carbon atoms of the ring are optionally and independently from each other substituted with one, two or three or four $R^{2.1}$; wherein nitrogen atoms of the ring are optionally and independently from each other substituted with one, two or three $R^{2.2}$; wherein a carbon atom of the ring is optionally substituted with one $R^{2.3}$ or one $R^{2.5}$; a nitrogen atom of the ring is optionally substituted with one $R^{2.4}$ or $R^2$ and $R^4$ are together with two adjacent carbon atoms of the heteroaryl ring a 5- or 6-membered aryl or heteroaryl, containing one, two or three heteroatoms independently selected from among S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$;

$R^{2.1}$ is independently selected from among H, halogen, NC—, O═, HO—, H-A-, H-A-$C_{1-6}$-alkylene-, $R^{2.1.1}$-A-, $C_{1-6}$-alkyl-A-, $C_{3-8}$-cycloalkyl-A-, $C_{1-6}$-haloalkyl-A-, $R^{2.1.1}$—$C_{1-6}$-alkyl-A-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$—$C_{1-6}$-alkylene-A-$C_{1-6}$-alkylene-, $R^{2.1.1}$-A-$C_{1-6}$-alkylene-, HO—$C_{1-6}$-alkylene-A-, HO—$C_{1-6}$-alkylene-A-$C_{1-6}$-alkylene-, $C_{1-6}$-alkyl O—$C_{1-6}$-alkylene-A- and $C_{1-6}$-alkyl-O—$C_{1-6}$-alkylene-A-$C_{1-6}$-alkylene- $R^{2.1.1}$ is independently selected from among
  aryl-; optionally substituted independently from each other with one, two or three $R^{2.1.1.1}$;
  $C_{5-10}$-heteroaryl-; containing one, two, three or four heteroatoms independently selected from among S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
  $C_{5-10}$-heterocyclyl-; containing one, two, three or four heteroatoms independently selected from among S, S(O), S(O)$_2$, O and N, wherein the ring is fully or partially saturated, wherein carbon atoms of the ring are optionally and independently from each other substituted with one, two or three or four $R^{2.1.1.1}$; wherein nitrogen atoms of the ring are optionally and independently from each other substituted with one, two or three $R^{2.1.1.2}$;

$R^{2.1.1.1}$ is independently selected from among halogen, HO—, O═, $C_{1-6}$-alkyl-, $C_{1-6}$-alkyl-O—, $C_{1-6}$-haloalkyl- and $C_{1-6}$-haloalkyl-O— and $C_{3-8}$-cycloalkyl-;

$R^{2.1.1.2}$ is independently selected from among O═, $C_{1-6}$-alkyl-, $C_{1-6}$-haloalkyl-; $C_{3-8}$-cycloalkyl-, $C_{1-6}$-alkyl-O—$C_{1-6}$-alkyl-, H(O)C—, $C_{1-6}$-alkyl-(O)C—, tetrahydrofuranylmethyl- and tetrahydropyranylmethyl-;

$R^{2.2}$ is independently selected from among H-A-$C_{1-6}$-alkylene-, $C_{3-8}$-cycloalkyl-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $C_{1-6}$-alkyl-S(O)$_2$—, $C_{1-6}$-alkyl-C(O)— and $R^{2.1.1}$-A-;

$R^{2.3}$ and $R^4$ are together selected from
among —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, $R^{2.3}$, $R^{2.3}$,—C($R^{2.3.2}$)═C($R^{2.3.2}$)—, —C═N—, —N═C—, —C($R^{2.3.2}$)$_2$—O—, —O—C($R^{2.3.2}$)$_2$—, —C($R^{2.3.2}$)$_2$ N($R^{2.3.1}$)—, —N($R^{2.3.1}$)C($R^{2.3.2}$)$_2$— and —$C_{1-4}$-alkylene-;

$R^{2.3.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and, ($C_{1-4}$-alkyl)$_2$N—$C_{1-4}$-alkylene-;

$R^{2.3.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4}$ and $R^4$ are together selected from
among —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —C($R^{2.4.2}$)$_2$N($R^{2.4.1}$)—, —N($R^{2.4.1}$)C($R^{2.4.2}$)$_2$— and —$C_{1-4}$-alkylene-; and $R^{2.4.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.5}$ and $R^4$ are together selected from among —C($R^{2.5.1}$)=, =C($R^{2.5.1}$)— and —N=; and $R^{2.5.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^3$ is H or F;

$R^4$ is independently selected from among H, F, Cl, Br, phenyl-$H_2C$—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, $C_{1-6}$-alkyl-HN—$C_{1-4}$-alkylene- and ($C_{1-6}$-alkyl)$_2$-HN—$C_{1-4}$-alkylene-;

A is a bond or independently selected from
among —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=)S(O)—, —S(=N$R^5$)$_2$—N($R^5$)—, —N($R^5$)(N$R^5$=)$_2$S—, —C($R^5$)=C($R^5$)—, —C(O)O—, —OC(O)—, —C(O)—, —S(O)—, —S(O)$_2$—, —S(=N$R^5$)—, —S(O)(=N$R^5$)—, —S(=N$R^5$)$_2$—, —($R^5$)(O)S=N—, —($R^5$N=)(O)S— and —N=(O)($R^5$)S—;

$R^5$ is independently selected from among H, $C_{1-6}$-alkyl- and NC—;

or a salt thereof.

2. The compound of formula 1, according to claim 1, wherein $R^1$ is $R^{1.a}$ and $R^{1.a}$ is independently selected from among H, $C_{1-4}$-alkyl-, F and HO—.

3. The compound of formula 1, according to claim 1, wherein $R^4$ is $R^{4.a}$ and $R^{4.a}$ is H, F, Cl, Br, phenyl-$H_2C$—O—, HO—, $C_{1-4}$-alkyl-, $C_{1-4}$-haloalkyl-, $C_{3-6}$-cycloalkyl-$C_{1-4}$-alkyl-O— and $C_{1-4}$-haloalkyl-O—.

4. The compound of formula 1, according to claim 1, wherein $R^4$ is $R^{4.b}$ and $R^{4.b}$ is H or F.

5. The compound of formula 1, according to claim 1, wherein A is $A^a$ and $A^a$ is a bond or independently selected from
among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$—, —($R^5$)(O)S=N—, —($R^5$N=)(O)S— and —N=(O)($R^5$)S— and $R^5$ is $R^{5.a}$ and $R^{5.a}$ is independently selected from among H, $C_{1-4}$-alkyl- and NC—.

6. The compound of formula 1, according to claim 1, wherein $R^2$ is $R^{2.1}$ and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among
aryl-, optionally substituted independently from each other with one, two or three residues independently selected from $R^{2.1.1.1}$;
$C_{5-10}$-heteroaryl-, containing one, two, three or four heteroatoms selected independently from S, S(O), S(O)$_2$, O or N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
$C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl, H(O)C—, $C_{1-4}$-alkyl-(O)C—, tetrahydrofuranylmethyl- and tetrahydropyranylmethyl.

7. The compound of formula 1, according to claim 1, wherein $R^2$ is $R^{2.d}$ and $R^{2.d}$ is phenyl; optionally substituted with one, two or three residues independently selected from $R^{2.1}$ and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among
aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;

$C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl.

8. The compound of formula 1, according to claim 1, wherein $R^2$ is $R^{2-q}$ and $R^{2-q}$ is selected from among formulas (b1), (c1), (d1), (e1), (f1) and (g1),

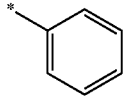
(b1)

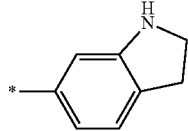
(c1)

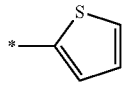
(d1)

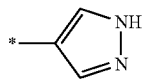
(e1)

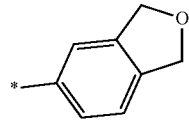
(f1)

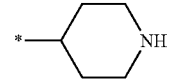
(g1)

wherein carbon atoms of the ring are optionally and independently from each other substituted with one, two or three $R^{2.1}$; wherein nitrogen atoms of the ring are optionally and independently from each other substituted with one, two or three $R^{2.2}$, $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;

$C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

9. The compound of formula 1, according to claim 1, wherein $R^2$ is $R^{2,j}$ and $R^{2,j}$ is selected from among
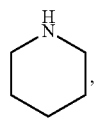
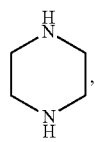
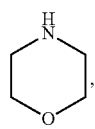
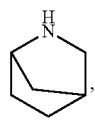
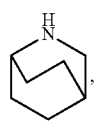
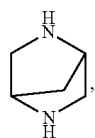
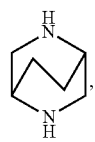
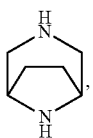
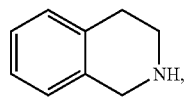
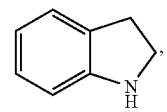
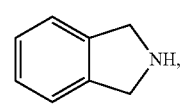
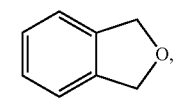
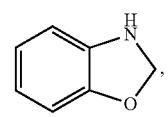
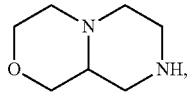
and
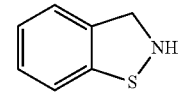
wherein carbon atoms of the ring are optionally and independently from each other substituted with one, two or three $R^{2.1}$, wherein possibly available nitrogen atoms of the ring are optionally and independently from each other substituted with $R^{2.2}$; and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1a}$ and $R^{2.1.1.a}$ is selected from among

- aryl-, optionally substituted independently from each other with one, two or three residues independently selected from $R^{2.1.1.1}$;
- $C_{5-10}$-heteroaryl-, containing one, two, three or four heteroatoms selected independently from S, S(O), $S(O)_2$, O or and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
- $C_{5-10}$-heterocyclyl-, containing one, two, three or four heteroatoms selected independently from S, S(O), $S(O)_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-$S(O)_2$—, $C_{1-4}$-alkyl-C(O)— and $R^{2.1.1}$-A-.

10. The compound of formula 1, according to claim 1, wherein $R^2$ is $R^{2.m}$ and $R^{2.m}$ is together with $R^4$ and two adjacent carbon atoms of the heteroaryl ring a 5- or 6-membered aryl or heteroaryl, containing one, two or three heteroatoms independently selected from among S, S(O), $S(O)_2$, O and N, wherein carbon atoms of the ring are optionally and independently from each other substituted with one, two or three $R^{2.1}$, wherein possibly available nitrogen atoms of the ring are optionally and independently from each other substituted with one, two or three $R^{2.2}$; and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from

- aryl-, optionally substituted independently from each other with one, two or three residues independently selected from $R^{2.1.1.1}$;
- $C_{5-10}$-heteroaryl-, containing one, two, three or four heteroatoms selected independently from S, S(O), $S(O)_2$, O or N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
- $C_{5-10}$-heterocyclyl-, containing one, two, three or four heteroatoms selected independently from S, S(O), $S(O)_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-$S(O)_2$—, $C_{1-4}$-alkyl-C(O)— and $R^{2.1.1}$-A-.

11. The compound of formula 1, according to claim 1, wherein $R^1$ is H, $R^3$ is H or F, and $R^2$ and $R^4$ are together with two adjacent carbon atoms of the heteroaryl ring a 5- or 6-membered aryl, wherein the 5- or 6-membered aryl is optionally substituted by one or two residues selected from among halogen, —CN, $C_{5-10}$-heteroaryl-, containing one, two, three or four heteroatoms selected independently from S, S(O), $S(O)_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $C_{5-10}$-heterocyclyl-, containing one, two, three or four heteroatoms selected independently from S, S(O), $S(O)_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-haloalkyl-; $C_{3-6}$-cycloalkyl-, $C_{1-4}$-alkyl-O—$C_{1-4}$-alkyl, H(O)C—, $C_{1-4}$-alkyl-(O)C—, tetrahydrofuranylmethyl- and tetrahydropyranylmethyl, or salts thereof.

12. A compound of formula 1'

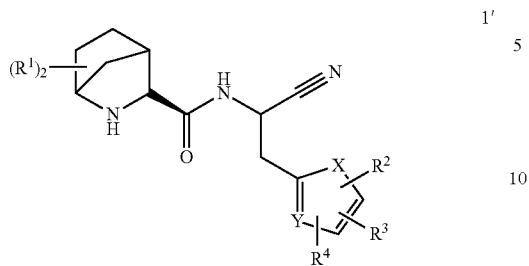

wherein X, Y, $R^1$, $R^2$, $R^3$ and $R^4$ have the meaning of claim 1.

13. A pharmaceutical composition, comprising a compound of formula 1 according to claim 1 or a pharmaceutically acceptable salt thereof.

14. The pharmaceutical composition according to claim 13 further comprising a pharmaceutically active compound selected from among the group consisting of betamimetics, anticholinergics, corticosteroids, PDE4-inhibitors, LTD4-antagonists, EGFR-inhibitors, CRTH2 inhibitors, 5-LO-inhibitors, Histamine receptor antagonists, CCR9 antagonists and SYK-inhibitors, NE-inhibitors, MMP9 inhibitors and MMP12 inhibitors, or combinations of two or three of the pharmaceutically active compound.

* * * * *